United States Patent

Natsugari et al.

[11] Patent Number: 6,147,071
[45] Date of Patent: Nov. 14, 2000

[54] CYCLIC COMPOUNDS, THEIR PRODUCTION AND USE

[75] Inventors: Hideaki Natsugari, Hyogo; Takenori Ishimaru; Takayuki Doi, both of Osaka; Yoshinori Ikeura, Nara; Chiharu Kimura, Hyogo, all of Japan

[73] Assignee: Takeda Chemical Industries, Ltd., Osaka, Japan

[21] Appl. No.: 09/087,894

[22] Filed: Jun. 1, 1998

Related U.S. Application Data

[62] Division of application No. 08/621,360, Mar. 25, 1996, Pat. No. 5,786,352.

[30] Foreign Application Priority Data

| Mar. 24, 1995 | [JP] | Japan | 7-091436 |
| Jul. 20, 1995 | [JP] | Japan | 7-207553 |
| Sep. 18, 1995 | [JP] | Japan | 7-264727 |
| Jan. 23, 1996 | [JP] | Japan | 8-030033 |

[51] Int. Cl.⁷ .......... A61K 31/55; A61K 31/553; A61K 31/554; C07D 267/22; C07D 267/02
[52] U.S. Cl. .......... 514/211.05; 514/302; 540/455; 540/488; 540/490
[58] Field of Search .......... 540/455, 488, 540/490; 514/302, 211, 211.05

[56] References Cited

U.S. PATENT DOCUMENTS

| 3,987,047 | 10/1976 | Griss et al. | 260/287 |
| 4,746,657 | 5/1988 | Cale, Jr. | 514/215 |

FOREIGN PATENT DOCUMENTS

| 0 566 069 A1 | 10/1993 | European Pat. Off. |
| 0 585 913 A2 | 3/1994 | European Pat. Off. |
| 0 634 402 | 1/1995 | European Pat. Off. |
| 0 652 218 A1 | 5/1995 | European Pat. Off. |
| 23 57 253 | 5/1975 | Germany. |
| 26 17 101 | 11/1977 | Germany. |
| 26 38 828 | 3/1978 | Germany. |
| 27 22 416 | 11/1978 | Germany. |

OTHER PUBLICATIONS

R. Madhav, A New Synthesis of Compounds in the 5H–Pyrrolo–[3,4–b] Pyridine Series, pp. 609–610, Oct. 1973.

Snyder et al., Preparation of Compounds in the New Dipyrrolo[3,4–b:3',4'–e–]–Pyridine Series From 1–Benzylidene–2,3–Dioxopyrrolidines., pp. 603–607, May–Jun. 1982.

Sato et al. Synthetic Studies on Cardiovascular Agents, Chemical Abstracts, vol. 89, No. 7, Aug. 1978, p. 570, Zasshi, vol. 98, No. 4, 1978, pp. 448–65.

*Primary Examiner*—Bruck Kifle
*Attorney, Agent, or Firm*—Foley & Lardner

[57] ABSTRACT

Novel compounds of the following general formula or salts thereof.

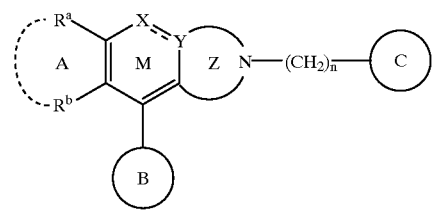

wherein Ring M is a heterocyclic ring having —N=CC<, —CO—N< or —CS—N< as the partial structure —X . . . . Y<; $R^a$ and $R^b$ are bonded to each other to form Ring A, or they are the same or different and represent, independently, a hydrogen atom or a substituent on the Ring M; Ring A and Ring B represent, independently, an optionally substituted homocyclic or heterocyclic ring, and at least one of them is optionally substituted heterocyclic ring; Ring C is optionally substituted homocyclic or heterocyclic ring; Ring Z is an optionally substituted ring; and n represents an integer of from 1 to 6, or a salt thereof, which has an excellent tachykinin receptor antagonistic effect, and their production, and pharmaceutical compositions.

11 Claims, No Drawings

CYCLIC COMPOUNDS, THEIR PRODUCTION AND USE

This application is a divisional of application Ser. No. 08/621,360, filed Mar. 25, 1996 now U.S. Pat. No. 5,786,352.

The present invention relates to novel cyclic compounds having an excellent tachykinin receptor antagonistic effect, and a method for producing them, as well as a composition containing the foregoing cyclic compounds.

Capsaicine is a stimulative essential component to be in a capsicum, and this is known as a substance which selectively stimulates C-fibers comprising substance P (hereinafter simply referred to as SP), neurokinin A (NKA), calcitonin gene-related peptides (CGRP), etc. of the primary sensory nerve to thereby liberate such intrinsic neuropeptides.

Tachykinin is a generic term for a group of neuropeptides. Substance P (SP), neurokinin A (NKA) and neurokinin B (NKB) are known in mammals, and it is known that these peptides bind to the corresponding receptors (neurokinin-1, neurokinin-2, neurokinin-3) that exist in living body to thereby exhibit various biological activities.

Of such neuropeptides, substance P has the longest history and has been studied in detail. In 1931, the existence of substance P in the extract from equine intestines was confirmed, and its structure was determined in 1971. Substance P is a peptide consisting of 11 amino acids. It is known that substance P plays an important role in the peripheral and central nervous systems as an information transmitter substance or the like. In addition, it is considered that substance P participates in various disorders (for example, pain, inflammation, allergy, pollakisuria, urinary incontinence, respiratory tract disorders, psycosis, etc.)

Substance P is broadly distributed over the central and peripheral nervous systems, while having, in addition to the function as a transmitter substance for primary sensory neurons, various physiological activities for vasodilation, promotion of vascular extravasation, contraction of smooth muscles, neuronal excitatory activity, salivation, promotion of diuresis, immunological enhancement, etc. In particular, it is known that SP liberated from the terminal of the spinal (dorsal) horn due to a pain impulse transmits the pain to secondary neurons and that SP liberated from the peripheral terminal induces an inflammatory response in the nociceptive field. In addition, it is considered that SP is involved in Alzheimer type dementia [see review article: Physiological Reviews, Vol. 73, pp. 229–308, (1993); Journal of Autonomic Pharmacology, Vol. 13, pp. 23–93, (1993)].

At present, the following compounds have been known as those having a substance P receptor antagonistic effect.

(1) In Japanese Patent Laid-Open No. 1-287095, disclosed are compounds of a formula:

$R^1$-A-D-Trp($R^2$)-Phe—$R^3$ wherein $R^1$ represents a hydrogen atom or an amino-protecting group; $R^2$ represents a hydrogen atom, an amino-protecting group, a carbamoyl-(lower) alkyl group, a carboxy-(lower) alkyl group, or a protected carboxy-(lower) alkyl group; $R^3$ represents an ar-(lower) alkyl group, a group of a formula:

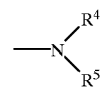

wherein $R^4$ and $R^5$ represent, independently, a hydrogen atom, an aryl group or an optionally substituted lower alkyl group, or $R^4$ and $R^5$ are bonded to each other to form a benzene-condensed lower alkylene group, or a group of a formula:

—$OR^6$ wherein $R^6$ represents a hydrogen atom, an aryl group or an optionally substituted lower alkyl group;

A represents a single bond or one or two amino acid residues, provided that when A is one amino acid residue of -D-Trp-, $R^4$ is not be a hydrogen atom, and a salt thereof.

(2) In EP-A-436,334, disclosed are compounds of a formula:

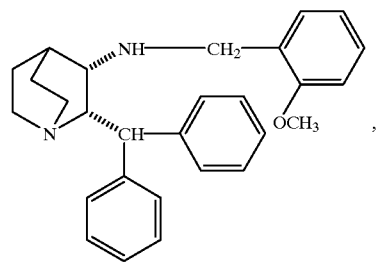

etc.

(3) In EP-A-429,366, disclosed are compounds of a formula:

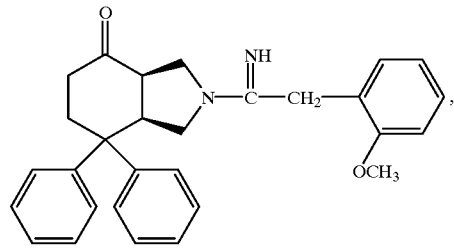

etc.

(4) In Journal of Medicinal Chemistry, Vol. 34, p. 1751 (1991), disclosed are compounds of a formula:
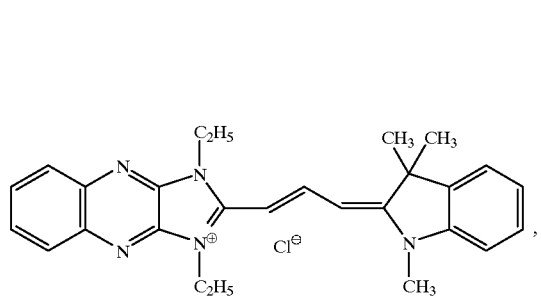
etc.
(5) In WO91/09844, disclosed are compounds of a formula:
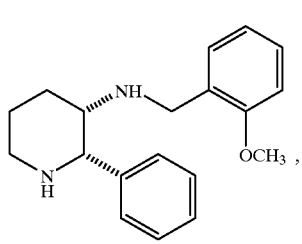
etc.
(6) In EP-A-522,808, disclosed are compounds of a formula:
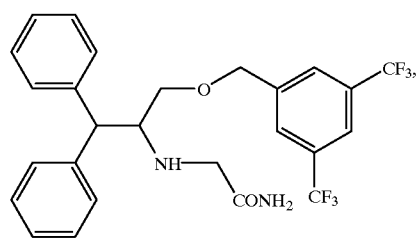
etc.
(7) In WO93/01169, disclosed are compounds of a formula:
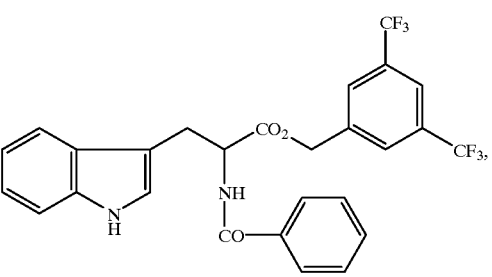
etc.
(8) In EP-A-532,456, disclosed are compounds of a formula:
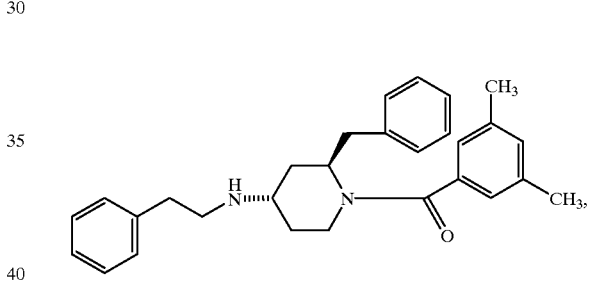
etc.
(9) In Bioorganic & Medicinal Chemistry Letters, Vol. 4, p. 1903 (1994), disclosed is a compound of a formula:
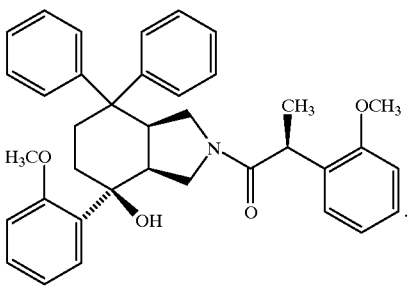

(10) In European Journal of Pharmacology, Vol. 250, p. 403 (1993), disclosed is a compound of a formula:

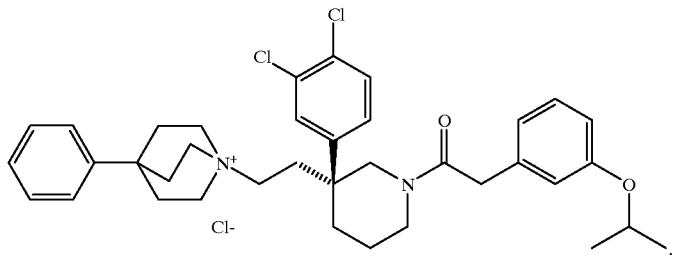

(11) In EP-A-585,913, disclosed are compounds of a formula:

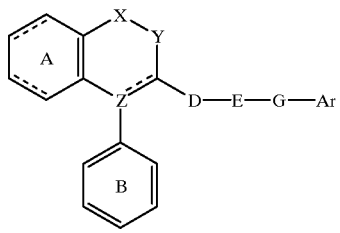

wherein
Ring A may be optionally substituted;
Ring B represents an optionally substituted benzene ring;
one of X and Y represents —NR$^1$— (where R$^1$ represents a hydrogen atom, an optionally substituted hydrocarbon group, an optionally substituted hydroxyl group or an optionally substituted amino group), —O— or —S—, while the other represents —CO—, —CS— or —C(R$^2$)R$^{2a}$— (where R$^2$ and R$^{2a}$ represent, independently, a hydrogen atom or an optionally substituted hydrocarbon group); or one of these represents —N=C, while the other represents =CR$^3$— (where R$^3$ represents a hydrogen atom, a halogen atom, an optionally substituted hydrocarbon group, an optionally substituted amino group, a substituted hydroxyl group, or a mercapto group optionally substituted by an optionally substituted hydrocarbon group);
..... represents a single bond or a double bond;
Z represents =CR$^4$— (where R$^4$ represents a hydrogen atom, a hydroxyl group or an optionally substituted hydrocarbon group) or a nitrogen atom, when ..... adjacent to Z is a single bond, and represents a carbon atom when ..... adjacent to Z is a double bond;
D represents a C$_{1-3}$ alkylene group optionally substituted by oxo or thioxo group(s), or D and Y may together form a 5- to 7-membered ring optionally substituted by oxo or thioxo group(s);
E represents —NR$^5$— (where R$^5$ represents a hydrogen atom, or an optionally substituted hydrocarbon group, or R$^5$ and Y may together form a 5- to 7-membered ring optionally substituted by oxo or thioxo group(s)), —O— or —S(O)$_n$— (where n represents 0, 1 or 2);
G represents a bond or a C$_{1-3}$ alkylene group;
Ar represents an optionally substituted aryl group or an optionally substituted heterocyclic group;
provided that (i) when —X—Y— is —O—CO— or —CO—O—, D is —CO— and E is —NR$^5$—, then (a)

G is a C$_{1-3}$ alkylene group, and Ar is a substituted aryl group or a substituted heterocyclic group, or (b) G is a bond, and R$^5$ is an optionally substituted hydrocarbon group, and (ii) when —X—Y— is —NH—CO—, then D is —CO—, or a salt thereof, etc.

On the other hand, the following compounds have been known as those having a neurokinin-A receptor antagonistic effect.

(1) In Life Sciences, Vol. 50, PL101 (1992), disclosed are compounds of a formula:

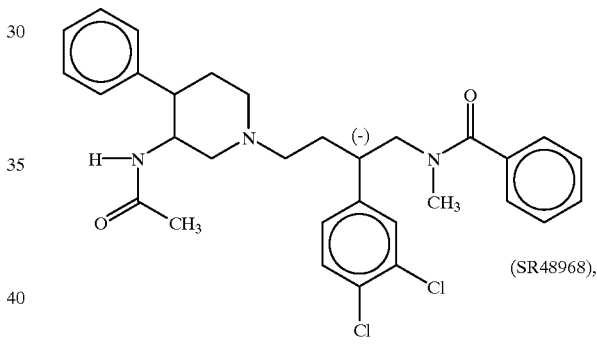

etc.

(2) In Bioorganic & Medicinal Chemistry Letters, Vol. 4, P.1951 (1994), disclosed are compounds of a formula:

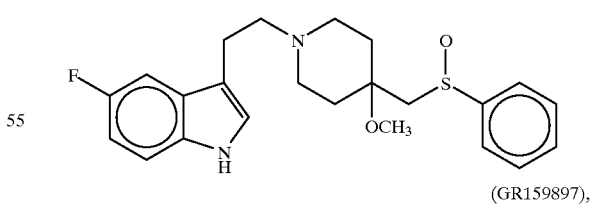

etc.

(3) In AFMC International Medicinal Chemistry Symposium (Tokyo), P6M139 (1995.9), disclosed are compounds of a formula:

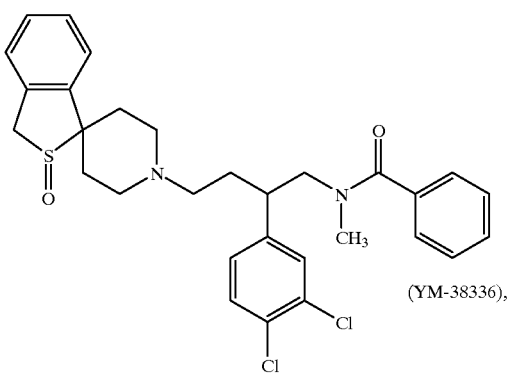

(YM-38336), etc.

(4) In Tachykinins (Florence), P.21 (1995.10), disclosed are compounds of a formula:

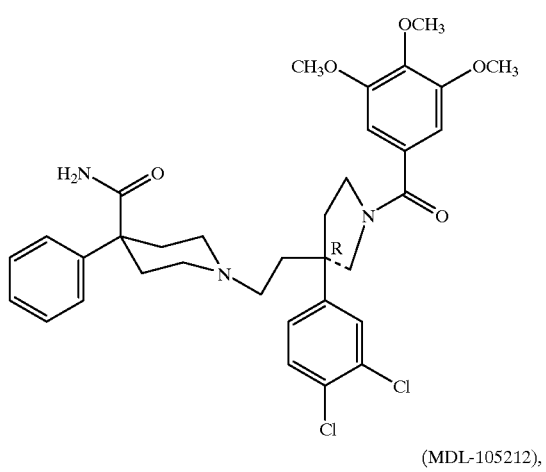

(MDL-105212), etc.

(5) In Journal of Medicinal Chemistry, Vol. 38, P.3772 (1995), disclosed are compounds of a formula:

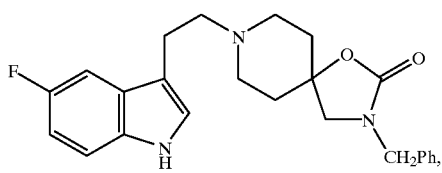

etc.

(6) In Bioorganic & Medicinal Chemistry Letters, Vol. 5, P.2879 (1995), disclosed are compounds of a formula:

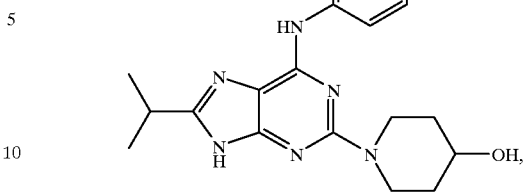

etc.

However, these references do not disclose condensed heterocyclic compounds having a basic skeleton of a formula:

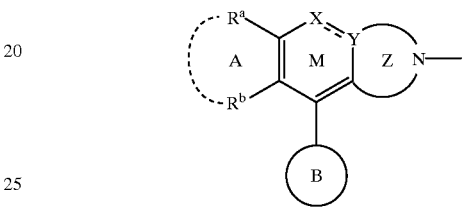

wherein

Ring M is a heterocyclic ring having —N=C<, —CO—N< or —CS—N< as the partial structure —X.....Y<;

$R^a$ and $R^b$ are bonded to each other to form Ring A, or they are the same or different and represent, independently, a hydrogen atom or a substituent on the Ring M;

Ring A and Ring B represent, independently, an optionally substituted homocyclic or heterocyclic ring, and at least one of them is an optionally substituted heterocyclic ring; and Ring Z is an optionally substituted nitrogen-containing heterocyclic ring. Nor do these references disclose the properties of such compounds.

At present, compounds which have excellent tachykinin receptor antagonistic effects (especially, substance P and NKA receptor antagonistic effects) and are sufficiently satisfactory as medicines for the above-mentioned various disorders (especially, pollakisuria, urinary incontinence, etc.) from the viewpoint of the safety of themselves and the persistency of their effects have not been found as of yet. Therefore, it is desired to develop compounds which have chemical structures different from those of the above-mentioned known compounds and which have an excellent tachykinin receptor antagonistic effect and are therefore sufficiently satisfactory as medicines for such disorders.

Accordingly, the object of the present invention is to provide novel compounds having high tachykinin receptor antagonistic effects (especially, substance P and NKA receptor antagonistic effects) and a method for producing them, etc.

The other object of the present invention is to provide pharmaceutical compositions having a high tachykinin receptor antagonistic effects (especially, a substance P and NKA receptor antagonistic effects), tachykinin receptor antagonists and ameliorative preparations for disorders of micturition, etc.

The present inventors have assiduously studied in consideration of the above-mentioned situation and, as a result, have synthesized for the first time condensed heterocyclic compounds having, as the basic skeleton, a partial chemical structure of a formula:

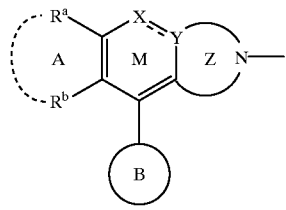

wherein the symbols have the same meanings as mentioned above, and have found unexpectedly that these condensed heterocyclic compounds have excellent tachykinin receptor antagonistic effects (especially, substance P and NKA receptor antagonistic effects) as based on their peculiar chemical structures and are sufficiently satisfactory as medicines. On the basis of these findings, the present inventors have completed the present invention.

Specifically, the present invention relates to (1) A compound of the formula (I):

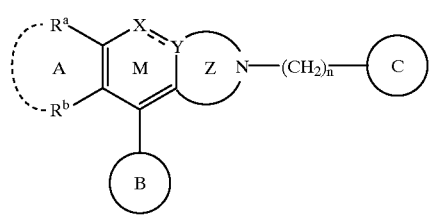

(I)

wherein ring M is a heterocyclic ring having —N=C<, —CO—N< or —CS—N< as the partial structure —X.....Y<;

$R^a$ and Rb are bonded to each other to form Ring A, or they are the same or different and represent, independently, a hydrogen atom or a substituent on the Ring M;

Ring A and Ring B represent, independently, an optionally substituted homocyclic or heterocyclic ring, and at least one of them is an optionally substituted heterocyclic ring;

Ring C is an optionally substituted homocyclic or heterocyclic ring;

Ring Z is an optionally substituted nitrogen-containing heterocyclic ring; and n is an integer of 1 to 6, or a salt thereof, (2) A compound as described in (1), wherein $R^a$ and $R^b$ are the same or different and represent, independently, (i) a hydrogen atom,
(ii) a $C_{1-6}$ alkyl group optionally having from 1 to 5 substituents selected from
  (a) a hydroxyl group,
  (b) a $C_{1-6}$ alkoxy group,
  (c) a $C_{1-6}$ alkylthio group,
  (d) an amino group,
  (e) a $C_{1-7}$ acylamino group,
  (f) a carboxyl group,
  (g) a nitro group,
  (h) a mono- or di-$C_{1-6}$ alkylamino group,
  (i) a mono- or di-$C_{3-8}$ cycloalkylamino group,
  (j) a $C_{6-10}$ arylamino group,
  (h) a 5-membered to 9-membered cyclicamino group which may have 1 to 3 hetero atoms selected from nitrogen, oxygen and sulfur atoms,
  (l) a 5-membered to 6-membered aromatic heterocyclic group having from 1 to 3 hetero atoms selected from nitrogen, oxygen and sulfur atoms, in addition to carbon atoms,
  (m) a 5-membered to 9-membered non-aromatic heterocyclic ring having from 1 to 3 hetero atoms selected from nitrogen, oxygen and sulfur atoms, in addition to carbon atoms,
  (n) a $C_{1-4}$ alkylsulfonylamino group,
  (o) a $C_{1-6}$ alkyl-carbonyloxy group and
  (p) a halogen atom,
(iii) an optionally halogenated $C_{1-6}$ alkoxy group,
(iv) an optionally halogenated $C_{1-6}$ alkylthio group,
(v) a $C_{3-10}$ cycloalkyl group,
(vi) a $C_{6-10}$ aryl group,
(vii) a $C_{1-7}$ acylamino group,
(viii) a $C_{1-3}$ acyloxy group,
(ix) a hydroxy group,
(x) a nitro group,
(xi) a cyano group,
(xii) an amino group,
(xiii) a mono- or di-$C_{1-6}$ alkylamino group,
(xiv) a 5-membered to 9-membered cyclicamino group which may have 1 to 3 hetero atoms selected from nitrogen, oxygen and sulfur atoms, in addition to one nitrogen atom,
(xv) a $C_{1-6}$ alkylcarbonylamino group,
(xvi) a $C_{1-6}$ alkylsulfonylamino group,
(xvii) a $C_{1-6}$ alkoxycarbonyl group,
(xviii) a carboxyl group,
(xix) a $C_{1-6}$ alkylcarbonyl group,
(xx) a carbamoyl group,
(xxi) a mono- or di-$C_{1-6}$ alkylcarbamoyl group,
(xxii) $C_{1-6}$ alkylsulfonyl group, or
(xxiii) an oxo group; or $R^{a\ and\ Rb}$ are bonded to each other to form Ring A, and the Ring A is a 5-membered to 6-membered aromatic group having from 1 to 3 hetero atoms selected from nitrogen, oxygen and sulfur atoms, in addition to carbon atoms, a 5-membered to 9-membered non-aromatic heterocyclic group having from 1 to 3 hetero atoms selected from nitrogen, oxygen and sulfur atoms, in addition to carbon atoms, or a 3-membered to 10-membered cyclic hydrocarbon group each of which may have 1 to 4 substituents selected from (i) a halogen atom,
(ii) a $C_{1-6}$ alkyl group optionally having from 1 to 5 substituents selected from
  (a) a hydroxyl group,
  (b) an amino group,
  (c) a carboxyl group,
  (d) a nitro group,
  (e) a mono- or di-$C_{1-6}$ alkylamino group,
  (f) a $C_{1-6}$ alkyl-carbonyloxy group and
  (g) a halogen atom,
(iii) an optionally halogenated $C_{1-6}$ alkoxy group,
(iv) an optionally halogenated $C_{1-6}$ alkylthio group,
(v) a $C_{6-10}$ aryl group,
(vi) a $C_{1-7}$ acylamino group,
(vii) a $C_{1-3}$ acyloxy group,
(viii) a hydroxy group,
(ix) a nitro group,
(x) a cyano group, (xi) an amino group,
(xii) a mono- or di-$C_{1-6}$ alkylamino group,
(xiii) a 5-membered to 9-membered cyclicamino group which may have 1 to 3 hetero atoms selected from nitrogen, oxygen and sulfur atoms, in addition to one nitrogen atom,
(xiv) a $C_{1-6}$ alkylcarbonylamino group,
(xv) a $C_{1-6}$ alkylsulfonylamino group,
(xvi) a $C_{1-6}$ alkoxycarbonyl group,
(xvii) a carboxyl group,
(xviii) a $C_{1-6}$ alkylcarbonyl group,
(xix) a carbamoyl group,
(xx) a mono- or di-$C_{1-6}$ alkylcarbamoyl group,
(xxi) a $C_{1-6}$ alkylsulfonyl group, or
(xxii) an oxo group;
the Ring B is a 5-membered to 6-membered aromatic group having from 1 to 3 hetero atoms selected from nitrogen, oxygen and sulfur atoms, in addition to carbon atoms, a 5-membered to 9-membered non-aromatic heterocyclic group having from 1 to 3 hetero atoms selected from nitrogen, oxygen and sulfur atoms, in addition to carbon atoms, or a 3-membered to 10-membered cyclic hydrocarbon group each of which may have 1 to 4 substituents selected from
(i) a halogen atom,
(ii) a $C_{1-6}$ alkyl group optionally having from 1 to 5 substituents selected from
  (a) a hydroxyl group,
  (b) an amino group,
  (c) a carboxyl group,
  (d) a nitro group,
  (e) a mono- or di-$C_{1-6}$ alkylamino group,
  (f) a $C_{1-6}$ alkyl-carbonyloxy group and
  (g) a halogen atom,
(iii) an optionally halogenated $C_{1-6}$ alkoxy group,
(iv) an optionally halogenated $C_{1-6}$ alkylthio group,
(v) a $C_{6-10}$ aryl group,
(vi) a $C_{1-7}$ acylamino group,
(vii) a $C_{1-3}$ acyloxy group,
(viii) a hydroxy group,
(ix) a nitro group,
(x) a cyano group,
(xi) an amino group,
(xii) a mono- or di-$C_{1-6}$ alkylamino group,
(xiii) a 5-membered to 9-membered cyclicamino group which may have 1 to 3 hetero atoms selected from nitrogen, oxygen and sulfur atoms, in addition to one nitrogen atom,
(xiv) a $C_{1-6}$ alkylcarbonylamino group,
(xv) a $C_{1-6}$ alkylsulfonylamino group,
(xvi) a $C_{1-6}$ alkoxycarbonyl group,
(xvii) a carboxyl group,
(xviii) a $C_{1-6}$ alkylcarbonyl group,
(xix) a carbamoyl group,
(xx) a mono- or di-$C_{1-6}$ alkylcarbamoyl group,
(xxi) a $C_{1-6}$ alkylsulfonyl group, and
(xxii) an oxo group;
the Ring C is a 5-membered to 10-membered heterocyclic group which may have 1 to 4 hetero atoms selected from nitrogen, oxygen and sulfur atoms which optionally having 1 to 5 substituents selected from
(i) a halogen atom,
(ii) an optionally halogenated $C_{1-10}$ alkyl group,
(iii) an amino-substituted $C_{1-4}$ alkyl group,
(vi) a mono- or di-$C_{1-4}$ alkylamino-substituted $C_{1-4}$ alkyl group,
(v) a carboxyl-substituted $C_{1-4}$ alkyl group,
(vi) a $C_{1-4}$ alkoxy-carbonyl-substituted $C_{1-4}$ alkyl group,
(vii) a hydroxy-substituted $C_{1-4}$ alkyl group,
(viii) a $C_{1-4}$ alkoxy-carbonyl-substituted $C_{1-4}$ alkyl group,
(ix) a $C_{3-10}$ cycloalkyl group,
(x) a nitro group,
(xi) a cyano group,
(xii) a hydroxyl group,
(xiii) an optionally-halogenated $C_{1-10}$ alkoxy group,
(xiv) an optionally-halogenated $C_{1-4}$ alkylthio group,
(xv) an amino group,
(xvi) a mono- or di-$C_{1-4}$ alkylamino group,
(xvii) a 5-membered to 9-membered cyclic amino group optionally having 1 to 3 hetero atoms selected from nitrogen, oxygen and sulfur atoms, in addition to one nitrogen atom,
(xviii) a $C_{1-4}$ alkyl-carbonylamino group,
(xix) an aminocarbonyloxy group,
(xx) a mono- or di-$C_{1-4}$ alkylaminocarbonyloxy group,
(xxi) a $C_{1-4}$ alkylsulfonylamino group,
(xxii) a $C_{1-4}$ alkoxy-carbonyl group,
(xxiii) an aralkyloxycarbonyl group,
(xxiv) a carboxyl group,
(xxv) a $C_{1-6}$ alkyl-carbonyl group,
(xxvi) a $C_{3-6}$ cycloalkyl-carbonyl group,
(xxvii) a carbamoyl group,
(xxviii) a mono- or di-$C_{1-4}$ alkylcarbamoyl group,
(xxix) a $C_{1-6}$ alkylsulfonyl group and
(xxx) a 5-membered or 6-membered aromatic monocyclic heterocyclic group having 1 to 4 hetero atoms selected from nitrogen, oxygen and sulfur atoms, which may have 1 to 3 substituents selected from an optionally halogenated $C_{1-4}$ alkyl; or
a 3-membered to 10-membered cyclic hydrocarbon group, optionally having 1 to 5 substituents selected from
(i) a halogen atom,
(ii) an optionally halogenated $C_{1-10}$ alkyl group,
(iii) an amino-substituted $C_{1-4}$ alkyl group,
(iv) a mono- or di-$C_{1-4}$ alkylamino-substituted $C_{1-4}$ alkyl group,
(v) a carboxyl-substituted $C_{1-4}$ alkyl group,
(vi) a hydroxy-substituted $C_{1-4}$ alkyl group,
(vii) a $C_{1-4}$ alkoxy-carbonyl-substituted $C_{1-4}$ alkyl group,
(viii) a $C_{3-10}$ cycloalkyl group,
(ix) a nitro group,
(x) a cyano group,
(xi) a hydroxyl group,
(xii) an optionally-halogenated $C_{1-10}$ alkoxy group,
(xiii) an optionally-halogenated $C_{1-4}$ alkylthio group,
(xiv) an amino group,
(xv) a mono- or di-$C_{1-4}$ alkylamino group,
(xvi) a 5-membered to 9-membered cyclic amino group optionally having 1 to 3 hetero atoms selected from nitrogen, oxygen and sulfur atoms, in addition to one nitrogen atom,
(xvii) a $C_{1-4}$ alkyl-carbonylamino group,
(xviii) an aminocarbonyloxy group,
(xiv) a mono- or di-$C_{1-4}$ alkylaminocarbonyloxy group,
(xx) a $C_{1-4}$ alkylsulfonylamino group,
(xxi) a $C_{1-4}$ alkoxy-carbonyl group,
(xxii) an aralkyloxycarbonyl group,
(xxiii) a carboxyl group,
(xxiv) a $C_{1-6}$ alkyl-carbonyl group, (xxv) a $C_{3-6}$ cycloalkyl-carbonyl group,
(xxvi) a carbamoyl group,
(xxvii) a mono- or di-$C_{1-4}$ alkylcarbamoyl group,
(xxviii) a $C_{1-6}$ alkylsulfonyl group and
(xxix) a 5-membered or 6-membered aromatic monocyclic heterocyclic group having 1 to 4 hetero atoms selected from nitrogen, oxygen and sulfur atoms, which may have 1 to 3 substituents selected from an optionally halogenated $C_{1-4}$ alkyl;
the Ring Z is a 5-membered to 12-membered heterocyclic ring optionally having at least one hetero atom selected from nitrogen, oxygen and sulfur atoms, in addition to Y and the nitrogen atom, having 1 to 5 substituents selected from
(i) a $C_{1-6}$ alkyl group,
(ii) a $C_{2-6}$ alkenyl group,
(iii) a $C_{2-6}$ alkynyl group,
(iv) a $C_{3-8}$ cycloalkyl group,
(v) a $C_{3-8}$ cycloalkyl-$C_{1-4}$ alkyl group,
(vi) a $C_{6-14}$ aryl group,
(vii) a nitro group,
(viii) a cyano group,
(ix) a hydroxyl group,
(x) a $C_{1-4}$ alkoxy group,
(xi) a $C_{1-4}$ alkylthio group,
(xii) an amino group,
(xiii) a mono- or di-$C_{1-4}$ alkylamino group,
(xiv) a 5-membered to 9-membered cyclic amino group optionally having 1 to 3 hetero atoms selected from nitrogen, oxygen and sulfur atoms, in addition to one nitrogen atom,
(xv) a $C_{1-4}$ alkyl-carbonylamino group,
(xvi) a $C_{1-4}$ alkylsulfonylamino group,
(xvii) a $C_{1-4}$ alkoxy-carbonyl group,
(xviii) a carboxyl group,
(xix) a $C_{1-6}$ alkyl-carbonyl group,
(xx) a carbamoyl group,
(xxi) a mono- or di-$C_{1-4}$ alkylcarbamoyl group,
(xxii) a $C_{1-6}$ alkylsulfonyl group,
(xxiii) an oxo group, and
(xxiv) a thioxo group, (3) A compound as described in (1), wherein $R^a$ and $R^b$ are bonded to each other to form Ring A, Ring C is an optionally substituted benzene ring or an optionally substituted heterocyclic ring, Ring Z is a nitrogen-containing heterocyclic ring optionally substituted by an oxo group, and n represents 1 or 2, (4) A compound as described in (1), wherein Ring Z is a nitrogen-containing heterocyclic ring optionally substituted by an oxo group, (5) A compound as described in (1), wherein one of Ring A and Ring B is an optionally substituted aromatic ring and the other is an optionally substituted aromatic heterocyclic ring, (6) A compound as described in (1), wherein Ring A is an optionally substituted aromatic heterocyclic ring, and Ring B is an optionally substituted benzene ring, (7) A compound as described in (6), wherein the aromatic heterocyclic ring is a 5-membered or 6-membered, aromatic heterocyclic ring having one or two hetero atoms selected from nitrogen, sulfur and oxygen atoms, in addition to carbon atoms, (8) A compound as described in (1), wherein Ring C is an optionally substituted benzene ring, (9) A compound as described in (1), wherein Ring C is a benzene ring which may have from 1 to 3 substituents selected from a halogen atom, an optionally halogenated $C_{1-6}$ alkyl group and an optionally halogenated $C_{1-6}$ alkoxy group,

(10) A compound as described in (1), wherein Ring Z is a 5-membered to 10-membered ring optionally substituted by 1 or 2 oxo groups,

(11) A compound as described in (1), wherein —X⎯⎯⎯Y< is —N═CC< or —CO—N<,

(12) A compound as described in (1), wherein n is 1,

(13) A compound as described in (1), wherein Ring A is an optionally substituted pyridine ring, Ring B is an optionally substituted benzene ring, Ring C is an optionally substituted benzene ring, Ring Z is a 5-membered to 10-membered ring optionally substituted by an oxo group, —X⎯⎯⎯Y< is —CO—N<, and n is 1,

(14) A compound as described in (1), wherein $R^a$ and $R^b$ are the same or different and represent, independently, a hydrogen atom, a halogen atom, an optionally substituted alkyl group, an optionally halogenated alkoxy group, an optionally halogenated alkylthio group, a cycloalkyl group, an aryl group, an acylamino group, an acyloxy group, a hydroxy group, a nitro group, a cyano group, an amino group, a mono- or di-alkylamino group, a cyclic amino group, an alkylcarbonylamino group, an alkylsulfonylamino group, an alkoxycarbonyl group, a carboxyl group, an alkylcarbonyl group, a carbamoyl group, a mono- or di-alkylcarbamoyl group, an alkylsulfonyl group or an oxo group,

(15) A compound as described in (1), wherein $R^a$ and $R^b$ are the same or different and represent, independently,
(i) a hydrogen atom,
(ii) a $C_{1-6}$ alkoxy-$C_{1-6}$ alkyl group,
(iii) a $C_{1-6}$ alkylthio-$C_{1-6}$ alkyl group,
(iv) an amino-$C_{1-6}$ alkyl group,
(v) a $C_{1-7}$ acylamino-$C_{1-6}$ alkyl group,
(vi) a mono- or di-$C_{1-6}$ alkylamino-$C_{1-4}$ alkyl group,
(vii) $C_{3-10}$ cycloamino-$C_{1-6}$ alkyl group,
(viii) a $C_{1-6}$ alkyl group having 5-membered or 6-membered cycloamino optionally substituted by $C_{1-6}$ alkyl group,
(ix) a $C_{1-6}$ alkylsulfonylamino-$C_{1-6}$ alkyl group, or
(x) a $C_{1-6}$ alkylcarbonyloxy-$C_{1-6}$ alkyl; or
$R^a$ and $R^b$ are bonded to each other to form pyridine ring which is optionally substituted by 1 to 3 substituents selected from a halogen atom and a $C_{1-4}$ alkyl group;
Ring B is a benzene ring optionally having 1 to 3 substituents selected from a halogen atom, an optionally halogenated $C_{1-4}$ alkyl group and an optionally halogenated $C_{1-4}$ alkoxy group;
Ring C is a benzene ring optionally having 1 to 3 substituents selected from a halogen atom, an optionally halogenated $C_{1-4}$ alkyl group, an optionally halogenated $C_{1-4}$ alkoxy group, an amino group optionally substituted by $C_{1-4}$ alkyl group, a $C_{1-3}$ acyloxy group and a hydroxyl group;
Ring Z is a 5-membered to 10-membered nitrogen containing heterocyclic ring optionally having an oxo group and optionally substituted by a $C_{1-4}$ alkyl group or a hydroxyl group; —X⎯⎯⎯Y< is —N═CC< or —CO—N<; and n is an integer of 1,

(16) A compound as described in (15), wherein $R^a$ and $R^b$ are bonded to each other to form Ring A, and —X⎯⎯⎯Y< is —CO—N<,

(17) A compound as described in (16), wherein the Ring A is an unsubstituted pyridine ring,

(18) A compound as described in (16), wherein the Ring B is a benzene ring which optionally substituted by an optionally halogenated $C_{1-4}$ alkyl group,

(19) A compound as described in (16), wherein the Ring C is an benzene ring which may have 1 to 3 substituents selected from a halogen atom, an optionally halogenated $C_{1-4}$ alkyl group and an optionally halogenated $C_{1-4}$ alkoxy group,

(20) A compound as described in (16), wherein Ring Z is

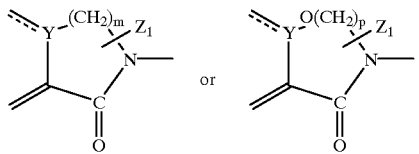

or wherein, m and p are the same or different and represent, independently, an integer of from 1 to 5, $Z_1$ and $Z_2$ are the same or different and represent, independently, an hydrogen atom, an $C_{1-4}$ alkyl group or a hydroxyl group and Y is the same meaning as described in (15),

(21) A compound as described in (1), which is (9S)-7-[3,5-bis(trifluoromethyl)benzyl]-6,7,8,9,10,12-hexahydro-9-methyl-6,12-dioxo-5-phenyl[1,4]diazepino[2,1-g][1,7]naphthyridine,

(22) A compound as described in (1), which is (9s)-7-[3,5-bis(trifluoromethyl)benzyl]-6,7,8,9,10,12-hexahydro-9-methyl-5-(4-methylphenyl)-6,12-dioxo[1,4]diazepino[2,1-g][1,7]naphthyridine,

(23) A compound as described in (1), which is (9R)-7-[3,5-bis(trifluoromethyl)benzyl]-6,7,8,9,10,11-hexahydro-9-methyl-6,13-dioxo-5-phenyl-13H-[1,4]diazocino[2,1-g][1,7]naphthyridine,

(24) A compound as described in (1), which is (9R)-7-[3,5-bis(trifluoromethyl)benzyl]-6,7,8,9,10,11-hexahydro-9-methyl-5-(4-methylphenyl)-6,13-dioxo-13H-[1,4]diazocino[2,1-g][1,7]naphthyridine,

(25) A process for producing a compound as described in (1), characterized by cyclizing a compound of a formula:

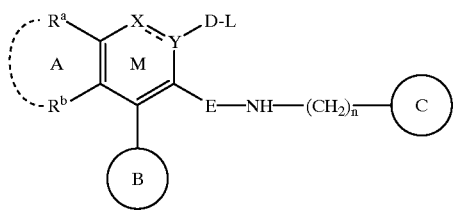

wherein D and E represent groups from which ring Z as set forth in claim 1 is formed via the nitrogen atom adjacent to E, L represents a leaving group, and the other symbols are the same meanings as those described in (1), or a salt thereof,

(26) A pharmaceutical composition comprising a compound as described in (1),

(27) A composition for antagonizing tachykinin receptor comprises a compound as described in (1),

(28) A composition for antagonizing Substance P receptor comprises a compound as described in (1),

(29) A composition for antagonizing neurokinin A receptor comprises a compound as described in (1),

(30) A pharmaceutical composition for preventing or treating disorders of micturition which comprises a compound as described in (1) and a pharmaceutical acceptable carrier thereof,

(31) A pharmaceutical composition for preventing or treating disorders of asthma, rheumatoid arthritis, osteoarthritis, pain, migraine, cough, irritable bowel syndrome or emesis, which comprises a compound as described in (1) and a pharmaceutical acceptable carrier thereof,

(32) A method for antagonizing tachykinin receptor in mammals which comprises administrating to a subject in need, an effective amount of a compound as described in (1),

(33) A method for preventing or treating disorders of micturition in mammals which comprises administrating to a subject in need an effective amount of a compound as described in (1),

(34) A method for preventing or treating disorders of asthma, migraine, irritable bowel syndrome, pain, cough or emesis in mammals which comprises administrating to a subject in need an effective amount of a compound as described in (1),

(35) Use of a compound as described in (1) for manufacturing a composition for antagonizing a tachykinin receptor,

(36) Use of a compound as described in (1) for manufacturing a pharmaceutical composition for treating disorders of micturition, and

(37) Use of a compound as described in (1) for manufacturing a pharmaceutical composition for treating disorders of asthma, micturition, irritable bowel syndrome, pain, cough or emesis.

The compounds of the above-mentioned (1) include compounds of a formula (Ia):

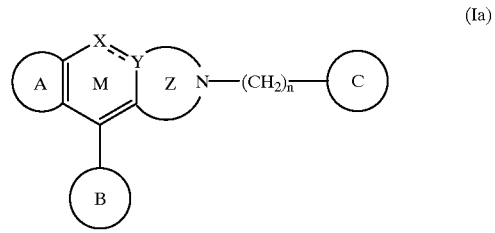

(Ia)

wherein ring A is formed by $R^a$ and $R^b$ are bonded to each other to form Ring A, and the other symbols have the same meanings as above.

The present invention is described in detail hereinunder.

Regarding "Ring M, X and Y"

In the above-mentioned formulae (I) and (Ia), Ring M is a heterocyclic ring having —N=C<, —CO—N< or —CS—N< as the partial structure "—X⋯⋯Y<". Preferably, Ring M has —CO—N< or —N=C— as the partial structure "—X⋯⋯Y<".

Regarding "$R^a$ and $R^b$"

In the above-mentioned formulae (I) and (Ia), $R^a$ and $R^b$ are bonded to each other to form Ring A, or these are the same or different and represent, independently, a hydrogen atom or a substituent on the Ring M.

The substituents $R^a$ and $R^b$ on the Ring M include, for example, a halogen atom, an optionally substituted alkyl group, an optionally halogenated alkoxy group, an optionally halogenated alkylthio group, a cycloalkyl group, an aryl group, an acylamino group, an acyloxy group, a hydroxyl group, a nitro group, a cyano group, an amino group, a mono- or di-alkylamino group, a cyclic amino group (e.g., a cyclic amino group optionally containing hetero atom(s) of oxygen atom, sulfur atom, etc., in addition to nitrogen atom), an alkylcarbonylamino group, an alkylsulfonylamino group, an alkoxycarbonyl group, a carboxyl group, an alkylcarbonyl group, a carbamoyl group, a mono- or di-alkylcarbamoyl group, an alkylsulfonyl group, an oxo group, etc.

The above-mentioned "halogen atom" includes, for example, fluorine, chlorine, bromine and iodine atoms. Preferably, the halogen atom includes, for example, fluorine, chlorine and bromine atoms.

The "optionally substituted alkyl group" includes, for example, $C_{1-6}$ alkyl groups (e.g., methyl, ethyl, propyl, isopropyl, butyl, isobutyl, sec-butyl and tert-butyl groups, etc.) optionally having from 1 to 5 substituents selected from a hydroxyl group, a $C_{1-6}$ alkoxy group (e.g., methoxy, ethoxy, propoxy, butoxy, isobutoxy, sec-butoxy, tert-butoxy, etc.), a $C_{1-6}$ alkylthio group (e.g., methylthio, ethylthio, propylthio, butylthio, isobutylthio, sec-butyltio, tert-butyltio, etc.), an amino group, a $C_{1-7}$ acylamino group (e.g. formylamino, acethyl amino, propyonyl amino, butylyl amino, benzoyl amino, etc.), an N-alkylamino group, a carboxyl group, a nitro group, a mono- or di-$C_{1-6}$ alkylamino group (e.g., methylamino, ethylamino, dimethylamino and diethylamino groups, etc.), an optionally substituted N-substituted amino group substituted by one or two homocyclic groups (e.g., mono- or di-$C_{3-8}$ cycloalkylamino groups, for example, cyclopropylamino, cyclobutylamino, cyclohexylamino; $C_{6-10}$ arylamino groups, for example, phenylamino, etc.), an optionally substituted heterocyclic groups [e.g., 5-membered to 9-membered cycloamino groups which may have 1 to 3 hetero atoms selected from nitrogen, oxygen and sulfur atoms (e.g., 5-membered or 6-membered non-aromatic cycloamino groups, for example, piperidyno, 4-methylpiperodyno, morpholino, thiomorpholino, piperadinyl, 4-methylpiperadinyl, 4-ethylpiperadinyl, pyrrolidinyl, imidazolydinyl, pyrazolydinyl; 5-membered or 6-membered aromatic cycloamino groups, for example, pyridyl, pyradyl, pyrimidinyl, pyridazinyl, pyrrolyl, imidazolyl, pyrazulyl, etc.), aromatic heterocyclic rings (e.g., thiophenyl, furanyl, thiazolyl, isothiazolyl, oxazolyl, etc.), non-aromatic heterocyclic rings (e.g., tetrohydropyridyl, dihydropyridyl, tetrahydropyradyl, tetrahydropyrimidinyl, tetrahydropyridazinyl, dihydropyranyl, dihydropyrrolyl, dyhydroimidazolyl, dihydropyrazolyl, dihydrothiophenyl, dihydrofuranyl, dihydrooxazolyl, dihydroisooxazolyl, hexahydropyrimidinyl, hexahydropyridazinyl, tetrahydropyranyl, pyrazolydinyl, tetrahydrothiophenyl, tetrahydrofuranyl, tetrahydrothiazolyl, tetrahydroisothiazolyl, tetrahydrooxazolyl, tetrahydroisooxazolyl, etc.)], an alkylsulfonylamino groups (e.g. $C_{1-4}$ alkylsulfonylamino groups, for example, methylsulfonylamino, ethylsulfonylamino, etc.), a $C_{1-6}$ alkyl-carbonyloxy group (e.g., acetoxy and ethylcarbonyloxy groups, etc.) and a halogen atom (e.g., fluorine, chlorine and bromine atoms, etc.), etc. Preferably, the "optionally substituted alkyl group" includes $C_{1-6}$ alkyl groups optionally substituted by from 1 to 4 or so halogen atoms, especially optionally halogenated $C_{1-4}$ alkyl groups (e.g., $C_{1-4}$ alkyl groups and $C_{1-4}$ alkyl groups substituted by from 1 to 3 or so halogen atoms, etc., such as methyl, chloromethyl, fluoromethyl, difluoromethyl, trichloromethyl, trifluoromethyl, ethyl, 2-bromoethyl, 2,2,2-trichloroethyl, 2,2,2-trifluoroethyl, pentafluoroethyl, propyl, 3,3,3-trifluoropropyl, isopropyl, 1-(trifluoromethyl)ethyl, butyl, 4,4,4-trifluorobutyl, isobutyl, sec-butyl and tert-butyl groups, etc.). Also preferably, the "optionally-substituted alkyl group" includes $C_{1-6}$ alkoxy-$C_{1-6}$ alkyl groups (e.g. $C_{1-4}$ alkoxy-$C_{1-4}$ alkyl groups, for example, methoxymethyl, ethoxymethyl, isopropoxymethyl, butoxymethyl, methoxyethyl, ethoxyethyl, etc.), $C_{1-6}$ alkyltho-$C_{1-6}$ alkyl groups (e.g. $C_{1-4}$ alkylthio-$C_{1-4}$ alkyl groups, for example, methylthiomethyl, ethylthiomethyl, butylthiomethyl, methylthioethyl, ethylthioethyl, etc.), amino-$C_{1-6}$ alkyl groups (preferably, amino-$C_{1-4}$ alkyl groups), for example, aminomethyl, 2-aminoethyl, 2-aminopropyl, 3-aminopropyl, 2-aminobutyl, 3-aminobutyl and 4-aminobutyl groups, $C_{1-7}$ acylamino-$C_{1-6}$ alkyl groups (e.g. $C_{1-7}$ acylamino-$C_{1-4}$ alkyl groups, for example, formylaminomethyl, acetylaminomethyl, propionylaminomethyl, butylylaminoethyl, benzoylaminomethyl, etc.), etc. And, again, the "optionally-substituted alkyl group" preferably includes mono-$C_{1-4}$ alkylamino-$C_{1-6}$ alkyl groups, for example, mono-$C_{1-3}$ alkylamino-$C_{1-4}$ alkyl groups, etc., such as methylaminomethyl, ethylaminomethyl, 2-(N-methylamino)ethyl, 2-(N-ethylamino)ethyl, 2-(N-methylamino)propyl, 3-(N-methylamino)propyl, 3-(N-methylamino)butyl and 4-(N-methylamino)butyl groups, $C_{3-10}$ cycloalkylamino-$C_{1-6}$ alkyl groups (e.g. $C_{3-10}$ cycloalkylamino-$C_{1-4}$ alkyl groups, for example, cyclopropylaminomethyl, cyclobutylaminomethyl, cyclohexylaminomethyl, cyclopropylaminomethyl, cyclobutylaminomethyl, cyclohexylaminomethyl, phenylaminomethyl, etc.), optionally having 1 to 3 hetero atoms selected from nitrogen, oxygen and sulfur atoms 5-membered or 6-membered non-aromatic cycloamino-$C_{1-6}$ alkyl groups (e.g. 5-membered or 6-membered non-aromatic cycloamino-$C_{1-4}$ alkyl groups, for example, piperidinomethyl, 4-methylpiperidinomethyl, morpholinomethyl, thiomorpholinomethyl, piperadinylmethyl, 4-methylpiperadinylmethyl, piperidinoethyl, morpholinoethyl, piperadinylethyl; 5-membered or 6-membered aromatic cycloamino-$C_{1-4}$ alkyl groups, for example, pyridylmethyl, pyrimidinylmethyl, imidazolylmethyl, pyridylethyl, etc.), $C_{1-6}$ alkylsulfonylamino-$C_{1-6}$ alkyl groups (e.g. $C_{1-6}$ alkylsulfonylamino-$C_{1-4}$ alkyl groups, for example, methylsulfonylaminomethyl, ethylsulfonylaminomethyl, methylsulfonylaminobutyl, ethylsulfonylaminoethyl, etc.), $C_{1-6}$ alkyl-carbonyloxy-$C_{1-6}$ alkyl groups (e.g. $C_{1-4}$ alkyl-carbonyloxy-$C_{1-4}$ alkyl groups, for example, methylcarbonyloxymethyl, ethylcarbonyloxymethyl, butylcarbonyloxymethyl, methylcarbonyloxyethyl, ethylcarbonyloxyethyl, etc.), etc.

The "optionally halogenated alkoxy group" includes, for example, $C_{1-6}$ alkoxy groups or $C_{1-6}$ alkoxy groups substituted by from 1 to 5 or so halogen atoms, etc. Such alkoxy groups or halogenated alkoxy groups include, for example, methoxy, fluoromethoxy, difluoromethoxy, trifluoromethoxy, trichloromethoxy, ethoxy, 2,2,2-trifluoroethoxy, 2,2,2-trichloroethoxy, pentafluoroethoxy, propoxy, isopropoxy, butoxy, 4,4,4-trifluorobutoxy, isobutoxy, sec-butoxy, pentoxy and hexyloxy groups, etc. Preferably, the "optionally-halogenated alkoxy group" includes $C_{1-4}$ alkoxy groups or $C_{1-4}$ alkoxy group substituted by from 1 to 3 or so halogen atoms, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy groups, etc.

The "optionally halogenated alkylthio group" includes, for example, $C_{1-6}$ alkylthio groups, and $C_{1-6}$ alkylthio groups having from 1 to 5 or so halogen atoms, etc. Such alkylthio groups and halogenated alkylthio groups include, for example, methylthio, difluoromethylthio, trifluoromethylthio, ethylthio, propylthio, isopropylthio, butylthio, 4,4,4-trifluorobutylthio, pentylthio and hexylthio groups, etc. Preferably, the "optionally halogenated alkylthio group" includes $C_{1-4}$ alkylthio groups, or $C_{1-4}$ alkylthio groups substituted by from 1 to 3 or so halogen atoms, for example, methylthio, difluoromethylthio, trifluoromethylthio, ethylthio, propylthio, isopropylthio, butylthio and 4,4,4-trifluorobutylthio groups, etc.

The "cycloalkyl group" includes $C_{3-10}$ cycloalkyl groups (e.g., cyclopropyl, cyclobutyl, cyclopentyl, cyclohexyl and cyclooctyl groups, etc.); the "aryl group" includes $C_{6-10}$ aryl groups (e.g., phenyl group, etc.); the "acylamino group" includes, for example, $C_{1-7}$ acylamino groups (e.g., formylamino, acetylamino, propionylamino, butyrylamino and benzoylamino groups, etc.), etc. The "acyloxy group" includes, for example, $C_{1-3}$ acyloxy groups (e.g., formyloxy, acetoxy and propionyloxy groups, etc.), etc. The "mono- or di-alkylamino group" includes, for example, mono- or di-$C_{1-4}$ alkylamino groups (e.g., methylamino, ethylamino, propylamino, dimethylamino and diethylamino groups, etc.), etc. The "cyclic amino group" includes, for example, 5-membered to 9-membered cyclic amino groups optionally having from 1 to 3 hetero atoms, such as oxygen atom, sulfur atom, etc., in addition to nitrogen atom (e.g., pyrrolidino, piperidino, morpholino and thiomorpholino groups, etc.), etc. The "alkylcarbonylamino group" includes, for example, $C_{1-4}$ alkyl-carbonylamino groups (e.g., acetylamino, propionylamino and butyrylamino groups, etc.); the "alkylsulfonylamino group" includes, for example, $C_{1-4}$ alkylsulfonylamino groups (e.g., methylsulfonylamino and ethylsulfonylamino groups, etc.); the "alkoxycarbonyl group" includes, for example, $C_{1-4}$ alkoxy-carbonyl groups (e.g., methoxycarbonyl, ethoxycarbonyl, propoxycarbonyl and butoxycarbonyl groups, etc.); the "alkylcarbonyl group" includes, for example, $C_{1-6}$ alkyl-carbonyl groups (e.g., methylcarbonyl, ethylcarbonyl and propylcarbonyl groups, etc.); the "mono- or di-alkylcarbamoyl group" includes for example, mono- or di-$C_{1-4}$ alkylcarbamoyl groups (e.g., methylcarbamoyl, ethylcarbamoyl, dimethylcarbamoyl and diethylcarbamoyl groups, etc.); the "alkylsulfonyl group" includes, for example, $C_{1-6}$ alkylsulfonyl groups (e.g., methylsulfonyl, ethylsulfonyl and propylsulfonyl groups, etc.), etc.

Regarding "Ring A and Ring B"

In the above-mentioned formulae (I) and (Ia), Ring A and Ring B represent, independently, an optionally substituted homocyclic or heterocyclic ring, and at least one of these is an optionally substituted heterocyclic ring.

The "homocyclic or heterocyclic ring" includes, for example, (i) an aromatic heterocyclic ring or non-aromatic heterocyclic ring having the same one or different hetero atoms selected from nitrogen, sulfur and oxygen atoms, preferably from 1 to 3 such hetero atoms, in addition to carbon atoms, or (ii) a cyclic hydrocarbon ring (homocyclic ring) comprising carbon atoms, etc.

The "aromatic heterocyclic ring" includes, for example, 5-membered or 6-membered aromatic heterocyclic rings having from 1 to 3 hetero atoms selected from nitrogen, oxygen and sulfur atoms, in addition to carbon atoms (e.g., pyridine, pyrazine, pyrimidine, pyridazine, pyrrole, imidazole, pyrazole, triazole, thiophene, furan, thiazole, isothiazole, oxazole and isoxazole rings, etc.), etc. Preferably, the aromatic heterocyclic ring includes, for example, pyridine, pyrazine and thiophene rings, etc., as well as pyrrole and thiazole rings, etc. Especially preferred are (i) 6-membered, nitrogen-containing heterocyclic rings having one or two nitrogen atoms in addition to carbon atoms (e.g., pyridine and pyrazine rings, etc.) or (ii) 5-membered aromatic heterocyclic rings having one sulfur atom in addition to carbon atoms (e.g., thiophene ring, etc.), etc.

The "non-aromatic heterocyclic ring" includes, for example, 5-membered to 9-membered, non-aromatic heterocyclic rings, preferably 5-membered or 6-membered, non-aromatic heterocyclic rings, having from 1 to 3 hetero atoms selected from nitrogen, oxygen and sulfur atoms in addition to carbon atoms, etc.

For example, Ring A includes tetrahydropyridine, dihydropyridine, tetrahydropyrazine, tetrahydropyrimidine, tetrahydropyridazine, dihydropyran, dihydropyrrole, dihydroimidazole, dihydropyrazole, dihydrothiophene, dihydrofuran, dihydrothiazole, dihydroisothiazole, dihydroxazole and dihydroisoxazole rings, etc.; and Ring A includes, in addition to these rings, piperidine, piperazine, hexahydropyrimidine, hexahydropyridazine, tetrahydropyran, morpholine, pyrrolidine, imidazolidine, pyrazolidine, tetrahydrothiophene, tetrahydrofuran, tetrahydrothiazole, tetrahydroisothiazole, tetrahydroxazole and tetrahydroisoxazole rings, etc. Preferably, Ring A includes, for example, 6-membered, non-aromatic heterocyclic rings having one or two nitrogen atoms in addition to carbon atoms (e.g., tetrahydropyridine, tetrahydropyrimidine and tetrahydropyridazine rings, etc.), etc., and is especially preferably a tetrahydropyridine ring, etc. Preferably, Ring B includes, for example, 6-membered, non-aromatic heterocyclic rings having one or 2 nitrogen atoms in addition to carbon atoms (e.g., piperidine and piperazine rings, etc.), etc., and is especially preferably a piperazine ring, etc.

The "cyclic hydrocarbon ring (homocyclic ring)" includes, for example, 3-membered to 10-membered (for example, 5-membered to 9-membered) cyclic hydrocarbon rings, preferably 5-membered or 6-membered cyclic hydrocarbon rings, etc. For example, Ring A includes benzene, $C_{3-10}$ cycloalkenes (e.g., cyclobutene, cyclopentene, cyclohexene, cycloheptene, cyclooctene, etc.), etc. The cycloalkenes are preferably $C_{5-6}$ cycloalkenes (e.g., cyclopentene, cyclohexene, etc.), etc. Ring B includes, in addition to these, $C_{3-10}$ cycloalkanes (e.g., cyclobutane, cyclopentane, cyclohexane, cycloheptane, cyclooctane, etc.), etc. The cycloalkanes are preferably $C_{5-6}$ cycloalkanes (e.g., cyclohexane, cyclopentane, etc.), etc. Preferably, Ring A includes, for example, 6-membered homocyclic rings such as benzene and cyclohexene rings, etc. Especially preferred are a benzene ring, etc. Ring B preferably includes, for example, 6-membered homocyclic rings such as benzene and cyclohexane rings, etc. Especially preferred is a benzene ring.

At least one of Ring A and Ring B is an optionally-substituted heterocyclic ring. Both of Ring A and Ring B may be optionally substituted heterocyclic rings. Preferably, one of Ring A and Ring B is 1) an optionally substituted aromatic ring and the other is 2) an optionally substituted aromatic heterocyclic ring.

The above-mentioned 1) "aromatic ring" includes, for example, (i) the above-mentioned "aromatic heterocyclic rings", namely, optionally substituted, 5-membered or 6-membered, aromatic heterocyclic rings having the same one or different two hetero atoms selected from nitrogen, sulfur and oxygen atoms, preferably from 1 to 3 such hetero atoms, in addition to carbon atoms (e.g., pyridine, pyrazine, pyrimidine, pyridazine, pyrrole, imidazole, pyrazole, triazole, thiophene, furan, thiazole, isothiazole, oxazole and isoxazole rings, etc.), or (ii) optionally substituted benzene rings.

For the substituents for the above-mentioned 1) "optionally substituted aromatic ring", for example, referred to are the same substituents as those for Ring A and Ring B which are mentioned hereinunder. The "aromatic heterocyclic ring" of the above-mentioned 2) "optionally substituted aromatic heterocyclic ring" includes, for example, the same aromatic heterocyclic rings as those in the above-mentioned "5-membered or 6-membered, aromatic heterocyclic ring". For the substituents for the above-mentioned 2) "optionally substituted aromatic heterocyclic ring", for example, referred to are the same substituents as those for Ring A and Ring B which are mentioned hereinunder. The "5-membered or 6-membered, aromatic heterocyclic ring" preferably includes the same heterocyclic rings as those referred to hereinabove for the foregoing "aromatic heterocyclic ring".

More preferably, one of Ring A and Ring B is an optionally substituted aromatic heterocyclic ring (e.g., a 5-membered or 6-membered aromatic heterocyclic ring) and the other is an optionally substituted benzene ring.

The substituents for the optionally substituted "homocyclic or heterocyclic ring", "aromatic heterocyclic ring", "non-aromatic heterocyclic ring", "cyclic hydrocarbon ring", "aromatic ring" and "benzene ring" to be represented by Ring A and Ring B include, for example, a halogen atom, an optionally substituted alkyl group, an optionally halogenated alkoxy group, an optionally halogenated alkylthio group, an aryl group, an acylamino group, an acyloxy group, a hydroxyl group, a nitro group, a cyano group, an amino group, a mono- or di-alkylamino group, a cyclic amino group (e.g., a cyclic amino group optionally having hetero atom selected from oxygen atom, sulfur atom, etc., in addition to nitrogen atom), an alkylcarbonylamino group, an alkylsulfonylamino group, an alkoxycarbonyl group, a carboxyl group, an alkylcarbonyl group, a carbamoyl group, a mono- or di-alkylcarbamoyl group, an alkylsulfonyl group, an oxo group, etc.

The "halogen atom", which Ring A and Ring B may have, includes, for example, fluorine, chlorine, bromine and iodine atoms. Preferably, the halogen atom includes, for example, fluorine, chlorine and bromine atoms (especially, fluorine and chlorine atoms, etc.).

The "optionally substituted alkyl group", which Ring A and Ring B may have, includes, for example, $C_{1-6}$ alkyl groups (e.g., methyl, ethyl, propyl, isopropyl, butyl, isobutyl, sec-butyl and tert-butyl groups, etc.) optionally having from 1 to 5 substituents selected from a hydroxyl group, an amino group, a carboxyl group, a nitro group, a mono- or di-$C_{1-6}$ alkylamino group (e.g., methylamino, ethylamino, dimethylamino and diethylamino groups, etc.), a $C_{1-6}$ alkyl-carbonyloxy group (e.g., acetoxy and ethylcarbonyloxy groups, etc.) and a halogen atom (e.g., fluorine, chlorine and bromine atoms, etc.), etc. Especially preferred are optionally-halogenated alkyl groups, for example, $C_{1-6}$ alkyl groups, and $C_{1-6}$ alkyl groups substituted by from 1 to 4 or so halogen atoms, etc. Such alkyl groups and halogenated alkyl groups include, for example, methyl, chloromethyl, fluoromethyl, difluoromethyl, trichloromethyl, trifluoromethyl, ethyl, 2-bromoethyl, 2,2,2-trichloroethyl, 2,2,2-trifluoroethyl, pentafluoroethyl, propyl, 3,3,3-trifluoropropyl, isopropyl, 1-(trifluoromethyl)ethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl and 5-trifluoromethylpentyl groups, etc.

More preferably, the "optionally substituted alkyl group" includes optionally halogenated $C_{1-4}$ alkyl groups, for example, $C_{1-4}$ alkyl groups and $C_{1-4}$ alkyl groups substituted by from 1 to 3 or so halogen atoms, etc., such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl and tert-butyl groups, etc.

The "optionally halogenated alkoxy group", which Ring A and Ring B may have, includes, for example, $C_{1-6}$ alkoxy groups or $C_{1-6}$ alkoxy groups substituted by from 1 to 5 or so halogen atoms such as those mentioned hereinabove, etc. Such alkoxy groups or halogenated alkoxy groups include, for example, methoxy, difluoromethoxy, trifluoromethoxy, trichloromethoxy, ethoxy, 2,2,2-trifluoroethoxy, 2,2,2-trichloroethoxy, pentafluoroethoxy, propoxy, isopropoxy, butoxy, 4,4,4-trifluorobutoxy, isobutoxy, sec-butoxy, pentoxy and hexyloxy groups, etc. Preferably, the "optionally halogenated alkoxy group" includes $C_{1-4}$ alkoxy groups or $C_{1-4}$ alkoxy group substituted by from 1 to 3 or so halogen atoms, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy groups, etc.

The "optionally halogenated alkylthio group", which Ring A and Ring B may have, includes, for example, $C_{1-6}$ alkylthio groups, and $C_{1-6}$ alkylthio groups having from 1 to 5 or so halogen atoms such as those mentioned hereinabove, etc. Such alkylthio groups and halogenated alkylthio groups include, for example, methylthio, difluoromethylthio, trifluoromethylthio, ethylthio, propylthio, isopropylthio, butylthio, 4,4,4-trifluorobutylthio, pentylthio and hexylthio groups, etc. Preferably, the "optionally halogenated alkylthio group" includes $C_{1-4}$ alkylthio groups, or $C_{1-4}$ alkylthio groups substituted by from 1 to 3 or so halogen atoms, for example, methylthio, difluoromethylthio, trifluoromethylthio, ethylthio, propylthio, isopropylthio, butylthio and 4,4,4-trifluorobutylthio groups, etc.

The aryl group as the substituent includes $C_{6-10}$ aryl groups (e.g., phenyl group, etc.); the acylamino group includes, for example, $C_{1-7}$ acylamino groups (e.g., formylamino, acetylamino, propionylamino, butyrylamino and benzoylamino groups, etc.), etc. The acyloxy group includes, for example, $C_{1-3}$ acyloxy groups (e.g., formyloxy, acetoxy and propionyloxy groups, etc.), etc. The mono- or di-alkylamino group includes, for example, mono- or di-$C_{1-4}$ alkylamino groups (e.g., methylamino, ethylamino, propylamino, dimethylamino and diethylamino groups, etc.), etc. The cyclic amino group includes, for example, 5-membered to 9-membered cyclic amino groups optionally having from 1 to 3 hetero atoms, such as oxygen atom, sulfur atom, etc., in addition to nitrogen atom (e.g., pyrrolidino, piperidino and morpholino groups, etc.), etc. The alkylcarbonylamino group includes, for example, $C_{1-4}$ alkylcarbonylamino groups (e.g., acetylamino, propionylamino and butyrylamino groups, etc.); the alkylsulfonylamino group includes, for example, $C_{1-4}$ alkylsulfonylamino groups (e.g., methylsulfonylamino and ethylsulfonylamino groups, etc.); the alkoxycarbonyl group includes, for example, $C_{1-4}$ alkoxy-carbonyl groups (e.g., methoxycarbonyl, ethoxycarbonyl, propoxycarbonyl and butoxycarbonyl groups, etc.); the alkylcarbonyl group includes, for example, $C_{1-6}$ alkyl-carbonyl groups (e.g., methylcarbonyl, ethylcarbonyl and propylcarbonyl groups, etc.); the mono- or di-alkylcarbamoyl group includes, for example, mono- or di-$C_{1-4}$ alkylcarbamoyl groups (e.g., methylcarbamoyl, ethylcarbamoyl, dimethylcarbamoyl and diethylcarbamoyl groups, etc.); the alkylsulfonyl group includes, for example, $C_{1-6}$ alkylsulfonyl groups (e.g., methylsulfonyl, ethylsulfonyl and propylsulfonyl groups, etc.), etc.

The terminology "optionally halogenated" as referred to herein means that the number of halogen atoms, if substituted, is from 1 to 5, preferably from 1 to 3 or so.

Preferred substituents for the optionally substituted Ring A and Ring B include a halogen atom, an optionally halogenated $C_{1-4}$ alkyl group, an optionally halogenated $C_{1-4}$ alkoxy group, an optionally halogenated $C_{1-4}$ alkylthio group, a $C_{1-3}$ acyloxy group, a hydroxyl group, an amino group, a mono- or di-$C_{1-4}$ alkylamino group, a carboxyl group, a $C_{1-4}$ alkoxy-carbonyl group, an oxo group, etc.

More preferred substituents for the optionally substituted Ring A and Ring B include a halogen atom, an optionally halogenated $C_{1-4}$ alkyl group, an optionally halogenated $C_{1-4}$ alkoxy group, a hydroxyl group, an amino group, a mono- or di-$C_{1-4}$ alkylamino group, a $C_{1-3}$ acyloxy group, an oxo group, etc. Especially preferred are a halogen atom, an optionally halogenated $C_{1-4}$ alkyl group, an optionally halogenated $C_{1-4}$ alkoxy group, etc.

The substituents for Ring A and Ring B, if any, may be at any substitutable position. If the rings are substituted by two or more substituents, the substituents may be the same or different. The number of the substituents may be from 1 to 4 or so, preferably from 1 to 3 or so.

If the Ring A and/or the Ring B has nitrogen atom(s), the ring may form a quaternary salt. For example, it may form a salt with halide ion(s) (e.g., Cl⁻, Br⁻, I⁻, etc.) or other anion(s) such as sulfato ion, hydroxyl ion, etc.

Regarding "Ring A"

Preferred homocyclic rings for Ring A are optionally substituted homocyclic rings composed of carbon atoms, for example, including those of a formula (A-1):

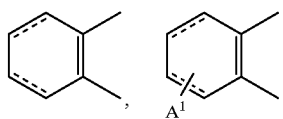

(A-1)

wherein ..... indicates a single bond or a double bound and the same shall apply hereinunder; and $A^1$ represents a halogen atom (e.g., fluorine and chlorine atoms, etc.), an optionally-halogenated $C_{1-4}$ alkyl group (e.g., methyl, isopropyl, trifluoromethyl, trichloromethyl, ethyl, 2,2,2-trifluoroethyl and pentafluoroethyl groups, etc.), or an optionally halogenated $C_{1-4}$ alkoxy group (e.g., methoxy, trifluoromethoxy, trichloromethoxy, ethoxy, 2,2,2-trifluoroethoxy and pentafluoroethoxy groups, etc.); or those of a formula (A-2):

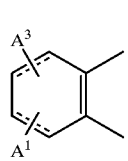

(A-2)

wherein $A^2$ and $A^3$ are the same or different and represent, independently, a halogen atom (e.g., fluorine and chlorine atoms, etc.), an optionally halogenated $C_{1-4}$ alkyl group (e.g., methyl, isopropyl, trifluoromethyl, trichloromethyl, ethyl, 2,2,2-trifluoroethyl and pentafluoroethyl groups, etc.), or an optionally halogenated $C_{1-4}$ alkoxy group (e.g., methoxy, trifluoromethoxy, trichloromethoxy, ethoxy, 2,2,2-trifluroroethoxy and pentafluoroethoxy groups, etc.).

More preferred homocyclic rings include, for example, benzene rings of a formula (A-3):

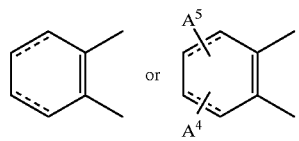

(A-3)

wherein $A^4$ and $A^5$ are the same or different and represent, independently, a halogen atom (e.g., fluorine and chlorine atoms, etc.), or an optionally-halogenated $C_{1-4}$ alkyl group (e.g., methyl, trifluoromethyl, trichloromethyl, ethyl, 2,2,2-trifluoroethyl, pentafluoroethyl and isopropyl groups, etc.).

Also preferred are optionally substituted benzene rings of a formula (A-4):

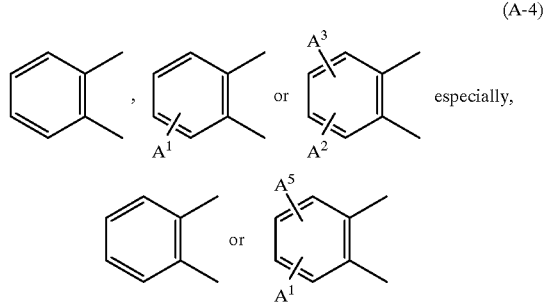

(A-4)

wherein the symbols have the same meanings as above.

Of the homocyclic rings of the above-mentioned formulae, especially preferred are those as substituted by the following substituent(s):

(1) Homocyclic rings where $A^1$ is a halogen atom (e.g., fluorine and chlorine atoms, etc.), or an optionally-substituted $C_{1-4}$ alkyl group (e.g., methyl, trifluoromethyl, ethyl and isopropyl groups, etc.).

(2) Homocyclic rings where $A^2$ and $A^3$ are the same or different and represent, independently, an optionally-halogenated $C_{1-4}$ alkyl group (e.g., methyl, trifluoromethyl, ethyl and isopropyl groups, etc.), or an optionally-halogenated $C_{1-4}$ alkoxy group (e.g., methoxy, trifluoromethoxy and ethoxy groups, etc.).

(3) Homocyclic rings where $A^4$ and $A^5$ are the same or different and represent, independently, a $C_{1-4}$ alkyl group (e.g., methyl, ethyl and isopropyl groups, etc.).

(4) Homocyclic rings where $A^1$ is a halogen atom (e.g., fluorine and chlorine atoms, etc.).

(5) Homocyclic rings where $A^2$ and $A^3$ are the same or different and represent, independently, a $C_{1-4}$ alkoxy group (e.g., methoxy and ethoxy groups, etc.).

Preferred aromatic heterocyclic or non-aromatic heterocyclic rings for Ring A are 5-membered or 6-membered, aromatic heterocyclic or non-aromatic heterocyclic rings including, for example, pyridine, pyrazine, thiophene, tetrahydropyridine, pyrrole and thiazole rings, etc. Concretely, for example, preferred are heterocyclic rings of a formula (A-5):

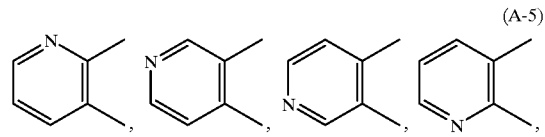

(A-5)

-continued

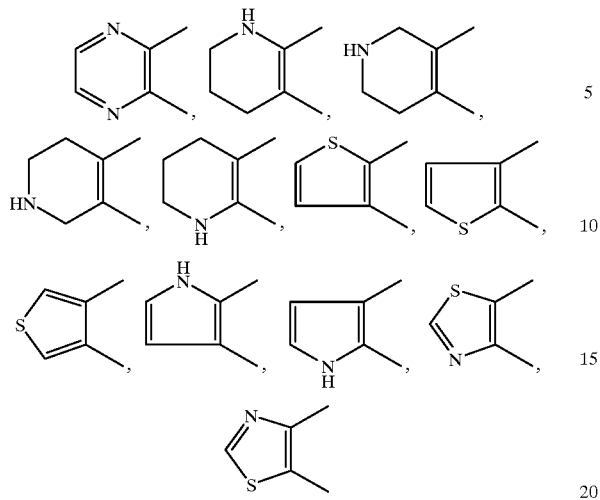

As preferred examples of optionally substituted aromatic or non-aromatic heterocyclic rings for Ring A, mentioned are pyridine, pyrazine, thiophene, tetrahydropyridine, pyrrole and thiazole rings, etc. optionally having one or two substituents selected from an oxo group, an optionally substituted alkyl group (this has the same meaning as the substituent for the optionally substituted Ring A and Ring B), a $C_{6-10}$ aryl group (e.g., phenyl group, etc.) and a halogen atom (e.g., fluorine, chlorine and bromine atoms, etc.). Concretely, for example, preferred are aromatic or non-aromatic heterocyclic rings of a formula (A-6):

(A-6)

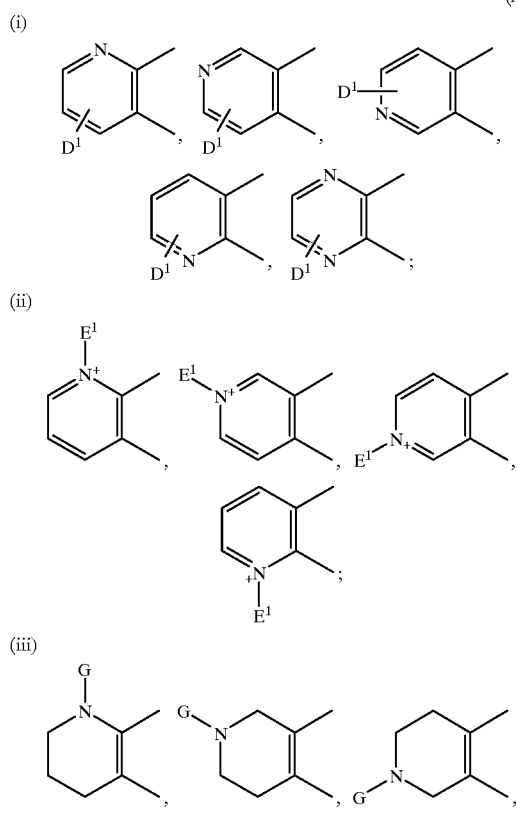

(i)

(ii)

(iii)

-continued (iv)

(v)

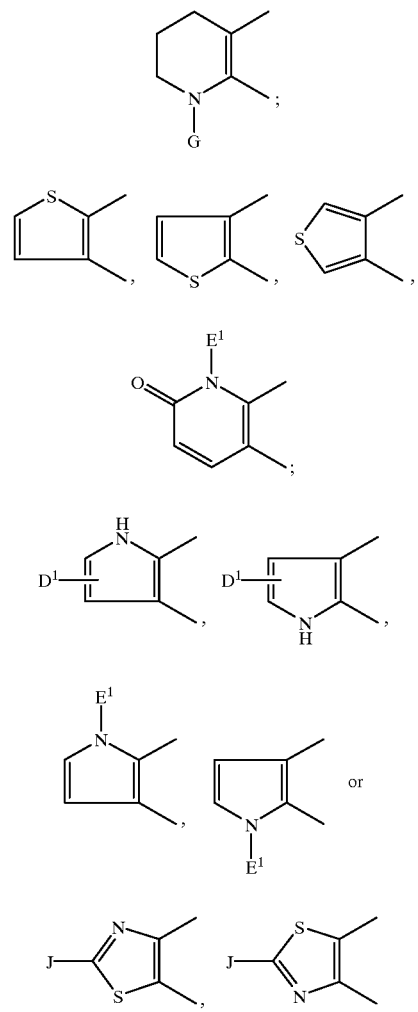

(vi)

(vii)

(viii)

wherein $D^1$ represents a hydrogen atom, a halogen atom (e.g., fluorine, chlorine and bromine atoms, etc.); $E^1$ represents a $C_{1-4}$ alkyl group (e.g., methyl, ethyl, propyl and isopropyl groups, etc.); the compounds having the partial structure of (ii) form quaternary ammonium salts along with a halide ion (e.g., $Cl^-$, $Br^-$, $I^-$, etc.), a sulfato ion, a hydroxyl ion or the like; G represents a hydrogen atom or a $C_{1-4}$ alkyl group (e.g., methyl, ethyl, propyl and isopropyl groups, etc.); J represents a hydrogen atom, a $C_{1-4}$ alkyl group (e.g., methyl, ethyl, propyl and isopropyl groups, etc.) or a $C_{6-10}$ aryl group (e.g., phenyl group, etc.).

More preferably, ring A is a pyridine ring which may be substituted by 1 to 3 substituents selected from a halogen atom or $C_{1-4}$ alkyl group.

Ring A is preferably a 5-membered or a 6-membered, nitrogen-containing heterocyclic ring, for example, (i) a 6-membered, aromatic, nitrogen-containing heterocyclic ring having one or two nitrogen atoms in addition to carbon atoms (e.g., pyridine and pyrazine rings, etc.), (ii) a 6-membered, non-aromatic heterocyclic ring having one or two nitrogen atoms in addition to carbon atoms (e.g., tetrahydropyridine, tetrahydropyrimidine and tetrahydropyridazine rings, etc.), or the like. Especially preferably, Ring A is an aromatic, nitrogen-containing heterocyclic ring, particularly, a pyridine ring or the like.

Regarding "Ring B"

Preferred homocyclic rings for Ring B are optionally substituted homocyclic rings composed or carbon atoms, for example, including those of a formula (B-1):

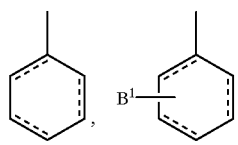
(B-1)

wherein $B^1$ represents a halogen atom, an optionally halogenated $C_{1-4}$ alkyl group or an optionally halogenated $C_{1-4}$ alkoxy group; those of a formula (B-2):

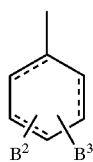
(B-2)

wherein $B^2$ and $B^3$ are the same or different and represent, independently, a halogen atom, an optionally halogenated $C_{1-4}$ alkyl group or an optionally halogenated $C_{1-4}$ alkoxy group; and those of a formula (B-3):

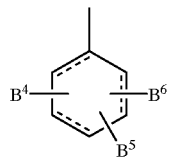
(B-3)

wherein $B^4$, $B^5$ and $B^6$ are the same or different and represent, independently, a halogen atom, an optionally halogenated $C_{1-4}$ alkyl group or an optionally halogenated $C_{1-4}$ alkoxy group.

More preferred are homocyclic rings of a formula (B-4):

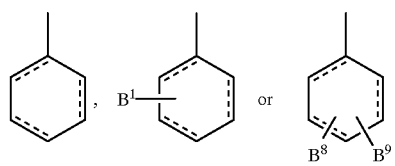
(B-4)

wherein $B^7$, $B^8$ and $B^9$ are the same or different and represent, independently, a halogen atom, an optionally halogenated $C_{1-4}$ alkyl group or an optionally halogenated $C_{1-4}$ alkoxy group.

Even more preferred are homocyclic rings of a formula (B-5):

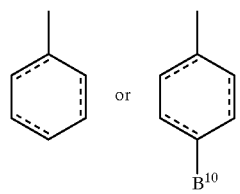
(B-5)

wherein $B^{10}$ represents, a halogen atom, an optionally halogenated $C_{1-4}$ alkyl group or an optionally halogenated $C_{1-4}$ alkoxy group.

In the above-mentioned formulae, the halogen atom for any of $B^1$ to $B^{10}$ includes, for example, fluorine, chlorine and bromine atoms, etc.; the optionally-halogenated $C_{1-4}$ alkyl group includes, for example, methyl, trifluoromethyl, trichloromethyl, ethyl, 2,2,2-trifluoroethyl, 2,2,2-trichloroethyl, 1,1,2,2-tetrafluoroethyl, pentafluoroethyl, propyl, 2,2,3,3-tetrafluoropropyl and isopropyl groups, etc.; and the optionally-halogenated $C_{1-4}$ alkoxy group includes, for example, methoxy, trifluoromethoxy, trithloromethoxy, ethoxy, 2,2,2-trifluoroethoxy, 2,2,2-trichloroethoxy, 1,1,2,2-tetrafluoroethoxy, pentafluoroethoxy, propoxy, 2,2,3,3-tetrafluoropropoxy and isopropoxy groups, etc.

Ring B is also preferably an optionally substituted benzene ring, which includes, for example, benzene rings of a formula (B-6):

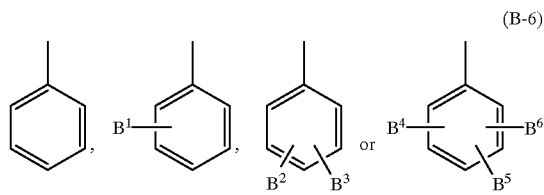
(B-6)

More preferred are benzene rings of a formula (B-7):

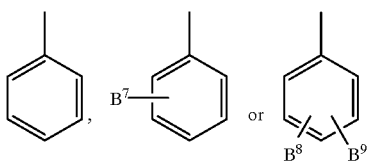
(B-7)

Especially preferred are benzene rings of a formula (B-8):

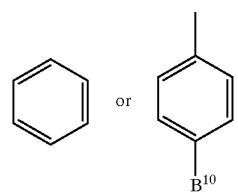
(B-8)

In these formulae, the symbols have the same meanings as above.

Of the substituents in the above-mentioned formulae, for example, especially preferred are the following:

(1) $B^1$, $B^2$, $B^3$, $B^4$, $B^5$ and $B^6$ are the same or different and represent, independently, a halogen atom (e.g., fluorine and chlorine atoms, etc.) or an optionally halogenated $C_{1-4}$ alkyl group (e.g., methyl, trifluoromethyl, ethyl and isopropyl groups, etc.).

(2) $B^1$, $B^2$, $B^3$, $B^4$, $B^5$ and $B^6$ are the same or different and represent, independently, an optionally-halogenated $C_{1-4}$ alkoxy group (e.g., methoxy, trifluoromethoxy and ethoxy groups, etc.).

(3) $B^7$, $B^8$ and $B^9$ represent halogen atoms (e.g., fluorine and chlorine atoms, etc.).

(4) $B^{10}$ represents a fluorine atom.

(5) $B^{10}$ represents a $C_{1-4}$ alkyl group (e.g., methyl group, etc.).

More preferred optionally substituted benzene rings are phenyl groups of a formula (B-9):

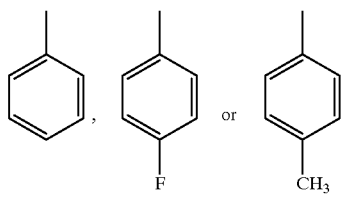

(B-9)

As preferred examples of aromatic heterocyclic rings or non-aromatic heterocyclic rings for Ring B, mentioned are 5-membered or 6-membered aromatic heterocyclic rings or non-aromatic heterocyclic rings such as pyridine, thiophene and piperidine rings, etc. These rings may optionally be substituted by substituents such as those mentioned hereinabove as preferred substituents for Ring A.

Where Ring B is an aromatic heterocyclic ring or a non-aromatic heterocyclic ring, it especially preferably includes, for example, heterocyclic rings of a formula (B-10):

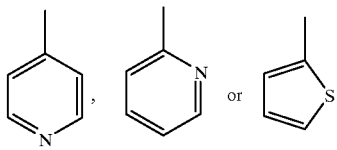

(B-10)

Combination of Ring A and Ring B

Where one or both of Ring A and Ring B is/are heterocyclic ring(s), the ring(s) is/are also preferably unsubstituted one(s).

Preferred combinations of Ring A and Ring B (1) are as follows:

(1) One of Ring A and Ring B is a 5-membered or 6-membered heterocyclic ring having one or two hetero atoms selected from nitrogen and sulfur atoms in addition to carbon atoms (e.g., pyridine, pyrazine, thiophene, tetrahydropyridine, piperidine and piperazine rings, etc.) which may be optionally substituted by $C_{1-4}$ alkyl group(s) (e.g., methyl, ethyl and isopropyl groups, etc.).

One of Ring A and Ring B is a benzene ring optionally substituted by from 1 to 3 substituents selected from a halogen atom (e.g., fluorine, chlorine and bromine atoms, etc.), an optionally halogenated $C_{1-4}$ alkyl group (e.g., methyl, trifluoromethyl, trichloromethyl, ethyl, 2,2,2-trifluoroethyl, pentafluoroethyl, 2,2,2-trichloroethyl, propyl and isopropyl groups, etc.) and an optionally halogenated $C_{1-4}$ alkoxy group (e.g., methoxy, trifluoromethoxy, trichloromethoxy, ethoxy, 2,2,2-trifluoroethoxy, pentafluoroethoxy, 2,2,2-trichloroethoxy, propoxy and isopropoxy groups, etc.).

More preferred combinations of Ring A and Ring B (2) are as follows:

(2) One of Ring A and Ring B is a 5-membered or 6-membered aromatic heterocyclic ring having one or two hetero atoms selected from nitrogen and sulfur atoms in addition to carbon atoms (e.g., pyridine, pyrazine and thiophene rings, etc.).

One of Ring A and Ring B is a benzene ring optionally substituted by from 1 to 3 substituents selected from a halogen atom (e.g., fluorine, chlorine and bromine atoms, etc.), an optionally halogenated $C_{1-4}$ alkyl group (e.g., methyl, trifluoromethyl, trichloromethyl, ethyl, 2,2,2-trifluoroethyl, pentafluoroethyl, 2,2,2-trichloroethyl, propyl and isopropyl groups, etc.) and an optionally halogenated $C_{1-4}$ alkoxy group (e.g., methoxy, trifluoromethoxy, trichloromethoxy, ethoxy, 2,2,2-trifluoroethoxy, pentafluoroethoxy, 2,2,2-trichloroethoxy, propoxy and isopropoxy groups, etc.).

Especially preferably, Ring A is an optionally substituted aromatic heterocyclic ring such as that mentioned above (e.g., an optionally substituted, 5-membered or 6-membered aromatic heterocyclic ring, especially pyridine ring, etc.) while Ring B is an optionally substituted benzene ring.

Regarding "Ring C"

In the above-mentioned formulae (I) and (Ia), Ring C represents an optionally substituted homocyclic ring or an optionally substituted heterocyclic ring. The homocyclic ring or the heterocyclic ring may have from 1 to 5 or so, preferably from 1 to 3 or so substituents, which may be the same or different. The substituents may be positioned at any position of the homocyclic or heterocyclic ring.

The homocyclic ring includes "cyclic hydrocarbon (homocyclic) rings" such as those as referred to hereinabove for "Ring A and Ring B", for example, from 3-membered to 10-membered cyclic hydrocarbon rings, preferably 5-membered or 6-membered cyclic hydrocarbon rings, such as benzene, $C_{3-10}$ cycloalkenes (e.g., cyclobutene, cyclopentene, cyclohexene, cycloheptene, cyclooctene, etc.), $C_{3-10}$ cycloalkanes (e.g., cyclobutane, cyclopentane, cyclohexane, cycloheptane, cyclooctane, etc.), etc. of these, preferred are 6-membered homocyclic rings, such as benzene, cyclohexene and cyclohexane rings, etc. Especially preferred is benzene ring.

The substituents for the above-mentioned benzene ring and other homocyclic rings include, for example, a halogen atom (e.g., fluorine, chlorine, bromine and iodine atoms), an optionally-halogenated $C_{1-10}$ alkyl group (e.g., methyl, chloromethyl, difluoromethyl trichloromethyl, trifluoromethyl, ethyl, 2-bromoethyl, 2,2,2-trifluoroethyl, perfluoroethyl, propyl, isopropyl, 3,3,3-trifluoropropyl, butyl, isobutyl, t-butyl, perfluorobutyl, pentyl, hexyl, octyl and decyl groups, etc.), an amino-substituted $C_{1-4}$ alkyl group (e.g., aminomethyl and 2-aminoethyl groups, etc.), a mono- or di-$C_{1-4}$ alkylamino-substituted $C_{1-4}$ alkyl group (e.g., methylaminomethyl, dimethylaminomethyl, 2-aminoethyl and 2-dimethylaminoethyl groups, etc.), a carboxyl-substituted $C_{1-4}$ alkyl group (e.g., carboxymethyl and carboxyethyl groups, etc.), a $C_{1-4}$ alkoxy-carbonyl-substituted $C_{1-4}$ alkyl group (e.g., methoxycarbonylethyl and ethoxycarbonylethyl groups, etc.), a hydroxyl-substituted $C_{1-4}$ alkyl group (e.g., hydroxymethyl and hydroxyethyl groups, etc.), a $C_{1-4}$ alkoxy-carbonyl-substituted $C_{1-4}$ alkyl group (e.g., methoxymethyl, ethoxyethyl and ethoxyethyl groups, etc.), a $C_{3-10}$ cycloalkyl group (e.g., cyclopropyl, cyclobutyl, cyclopentyl, cyclohexyl, cycloheptyl and cyclooctyl groups, etc.), a nitro group, a cyano group, a hydroxyl group, an optionally-halogenated $C_{1-10}$ alkoxy group (e.g., methoxy, difluoromethoxy, trichloromethoxy, trifluoromethoxy, ethoxy, 2,2,2-trifluoroethoxy, perfluoroethoxy, propoxy, isopropoxy, butoxy, isobutoxy, t-butoxy, perfluorobutoxy, pentyloxy, hexyloxy, octyloxy and decyloxy groups, etc.), an optionally-halogenated $C_{1-4}$ alkylthio group (e.g., methylthio, difluoromethylthio, trifluoromethylthio, ethylthio, propylthio, isopropylthio and butylthio groups, etc.), an amino group, a mono- or di-$C_{1-4}$ alkylamino group (e.g., methylamino, ethylamino, propylamino, dimethylamino and diethylamino groups, etc.), a cyclic amino group (e.g., a 5-membered to 9-membered cyclic amino group optionally having from 1 to 3 hetero atoms such as oxygen and sulfur atoms, etc., in addition to nitrogen atoms, concretely for example, pyrrolidino, piperidino and morpholino groups, etc.), a $C_{1-4}$ alkyl-carbonylamino group (e.g., acetylamino, propionylamino and butyrylamino groups, etc.), an aminocarbonyloxy group, a mono- or di-$C_{1-4}$ alkylaminocarbonyloxy group (e.g., methylaminocarbonyloxy, ethylaminocarbonyloxy, dimethylaminocarbonyloxy and diethylaminocarbonyloxy groups, etc.), a $C_{1-4}$ alkylsulfonylamino group (e.g., methylsulfonylamino, ethylsulfonylamino and propylsulfonylamino groups, etc.), a $C_{1-4}$ alkoxy-carbonyl group (e.g., methoxycarbonyl, ethoxycarbonyl, propoxycarbonyl, butoxycarbonyl and isobutoxycarbonyl groups, etc.), an aralkyloxycarbonyl group (e.g., benzyloxycarbonyl group, etc.), a carboxyl group, a $C_{1-6}$ alkyl-carbonyl group (e.g., methylcarbonyl, ethylcarbonyl and butylcarbonyl groups, etc.), a $C_{3-6}$ cycloalkyl-carbonyl group (e.g., cyclohexylcarbonyl group, etc.), a carbamoyl group, a mono- or di-$C_{1-4}$ alkylcarbamoyl group (e.g., methylcarbamoyl, ethylcarbamoyl, propylcarbamoyl, butylcarbamoyl, diethylcarbamoyl and dibutylcarbamoyl groups, etc.), a $C_{1-6}$ alkylsulfonyl group (e.g., methylsulfonyl, ethylsulfonyl and propylsulfonyl groups, etc.), etc.

The homocyclic Ring C may optionally be substituted, for example, by one 5-membered or 6-membered, aromatic monocyclic heterocyclic group (e.g., furyl, thienyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl groups, etc.), etc., and the aromatic monocyclic heterocyclic group may optionally be substituted by from 1 to 3 or so optionally halogenated $C_{1-4}$ alkyl groups (e.g., methyl, chloromethyl, difluoromethyl, trichloromethyl, trifluoromethyl, ethyl and isopropyl groups, etc.), etc.

As preferred substituents for the homocyclic Ring C (e.g., benzene ring, etc.), for example, mentioned are a halogen atom (e.g., fluorine, chlorine and bromine atoms, etc.), an optionally halogenated $C_{1-6}$ alkyl group (e.g., methyl, chloromethyl, difluoromethyl, trichloromethyl, trifluoromethyl, ethyl, 2-bromoethyl, 2,2,2-trifluoroethyl, perfluoroethyl, propyl, isopropyl, 3,3,3-trifluoropropyl, butyl, s-butyl, t-butyl and perfluorobutyl groups, etc.), a nitro group, a hydroxyl group, an optionally halogenated $C_{1-6}$ alkoxy group (e.g., methoxy, difluoromethoxy, trifluoromethoxy, ethoxy, 2,2,2-trifluoroethoxy, perfluoroethoxy, propoxy, isopropoxy, 3,3,3-trifluoropropoxy and butoxy groups, etc.), an amino group, a mono- or di-$C_{1-4}$ alkylamino-substituted $C_{1-4}$ alkyl group (e.g., methylaminomethyl, dimethylaminomethyl, 2-methylaminoethyl and 2-dimethylaminoethyl groups, etc.), a mono- or di-$C_{1-4}$ alklamino group (e.g., methylamino, ethylamino, dimethylamino and diethylamino groups, etc.), a $C_{1-4}$ alkoxy-carbonyl group (e.g., methoxycarbonyl and ethoxycarbonyl groups, etc.), a carboxyl group, a carbamoyl group, etc.

More preferred are a halogen atom (e.g., fluorine, chlorine and bromine atoms, etc.), an optionally halogenated $C_{1-4}$ alkyl group (e.g., methyl, chloromethyl, difluoromethyl, trichloromethyl, trifluoromethyl, ethyl, 2-bromoethyl, 2,2,2-trichloroethyl, 2,2,2-trifluoroethyl, perfluoroethyl, propyl, isopropyl and t-butyl groups, etc.), an optionally halogenated $C_{1-4}$ alkoxy group (e.g., methoxy, trifluoromethoxy, ethoxy, 2,2,2-trichloroethoxy, 2,2,2-trifluoroethoxy, perfluoroethoxy and propoxy groups, etc.), a di-$C_{1-4}$ alkylamino group (e.g., dimethylamino and diethylamino groups, etc.), a $C_{1-3}$ acyloxy group (e.g., acetoxy group, etc.), a hydroxyl group, etc. Preferably, the number of the substituents is, for example, from 1 to 3 or so.

Especially, preferred are a halogen atom (e.g., fluorine, chlorine and bromine atoms, etc.), an optionally halogenated $C_{1-4}$ alkyl group (e.g., methyl, chloromethyl, difluoromethyl, trichloromethyl, trifluoromethyl, ethyl, 2-bromoethyl, 2,2,2-trichloroethyl, 2,2,2-trifluoroethyl, perfluoroethyl, propyl, isopropyl and t-butyl groups, etc.), an optionally halogenated $C_{1-4}$ alkoxy group (e.g., methoxy, trifluoromethoxy, ethoxy, 2,2,2-trichloroethoxy, 2,2,2-trifluoroethoxy, perfluoroethoxy and propoxy groups, etc.)

The "heterocyclic ring" of the "optionally substituted heterocyclic ring" includes, for example, from 5-membered to 10-membered heterocyclic rings having from 1 to 4 hetero atoms of the same type or different two types, such as nitrogen, oxygen and/or sulfur atoms, etc., in addition to carbon atoms, etc. Concretely, the heterocyclic ring includes, for example;

(1) 5-membered or 6-membered, aromatic monocyclic heterocyclic rings, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.;

(2) 9-membered or 10-membered, aromatic, condensed heterocyclic rings, such as benzofuranyl, isobenzofuranyl, benzo[b]thienyl, indoliyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, a-carbolinyl, β-carbolinyl, g-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.;

(3) from 5-membered to 10-membered, non-aromatic heterocyclic rings, such as oxiranyl, azetidinyl, oxetanyl, thietanyl, pyrrolidinyl, tetrahydrofuryl, piperidyl, tetrahydrofuranyl, morpholinyl, thiomorpholinyl, pyrazinyl, etc.

Of the above-mentioned heterocyclic rings (1) to (3), for example, 5-membered or 6-membered heterocyclic rings having from 1 to 3 hetero atoms, such as nitrogen, oxygen and sulfur atoms, etc., in addition to carbon atoms, are widely utilized. Such heterocyclic rings include, for example, furyl, thienyl, pyrrolyl, oxazolyl, isoxazolyl, imidazolyl, pyrazolyl, pyridyl, pyridazinyl, quinolyl, isoquinolyl, thiazolyl, thiadiazolyl, thiophenyl, etc.

As the substituents for the optionally substituted heterocyclic rings, mentioned are substituents such as those as referred to hereinabove for the foregoing "optionally substituted homocyclic rings".

More preferably, Ring C includes optionally substituted benzene rings (especially, substituted benzene rings), for example, benzene rings optionally substituted by from 1 to 3 substituents selected from a halogen atom, an optionally halogenated $C_{1-4}$ alkyl group, an optionally substituted $C_{1-4}$ alkoxy group, a di-$C_{1-4}$ alkylamino group, a $C_{1-3}$ acyloxy group and a hydroxyl group (especially, benzene rings substituted by such substituent(s)). Concretely, the preferred Ring C includes, for example, optionally substituted benzene rings of a formula (C-1):

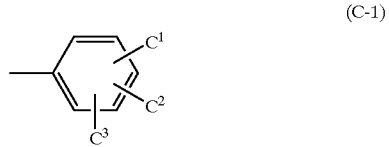

(C-1)

wherein $C^1$, $C^2$ and $C^3$ are the same or different and represent, independently, a hydrogen atom, a halogen atom, an optionally halogenated $C_{1-4}$ alkyl group, an optionally halogenated $C_{1-4}$ alkoxy group, a mono- or di-$C_{1-4}$ alkylamino group, a $C_{1-3}$ acyloxy group or a hydroxyl group; and optionally substituted benzene rings of a formula (C-2):

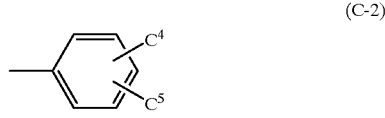

(C-2)

wherein $C^4$ and $C^5$ are the same or different and represent, independently, a hydrogen atom, a halogen atom, an optionally halogenated $C_{1-4}$ alkyl group or an optionally halogenated $C_{1-4}$ alkoxy group.

The halogen atom, the optionally halogenated $C_{1-4}$ alkyl group, the optionally halogenated $C_{1-4}$ alkoxy group and the mono- or di-$C_{1-4}$ alkylamino group to be represented by any of $C^1$, $C^2$, $C^3$, $C^4$ and $C^5$ may be the same as the above-mentioned halogen atom, optionally halogenated $C_{1-4}$ alkyl group, optionally halogenated $C_{1-4}$ alkoxy group and mono- or di-$C_{1-4}$ alkylamino group, respectively.

Even more preferably, Ring C includes, for example, benzene rings of the above-mentioned formulae (C-1) and (C-2) where $C^1$ to $C^5$ are as follows:

(1) $C^1$, $C^2$ and $C^3$ are the same or different and represent, independently, a halogen atom, an optionally halogenated $C_{1-4}$ alkyl group or an optionally halogenated $C_{1-4}$ alkoxy group;

(2) $C^1$, $C^2$ and $C^3$ are the same or different and represent, independently, a halogen atom or an optionally halogenated $C_{1-4}$ alkyl group;

(3) $C^1$, $C^2$ and $C^3$ are the same or different and represent, independently, a halogen atom;

(4) $C^1$, $C^2$ and $C^3$ are the same or different and represent, independently, an optionally halogenated $C_{1-4}$ alkyl group;

(5) $C^1$, $C^2$ and $C^3$ are the same or different and represent, independently, an optionally halogenated $C_{1-4}$ alkoxy group;

(6) $C^4$ and $C^5$ are the same or different and represent, independently, a halogen atom;

(7) $C^4$ and $C^5$ are the same or different and represent, independently, an optionally halogenated $C_{1-4}$ alkyl group; or (8) $C^4$ and $C^5$ are the same or different and represent, independently, an optionally halogenated $C_{1-4}$ alkoxy group.

As examples of the "optionally halogenated $C_{1-4}$ alkyl group", the "optionally halogenated $C_{1-4}$ alkoxy group" and the "halogen atom" in the above-mentioned embodiments (1) to (8), referred to are the same ones as those mentioned hereinabove.

Further more preferably, Ring C includes, for example, benzene rings of the above-mentioned formula (C-2) where $C^4$ and $C^5$ are as follows:

(a) one of $C^4$ and $C^5$ is a hydrogen atom and the other is a methoxy group;

(b) $C^4$ and $C^5$ are both chlorine atoms;

(c) one of $C^4$ and $C^5$ is a methoxy group and the other is an isopropyl group;

(d) one of $C^4$ and $C^5$ is a methoxy group and the other is a 1-methoxy-1-methylethyl group; or (e) $C^4$ and $C^5$ are both trifluoromethyl groups.

Regarding "Ring Z"

In the above-mentioned formulae, Ring Z represents an optionally-substituted nitrogen containing heterocyclic ring. Various substituents are referred to as substituents for Ring Z, which include, for example, an alkyl group (e.g., a linear or branched alkyl group having from 1 to 6 carbon atoms, preferably a linear or branched alkyl group having from 1 to 4 carbon atoms, such as methyl, ethyl, propyl, isopropyl, butyl, isobutyl, sec-butyl and tert-butyl groups, etc.), an alkenyl group (e.g., an alkenyl group having from 2 to 6 carbon atoms, preferably an alkenyl group having from 2 to 4 carbon atoms, such as ethenyl, propenyl, isopropenyl, butenyl, isobutenyl sec-butenyl groups, etc.), an alkynyl group (e.g., an alkynyl group having from 2 to 6 carbon atoms, preferably an alkynyl group having from 2 to 4 carbon atoms, such as ethynyl, propynyl, isopropynyl, butynyl, isobutynyl and sec-butynyl groups, etc.), a cycloalkyl group (e.g., a $C_{3-8}$ cycloalkyl group, preferably a $C_{3-6}$ cycloalkyl group, such as cyclopropyl, cyclobutyl, cyclopentyl and cyclohexyl groups, etc.), a cycloalkyl-alkyl group (e.g., a $C_{3-6}$ cycloalkyl-$C_{1-4}$ alkyl group, such as cyclopropylmethyl, cyclopropylethyl and cyclohexylmethyl groups, etc.), an aryl group (e.g., an aryl group having from 6 to 14 carbon atoms, preferably an aryl group having from 6 to 10 carbon atoms, such as phenyl, 1-naphthyl, 2-naphthyl, anthryl and phenanthryl groups, etc., especially, phenyl group), a nitro group, a cyano group, a hydroxyl group, a $C_{1-4}$ alkoxy group (e.g., methoxy, ethoxy, propoxy, isopropoxy and butoxy groups, etc.), a $C_{1-4}$ alkylthio group (e.g., methylthio, ethylthio and propylthio groups, etc.), an amino group, a mono- or di-$C_{1-4}$ alkylamino group (e.g., methylamino, ethylamino, propylamino, dimethylamino and diethylamino groups, etc.), a cyclic amino group (e.g., a 5-membered to 9-membered cyclic amino group optionally having from 1 to 3 hetero atoms, such as oxygen and sulfur atoms, etc., in addition to nitrogen atom, concretely, for example, pyrrolidino, piperidino, morpholino and thiomorpholino groups, etc.), a $C_{1-4}$ alkyl-carbonylamino group (e.g., acetylamino, propionylamino and butyrylamino groups, etc.), a $C_{1-4}$ alkylsulfonylamino group (e.g., methylsulfonylamino and ethylsulfonylamino groups, etc.), a $C_{1-4}$ alkoxy-carbonyl group (e.g., methoxycarbonyl, ethoxycarbonyl and propoxycarbonyl groups, etc.), a carboxyl group, a $C_{1-6}$ alkyl-carbonyl group (e.g., methylcarbonyl, ethylcarbonyl and propylcarbonyl groups, etc.), a carbamoyl group, a mono- or-di-$C_{1-4}$ alkylcarbamoyl group (e.g., methylcarbamoyl and ethylcarbamoyl groups, etc.), a $C_{1-6}$ alkylsulfonyl group (e.g., methylsulfonyl, ethylsulfonyl and propylsulfonyl groups, etc.), an oxo group, a thioxo group, etc. The number of the substituents is, for example, from 1 to 5 or so, preferably 1, 2 or so, depending on the size of Ring Z.

Ring Z may be a heterocyclic ring optionally having at least one hetero atom selected from nitrogen, oxygen and sulfur atoms, in addition to Y and the nitrogen atom N, and is preferably an optionally oxoated ring.

Ring Z includes rings of a formula (Z-1):

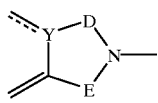

(Z-1)

wherein D and E represent groups from which Ring Z as mentioned above is formed via the nitrogen atom adjacent to E.

Preferably, D and E which form Ring Z represent, independently, an alkylene group optionally having an oxo group, oxyalkylene group, or iminoalkylene group. The alkylene groups optionally having an oxo group to be represented by D and E preferably have carbon atoms from which Ring Z is formed to be a 5-membered to 12-membered ring, preferably a 5-membered to 9-membered ring. The numbers of the carbon atoms that constitute the alkylene groups of D and E may be the same or different.

Preferably, D includes, for example, $C_{1-7}$ alkylene group optionally having an oxo group, especially $C_{1-5}$ alkylene group optionally having an oxo group $C_{1-7}$ oxyalkylene groups, especially $C_{1-5}$ oxyalkylene groups, $C_{1-7}$ iminoalkylene groups, especially $C_{1-5}$ imminoalkylene groups. More preferably, D includes an alkylene group of a formula —(CH$_2$)$_m$— (where m is from 1 to 7), an oxyalkylene group of a formula —O—(CH$_2$)$_p$ (where p is from 1 to 7), iminoalkylene group of a formula —NH—(CH$_2$)$_q$ (where q is from 1 to 7. In these formula, m is preferably from 1 to 5, more preferably from 2 to 5.

Preferably, E includes, for example, $C_{1-3}$ alkylene group optionally having an oxo group, more preferably an alkylene group optionally having an oxo group having one or two carbon atoms, even more preferably a methylene group optionally having an oxo group.

The number of the oxo groups that are substitutable in Ring Z is not specifically limited but may be selected from 1 to 3 or so depending on the size of Ring Z. Where Ring Z is a 5-membered to 10-membered ring, the number of the substitutable oxo groups is 1, 2 or so. Oxo group(s) may be substituted at at least either one of D and/or E. Preferably, oxo group(s) is/are substituted at E in Ring Z.

Preferably, in Ring Z, D is an alkylene group or oxyalkylene group having from 1 to 5 carbon atoms, more preferably from 2 to 5 carbon atoms especially, an alkylene group having from 2 to 5 carbon atoms, while E is an alkylene group having an oxo group having 1 or 2 carbon atoms, especially >C=O. Especially preferably, Ring Z includes, for example, from 5-membered to 9-membered rings of a formula (Z-2):

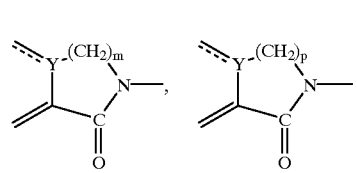

(Z-2)

wherein each m and p, independently, represents an integer of from 1 to 5.

Regarding "n"

In the above-mentioned formulae, n represents an integer of from 1 to 6, preferably an integer of from 1 to 3, especially preferably 1 or 2. More preferably, n is 1.

Regarding Compounds (I) and (Ia)

In compounds of the above-mentioned general formulae (I) and (Ia), the combination of "Ring M" "—X $\overline{\ldots\ldots}$ Y<", "$R^{a}$", "$R^{b}$", "Ring A", "Ring B", "Ring C", "Ring Z" and "n" is not specifically limited. These may be combined suitably to construct the compounds (I) and (Ia). Preferred compounds (I) and (Ia) are constructed by combining the above-mentioned preferred embodiments of "Ring M" "—X $\overline{\ldots\ldots}$ Y<", "$R^{a}$", "$R^{b}$", "Ring A", "Ring B", "Ring C", "Ring Z" and "n".

Of compounds of the above-mentioned general formula (I), especially those of the above-mentioned general formula (Ia), preferred are (1) the following compounds or pharmaceutically-acceptable salts thereof.

Compounds of formula (I) or (Ia) wherein;
one of Ring A and Ring B is a 5-membered or 6-membered heterocyclic ring having one or two hetero atoms selected from nitrogen and oxygen atoms, in addition to carbon atoms, while the other is a benzene ring, and the Rings A and B may optionally have one or two substituents selected from a halogen atom and an optionally halogenated $C_{1-4}$ alkyl group;
Ring C is a benzene ring optionally having from 1 to 3 substituents selected from a halogen atom, an optionally halogenated $C_{1-6}$ alkyl group (preferably, $C_{1-4}$ alkyl group) and an optionally halogenated $C_{1-6}$ alkoxy group (preferably, $C_{1-4}$ alkoxy group);
D that constitutes Ring Z is —(CH$_2$)$_m$— (where m is an integer of from 1 to 7) or —O—(CH$_2$)p— (where p is an integer of from 1 to 7);
E that constitutes Ring Z is >C=O;
—X $\overline{\ldots\ldots}$ Y< is —CO—N<;
n is 1,
or pharmaceutically-acceptable salts thereof.

The above-mentioned "5-membered or 6-membered heterocyclic ring" includes, for example, pyridine, pyrazine, pyrrole, thiophene, thiazole, tetrahydropyrazine, piperidine, etc. Concretely, Ring A includes heterocyclic rings of the above-mentioned formula (A-5), etc., and Ring B includes benzene rings of the above-mentioned formulae (B-7) and (B-8), especially the above-mentioned formula (B-10), etc.

The above-mentioned "halogen atom" includes, for example, fluorine, chlorine and bromine atoms, etc.; the "optionally-halogenated $C_{1-4}$ alkyl group" includes, for example, methyl, chloromethyl, difluoromethyl, trichloromethyl, trifluoromethyl, ethyl; 2-bromoethyl, 2,2, 2-trifluoroethyl, perfluoroethyl, propyl, 3,3,3-trifluoropropyl, isopropyl, 2-trifluoromethylethyl, butyl, 4,4, 4-trifluorobutyl, isobutyl, sec-butyl and tert-butyl groups, etc.; the "optionally halogenated $C_{1-6}$ alkyl group" includes pentyl and hexyl groups, etc., in addition to the above-mentioned alkyl groups and halogenated alkyl groups.

The "optionally halogenated $C_{1-4}$ alkoxy group" includes, for example, methoxy, difluoromethoxy, trifluoromethoxy, ethoxy, 2,2,2-trifluoroethoxy, perfluoroethoxy, propoxy, isopropoxy, butoxy, 4,4,4-trifluorobutoxy, isobutoxy, sec-butoxy and tert-butoxy groups, etc.; and the "optionally halogenated $C_{1-6}$ alkoxy group" includes pentyloxy and hexyloxy groups, etc., in addition to the above-mentioned alkoxy groups and halogenated alkoxy groups.

Of compounds of the above-mentioned general formula (I), especially those of the above-mentioned general formula (Ia), also preferred are (2) the following compounds or pharmaceutically-acceptable salts thereof.

Compounds of formula (I) or (Ia) wherein:

Ring A is a 5-membered or 6-membered heterocyclic ring having one nitrogen atom or one sulfur atom, in addition to carbon atoms, for example, a heterocyclic ring of a formula (A-7):

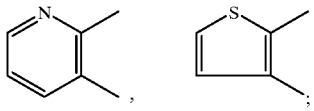

(A-7)

Ring B is a benzene ring optionally having from 1 to 3 substituents selected from a halogen atom and an optionally halogenated $C_{1-4}$ alkyl group;

Ring C is a benzene ring optionally having from 1 to 3 substituents selected from a halogen atom, an optionally halogenated $C_{1-4}$ alkyl group and an optionally halogenated $C_{1-4}$ alkoxy group;

D that constitutes Ring Z is —$(CH_2)_m$— (where m is an integer of from 1 to 7) or —O—$(CH_2)p$— (where p is integer of from 1 to 7);

E that constitutes Ring Z is >C=O;

—X ..... Y< is —CO—N<;

n is 1, or pharmaceutically-acceptable salts thereof.

As examples of the "halogen atom", the "optionally halogenated $C_{1-4}$ alkyl group" and the "optionally halogenated $C_{1-4}$ alkoxy group", mentioned are those as referred to hereinabove for the foregoing compounds (1).

More preferably, compounds of formula (I) or (Ia) wherein;

$R^a$ and $R^b$ are the same or different and represent, independently, a hydrogen atom, optionally halogenated $C_{1-4}$ alkyl groups, $C_{1-6}$ alkoxy-$C_{1-6}$ alkyl groups, $C_{1-6}$ alkylthio-$C_{1-6}$ alkyl groups, amino-$C_{1-6}$ alkyl groups, $C_{1-7}$ acylamino-$C_{1-6}$ alkyl groups, mono- or di-$C_{1-6}$ alkylamino-$C_{1-4}$ alkyl groups, $C_{3-10}$ cycloalkylamino-$C_{1-6}$ alkyl groups, $C_{1-6}$ alkyl groups having 5-membered or 6-membered cyclioamino which optionally substituted by $C_{1-6}$ alkyl, $C_{1-6}$ alkylsulfonylamino-$C_{1-6}$ alkyl or $C_{1-6}$ alkylcarbonyloxy-$C_{1-6}$ alkyl; or $R^a$ and $R^b$ are bonded to each other to form pyridine ring which is optionally substituted by 1 to 3 substituents selected from a halogen atom and a $C_{1-4}$ alkyl group;

Ring B is a benzene ring optionally having 1 to 3 substituents selected from a halogen atom, an optionally halogenated $C_{1-4}$ alkyl group and an optionally halogenated $C_{1-4}$ alkoxy group;

Ring C is a benzene ring optionally having 1 to 3 substituents selected from a halogen atom, an optionally halogenated $C_{1-4}$ alkyl group, an optionally halogenated $C_{1-4}$ alkoxy group, an amino group optionally substituted by $C_{1-4}$ alkyl group, a $C_{1-3}$ acyloxy group and a hydroxyl group;

Ring Z is a 5-membered to 10-membered nitrogen containing heterocyclic ring optionally having an oxo group and optionally substituted $C_{1-4}$ alkyl group or a hydroxy group;

—X ..... Y— is —N=CC< or —CO—N< and n is an integer of 1;

and n is 1, or pharmaceutically-acceptable salts thereof.

Preferred compounds of formulae (I) and (Ia) include, for example, compounds of the following general formula or salts thereof.

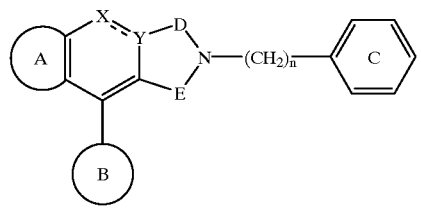

wherein D and E represent alkylene groups, optionally having an oxo group and the other symbols have the same meanings as above.

Preferably, D and E represent, independently, a $C_{1-3}$ alkylene group optionally substituted by one oxo group.

More preferred compounds of formulae (I) and (Ia) include, for example, compounds of the following general formula or salts thereof.

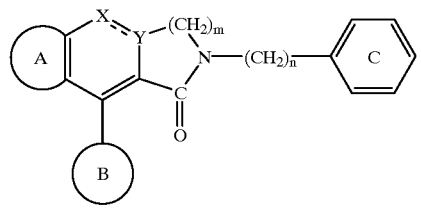

wherein m represents an integer of from 1 to 7, and the other symbols have the same meanings as above.

m is preferably an integer of from 2 to 5.

Where the above-mentioned compounds of formulae (I) and (Ia) form salts and used in medicines, it is preferable that the salts are pharmaceutically-acceptable salts.

Examples of such pharmaceutically-acceptable salts include salts with inorganic acids, such as hydrochloric acid, sulfuric acid, phosphoric acid, diphosphoric acid, hydrobromic acid, nitric acid, etc., or salts with organic acids, such as acetic acid, malic acid, maleic acid, fumaric acid, tartaric acid, succinic acid, citric acid, lactic acid, methanesulfonic acid, p-toluenesulfonic acid, palmitic acid, salicylic acid, stearic acid, etc.

Compounds (I) and (Ia) or salts thereof of the present invention include stereoisomers such as cis- and trans-isomers, etc., racemates, as well as optically-active forms such as R-forms, S-forms, etc. Depending on the size of Ring Z, compounds (I) and (Ia) or salts thereof may include conformation-dependent isomers. All such isomers are within the scope of the compounds (I) and (Ia) or salts thereof of the present invention.

Method for Producing Compounds or Salts Thereof

Compounds (I) and (Ia) or salts thereof of the present invention can be produced, for example, by cyclizing a compound of the following general formula (II) or a salt thereof.

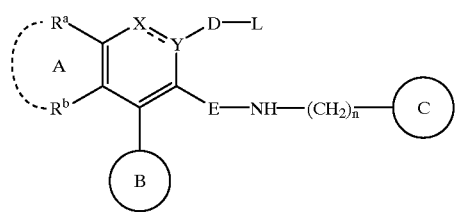

(II)

wherein L represents a leaving group, and the other symbols have the same meanings as above.

The leaving group L in compound (II) includes, for example, a halogen atom (e.g., chlorine, bromine and iodine atoms, etc.), a substituted sulfonyloxy group (e.g., methanesulfonyloxy, ethanesulfonyloxy, benzenesulfonyloxy and p-toluenesulfonyloxy groups, etc.), etc.

The compound (II) can be applied to the reaction as a free compound but may also be applied thereto as its salt (for example, as an alkali metal salt, such as lithium, sodium, potassium or the like salt, of the compound). In general, the reaction is conducted in a solvent that is inert to the reaction. As the solvent, for example, preferably used is any of halogenated hydrocarbons such as dichloromethane, chloroform, etc., nitriles such as acetonitrile, etc., ethers such as dimethoxyethane, tetrahydrofuran, etc., aprotic polar solvents such as dimethylformamide, dimethylsulfoxide, hexamethylphosphoramide, etc.

Addition of a base to the reaction system advantageously promotes the reaction. As the base, for example, advantageously employed is any of inorganic bases (alkali metal hydroxides such as sodium hydroxide, potassium hydroxide, etc.; alkali metal hydrogencarbonates such as sodium hydrogencarbonate, potassium hydrogencarbonate, etc.; alkali metal carbonates such as sodium carbonate, potassium carbonate, etc.; alkali metal hydrides such as sodium hydride, potassium hydride, etc.; sodium amide; alkoxides such as sodium methoxide, sodium ethoxide, etc.), and organic bases (amines such as trimethylamine, triethylamine, diisopropylethylamine, etc.; cyclic amines such as pyridine, etc.).

In the above-mentioned cyclization, it is also possible to convert the compound (II) into its salt with a base (for example, any of the above-mentioned alkali metal salts, alkaline earth metal salts, etc.) prior to the reaction, in place of using the base. The amount of the base, if used, varies, depending on the kind of the compound (II) and the solvent to be used and on the other reaction conditions, and is, in general, from 1 to 10 mols or so, preferably from 1 to 5 mols or so, per mol of the compound (II) used.

The reaction temperature falls, for example, within the range between about −50° C. and about 200° C., preferably between about −20° C. and about 150° C. The reaction time varies, depending on the kind of the compound (II) used or the kind of its salt used and also on the reaction temperature, etc., and is, for example, from 1 to 72 hours or so, preferably from 1 to 24 hours or so.

Of compounds (I) and (Ia) of the present invention, those where Ring A is a tetrahydropyridine ring can be produced by reducing compounds (I) and (Ia) where Ring A is a pyridine ring. The reduction can be conducted by various methods. For example, preferred is a method of reducing the compounds in the presence of a metal catalyst for catalytic reduction. The catalyst to be employed in the catalytic reduction includes, for example, platinum catalysts such as platinum black, platinum oxide, platinum carbon, etc., palladium catalysts such as palladium black, palladium oxide, palladium barium sulfate, palladium carbon, etc.; nickel catalysts such as reduced nickel, nickel oxide, Raney nickel, Urushibara nickel, etc. The amount of the catalyst to be used varies, depending on the type of the catalyst, and is, in general, from 0.1 to 10% (w/w) or so relative to the compound (I) or (Ia) to be reduced.

The reduction is generally conducted in a solvent. The solvent includes, for example, alcohols such as methanol, ethanol, propanol, isopropanol, etc., ethers such as tetrahydrofuran, dioxane, etc., esters such as ethyl acetate, etc. The reaction temperature falls, for example, between 0° C. and 200° C. or so, preferably between 20° C. and 110° C. or so. The reaction time is generally from 0.5 to 48 hours or so, preferably from 1 to 16 hours or so. In general, the reaction is conducted under normal pressure in many cases but, if desired, may be conducted under pressure (for example, at from 3 to 10 atmospheres or so).

The reduction may also apply to the conversion of other aromatic heterocyclic rings into non-aromatic heterocyclic rings.

Compounds of formulae (I) and (Ia) where Ring A is a tetrahydropyridine ring can also be produced by reacting a compound of formula (I) or (Ia) where Ring A is a pyridine ring with an alkylating agent of a formula, Q-L' (where Q represents an optionally substituted alkyl group, and L' represents a removable group) to convert it into the corresponding quaternary salt, followed by reducing the resulting quaternary salt. As examples of the removable group L', referred to are those of the removable group L as mentioned hereinabove.

The alkylating agent Q-L' that is used for converting the compound into the corresponding quaternary salt includes alkane halides (e.g., chlorides, bromides, iodides, etc.), sulfates and sulfonates (e.g., methanesulfonates, p-toluenesulfonates, benzenesulfonates, etc.), etc. Especially preferred are alkyl halides. The amount of the alkylating agent to be used is, for example, from 1 to 100 equivalents or so, preferably from 1 to 30 equivalents or so, per mol of the substrate.

The alkylation is generally conducted in a solvent. The solvent includes, for example, alcohols such as methanol, ethanol, propanol, isopropanol, etc., ethers such as tetrahydrofuran, dioxane, etc., esters such as ethyl acetate, etc., halogenated hydrocarbons such as dichloromethane, 1,2-dichloroethane, etc. It is also possible to use the alkylating agent itself as the solvent. The reaction temperature falls, for example, between 10° C. and 200° C. or so, preferably between 20° C. and 110° C. or so. The reaction time is generally from 0.5 to 24 hours or so, preferably from 1 to 16 hours or so.

The reduction of the quaternary salt as formed in the previous reaction into a tetrahydropyridine ring may be conducted in the presence of a reducing agent, such as a metal hydride or the like, in an inert solvent. The metal hydride to be used as the reducing agent includes, for example, sodium borohydride, lithium borohydride, zinc borohydride, sodium borocyanohydride, lithium borocyanohydride, lithium aluminium hydride, etc. Of these, preferred are sodium borohydride, etc. The amount of the reducing agent to be used is, for example, from 1 to 10 equivalents or so, preferably from 1 to 2 equivalents or so, relative to the quaternary salt. The reaction solvent includes, for example, lower alcohols such as methanol, ethanol, etc., ethers such as dioxane, tetrahydrofuran, etc., hydrocarbons such as benzene, toluene, etc. These solvents can be used singly or as combined. The reaction temperature falls, in general, between about −100° C. and about 40° C., preferably between about −80° C. and about 25° C. The reaction time is generally from 5 minutes to 10 hours or so, preferably from 10 minutes to 5 hours or so.

As the case may be, the reduction of the above-mentioned quaternary salts may give compounds of the present invention having a dihydropyridine ring, depending on the type of the quaternary salts to be reduced. The dihydropyridine ring thus formed may further be reduced into a tetrahydropyridine ring, for example, according to the above-mentioned catalytic reduction or the like. Where Ring A is a tetrahydropyridine ring and its nitrogen atom has a hydrogen atom as bonded thereto, it may be alkylated with the above-mentioned alkylating agent of formula Q-L' (where the symbols have the same meanings as above) to thereby introduce the group Q into the nitrogen atom of the ring. In this manner, therefore, compounds of the invention where the nitrogen atom of the tetrahydropyridine Ring A is substituted by the group Q are obtained.

It is also possible to obtain compounds of the invention where Ring A is a pyridone ring by oxidizing the corresponding compounds where Ring A is a quaternary salt of a pyridine ring. The oxidation can be conducted, for example, in accordance with a known method (see E. A. Prill et al.; Organic Syntheses, Combined Vol. 2. p. 419 (1957)) or with reference thereto.

Compounds of the invention where Ring B is an aromatic heterocyclic ring can be converted into the corresponding compounds where Ring B is a non-aromatic heterocyclic ring by reducing them in the same manner as above.

Of compounds (I) of the present invention, those where —X$\overline{\dots\dots}$Y< is —CS—N< can be produced by reacting the corresponding compounds where —X$\overline{\dots\dots}$Y< is —CO—N< with a suitable sulfide. The sulfide includes, for example, phosphorus pentasulfide, Lowesson reagents, etc. This reaction is, in general, conducted in the absence of water in a solvent, for example in a halogenated hydrocarbon such as dichloromethane, chloroform or the like, an ether such as dioxane, tetrahydrofuran or the like, or a hydrocarbon such as benzene, toluene or the like. The amount of the sulfide to be used is not smaller than the equimolar amount, preferably from 2 to 5 mols or so, relative to the compound to be sulfidized therewith. The reaction temperature falls, for example, between 20° C. and 120° C or so. The reaction time varies, depending on the kind of the compound to be sulfidized, the type of the sulfide to be used, the reaction temperature, etc., and is, for example, from 1 to 8 hours or so.

Where the compounds (I) and (Ia) or salts thereof which are produced according to the methods mentioned above have lower ($C_{1-6}$) alkoxy group(s) at the benzene ring(s) in the groups of Ring A, Ring B and Ring C, if desired, these may optionally be reacted with, for example, boron tribromide or the like according to known methods to thereby convert the lower alkoxy group(s) into hydroxyl group(s). This reaction may be conducted, in general, in a solvent (e.g., halogenated hydrocarbons such as dichloromethane, chloroform, carbon tetrachloride, etc., hydrocarbons such as benzene, toluene, etc.), at from about −20° C. to about 80° C., preferably at from about 0° C. to about 30° C. The amount of boron tribromide to be used is from about 1 to about 10 molar equivalents, preferably from about 1 to about 5 molar equivalents, relative to one lower alkoxy group. The reaction time is, in general, from 15 minutes to 24 hours or so, preferably from 30 minutes to 12 hours or so.

Where the compounds (I) and (Ia) or salts thereof which are produced according to the methods mentioned above have hydroxyl group(s) at the benzene ring(s) in the groups of Ring A, Ring B and ring C, if desired, these may be alkylated or acylated to thereby convert the hydroxyl group(s) into alkoxy or acyloxy group(s).

The alkylation may be conducted in the presence of a base in a solvent by making the compounds reacted with an alkylating agent. The solvent includes, for example, alcohols such as methanol, ethanol, propanol, etc., ethers such as dimethoxyethane, dioxane, tetrahydrofuran, etc., ketones such as acetone, etc., amides such as N,N-dimethylformamide, etc. The base includes, for example, organic bases such as trimethylamine, triethylamine, N-methylmorpholine, pyridine, picoline, N,N-dimethylaniline, etc., and inorganic bases such as potassium carbonate, sodium carbonate, potassium hydroxide, sodium hydroxide, etc.

The alkylating agent includes, for example, optionally substituted alkane halides (e.g., chlorides, bromides, iodides, etc.), sulfates and sulfonates (e.g., methanesulfonates, p-toluenesulfonates, benzenesulfonates, etc.), etc. The amount of the alkylating agent to be used is from about 1 to about 5 molar equivalents, preferably from about 1 to about 3 molar equivalents, relative to mol of the starting phenolic derivative. The reaction temperature falls, in general, between about −10° C. and about 100° C., preferably from about 0° C. and about 80° C. The reaction time is, in general, from 15 minutes to 24 hours or so, preferably from 30 minutes to 12 hours or so.

The acylation is conducted by reacting the phenolic derivative with a desired carboxylic acid or a reactive derivative thereof. This reaction is generally conducted in a solvent, though depending on the type of the acylating agent to be used and the kind of the starting phenolic derivative to be acylated. If desired, a base may be added to the reaction system so as to promote the reaction. The solvent includes, for example, hydrocarbons such as benzene, toluene, etc., ethers such as ethyl ether, dioxane, tetrahydrofuran, etc., esters such as ethyl acetate, etc., halogenated hydrocarbons such as chloroform, dichloromethane, etc., amides such as N,N-dimethylformamide, etc., aromatic amines such as pyridine, etc. The base includes, for example, hydrogencarbonates such as sodium hydrogencarbonate, potassium hydrogencarbonate, etc., carbonates such as sodium carbonate, potassium carbonate, etc., acetates such as sodium acetate, etc., tertiary amines such as triethylamine, etc., aromatic amines such as pyridine, etc. The reactive derivative of a carboxylic acid, which is used as the acylating agent, includes, for example, acid anhydrides, mixed acid anhydrides, acid halides (e.g., chlorides, bromides), etc. The amount of the acylating agent to be used is from 1 to 5 molar equivalents, preferably from 1 to 3 molar equivalents, relative to mol of the starting phenolic derivative. The reaction temperature falls, in general, between 0° C. and 150° C. or so, preferably about 10° C. and 100° C. or so. The reaction time is generally from 15 minutes to 12 hours or so, preferably from 30 minutes to 6 hours or so.

Of compounds of formula (I) and (Ia), those where D is a carbonyl group, an oxyalkylene group [—O—$(CH_2)_q$—] or an iminoalkylene group [—NH—$(CH_2)_q$—] can be obtained by reacting the leaving group La (for example, the above-mentioned removable group L such as a halogen atom or the like, an amido group optionally having a substituent at its nitrogen atom, etc.) as substituted on the Ring M in the absence of D with the reactive moiety (for example, the active hydrogen atom of a hydroxyl group, an amino group, a mono-$C_{1-6}$ alkylamino group or the like) of the substituent as bonded to the nitrogen atom adjacent to E, in accordance with the methods mentioned above. The substituent as bonded to the nitrogen atom adjacent to E is, for example, a linear or branched $C_{1-6}$ alkylene group optionally having substituent(s) selected from a $C_{1-6}$ alkyl group, a hydroxyl group, a $C_{1-6}$ alkoxy group, etc.

Where the compounds (I) and (Ia) are obtained in the above-mentioned methods as free compounds, they can be converted into their salts by ordinary methods, for example, into their salts with inorganic acids (e.g., hydrochloric acid, sulfuric acid, hydrobromic acid, etc.), organic acids (e.g., methanesulfonic acid, benzenesulfonic acid, toluenesulfonic acid, oxalic acid, fumaric acid, maleic acid, tartaric acid, etc.), inorganic bases (e.g., alkali metals such as sodium, potassium, etc., alkaline earth metals such as calcium, magnesium, etc., aluminium, ammonium, etc.), organic bases (e.g., trimethylamine, triethylamine, pyridine, picoline, ethanolamine, diethanolamine, triethanolamine, dicyclohexylamine, N,N'-dibenzylethylenediamine, etc.), etc. Where the compounds (I) are obtained in the form of their salts, the salts may be converted into free compounds or other salts by ordinary methods.

The final compounds (I) and (Ia) or salts thereof thus produced according to the methods mentioned hereinabove can be separated and isolated by ordinary separation and isolation means (for example, by condensation, solvent extraction, column chromatography, recrystallization, etc.). Where the compounds (I) and (Ia) are of optically-active forms, they can be resolved into d-forms and l-forms by conventional optical resolution.

Of the starting compounds (II) that are used for producing the compounds (I) and (Ia) or salts thereof of the present invention, compounds (IIa) wherein —X ..... Y< is —CO—N<, D is an ethylene group, and E is >C=O can be produced, for example, according to the following reaction process (1):

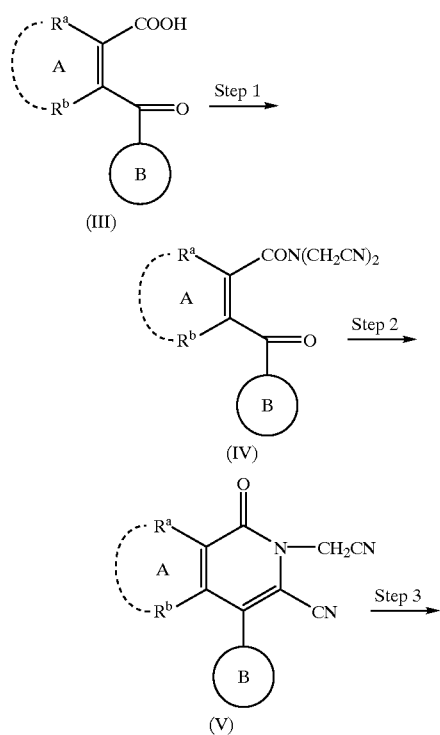

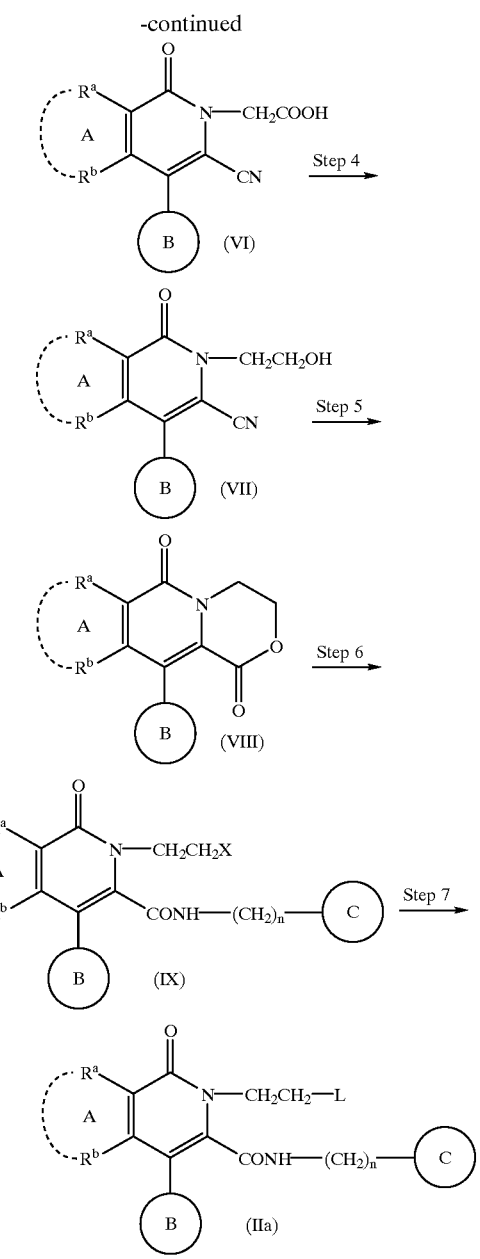

In these formulae, the symbols have the same meanings as above.

The step (1) and the step (2) in the above-mentioned reaction process (1) can be conducted in accordance with known methods for producing the corresponding isoquinolone-skeleton compounds where Ring A and Ring B are both optionally substituted benzene rings (for example, a method described in EP-A-481383, etc.). The step (1) is to produce an amide compound (IV) by reacting the carboxyl group in a compound (III) and the amino group in an iminodiacetonitrile. This reaction may be conducted, in general, in a solvent, by using a compound (III) or a carboxyl-reactive derivative thereof and an iminodiacetonitrile. The reactive derivative includes, for example, acid halides, mixed acid anhydrides, active esters, etc. The solvent includes, for example, halogenated hydrocarbons such as chloroform, dichloromethane, 1,2-dichlroethane, etc., ethers such as ethyl ether, tetrahydrofuran, dioxane, dimethoxyethane, etc., esters such as ethyl acetate, etc., hydrocarbons such as benzene, toluene, etc., pyridine, amides such as N,N-dimethylformamide, etc. The amount of the iminodiacetonitrile is from 1 to 5 molar equivalents or so, preferably from 1 to 3 molar equivalents or so, relative tool of the reactive derivative of the above-mentioned compound (III).

The reaction may be conducted in the presence of a base, by which the reaction is promoted. The base includes, for example, organic bases (e.g., alkylamines such as triethylamine, etc., cyclic amines such as N-methylmorpholine, pyridine, etc., aromatic amines such as N,N-dimethylaniline, N,N-diethylaniline, etc.), and inorganic bases (e.g., alkali metal carbonates such as sodium carbonate, potassium carbonate, etc., alkali metal hydrogencarbonates such as sodium hydrogencarbonate, potassium hydrogencarbonate, etc.). The amount of the base to be used is, for example, from 1 to 5 molar equivalents or so, preferably from 1 to 3 molar equivalents or so, relative to mol of the compound (III) or its reactive derivative. In the reaction of the step (1), employable is a water-immiscible solvent. In this case, water may be added to the reaction system and the reaction is thus conducted in the resulting two-phase system.

The reaction time is generally from 1 to 48 hours or so, preferably from 1 to 24 hours or so. The reaction temperatures falls generally between −10° C. and 120° C. or so, preferably between about 0° C. and 100° C. or so.

The step (2) is to obtain a closed compound (V) by subjecting the compound (IV) as formed in the previous step (1) to intramolecular addition-dehydration. In general, a base is employed in this reaction. The base includes, for example, organic bases (e.g., 1,5-diazabicyclo[4.3.0]non-5-ene (DBN), 1,8-diazabicyclo[5.4.0]undecen-7-ene (DBU), N-benzyltrimethylammonium hydroxide (Triton B), etc.), and inorganic bases (e.g., alkoxides such as sodium methoxide, sodium ethoxide, potassium t-butoxide, etc., alkali metal hydrides such as sodium hydride, potassium hydride, etc., n-butyl lithium, lithium diisopropylamide, etc.). The amount of the base to be used is, for example, from 0.5 to 20 equivalents or so, preferably from 1 to 5 equivalents or so, relative to the compound (IV).

The ring-closure reaction is generally conducted in a solvent. The solvent includes, for example, those as referred to as employable in the step (1). The reaction temperature varies, depending on the type of the base to be used, and falls, for example, between about −80° C. and 200° C. or so, preferably about −50° C. and 150° C. or so. The reaction time varies, depending on the starting materials, the base, the reaction temperature and the type of the solvent used, and is, for example, from about 10 minutes to 24 hours or so.

In the previous reaction, an intramolecular adduct is formed as the intermediate. In order to promote the dehydration of the intermediate to obtain a compound (V), it is often preferable to previously add a dehydrating agent (e.g., p-toluenesulfonic acid, methanesulfonic acid, acetic anhydride, etc.) to the reaction system. It is also preferable that the intermediate is isolated and thereafter it is dehydrated in the presence of a dehydrating agent to obtain a compound (V).

The step (3) is to produce a compound (VI) by hydrolyzing the cyano group of the N-cyanomethyl group in the compound (V) as formed in the step (2) into a carboxyl group.

The hydrolysis can be conducted by conventional methods, for example, by treating the compound (V) in a solvent (e.g., alcohols such as methanol, ethanol, propanol, etc., organic acids such as acetic acid, propionic acid, etc., ethers, etc.) in the presence of an acid (preferably, an inorganic acid such as hydrochloric acid, hydrobromic acid, sulfuric acid, etc.), at a temperature between about 15° C. and 130° C. or so.

The step (4) is to produce a compound (VII) by reducing the carboxyl group in the compound (V) as formed in the step (3) into a hydroxymethyl group. The reduction can be conducted by conventional methods, for example, by converting the carboxyl group in the compound (V) into its reactive derivative (e.g., any of acid halides, mixed acid anhydrides, active esters, esters, etc.), followed by treating the resulting reactive derivative with a reducing agent (e.g., sodium borohydride, aluminium lithium hydride, etc.) in a solvent (e.g., ethers such as tetrahydrofuran, dimethoxyethane, etc.), at a temperature between about 0° C. and 100° C. or so.

The step (5) is to produce a lactone compound (VIII) by treating the compound (VII) as formed in the previous step (4) under an acidic condition. This step can be conducted under the same conditions as those for the foregoing step (3).

The step (6) is to produce an amide compound (IX) by reacting the compound (VIII) as formed in the previous step (5) with an amine. This reaction can be conducted in the absence or presence of a solvent. The solvent includes, for example, those as referred to hereinabove as employable in the foregoing step (1). The amount of the amine to be used is, for example, from 1 to 50 mols or so, preferably from 1 to 10 mols or so, relative to mol of the compound (VIII). The reaction can be conducted, for example, at a temperature falling between about 15° C. and 200° C. or so, preferably between about 50° C. and 180° C. or so. As a result of the step (6), a compound (IX) where X is a hydroxyl group is formed.

The step (7) is to obtain a compound (IIa) by converting the hydroxyl group X in the compound (IX) as formed in the previous step (6) into a removable group L.

The leaving group L includes, for example, a halogen atom (e.g., chlorine, bromine and iodine atoms, etc.), a $C_{1-4}$ alkanesulfonyloxy group (e.g., methanesulfonyloxy and ethanesulfonyloxy groups, etc.), a $C_{6-10}$ arylsulfonyloxy group (e.g., benzenesulfonyloxy and p-toluenesulfonyloxy groups, etc.), etc. For the conversion, in general, compounds corresponding to the above-mentioned removable group (e.g., thionyl chloride, thionyl bromide, methanesulfonyl chloride, benzenesulfonyl chloride, etc.) are used. The conversion can be conducted in a solvent (e.g., hydrocarbons such as benzene, toluene, etc., halogenated hydrocarbons such as dichloromethane, 1,2-dichloroethane, chloroform, etc., ethers such as tetrahydrofuran, etc., esters such as ethyl acetate, etc.). The reaction temperature falls, for example, between about 0° C. and 100° C. or so.

Some of the starting compounds (II) can also be produced in accordance with known methods for producing the corresponding compounds where Ring A and Ring B are both homocyclic rings (for example, a method described in EP-585913, etc.) or with reference thereto.

In addition, the compounds of formula (IIa) can also be produced, with reference to the above-mentioned known methods (for example, a method described in EP-481383A1, etc.), via the following compounds (XII) wherein —X‾‾‾‾‾ Y— is —CO—O—. For example, compounds of the following general formula (IIb) can be produced according to the following reaction process (2).

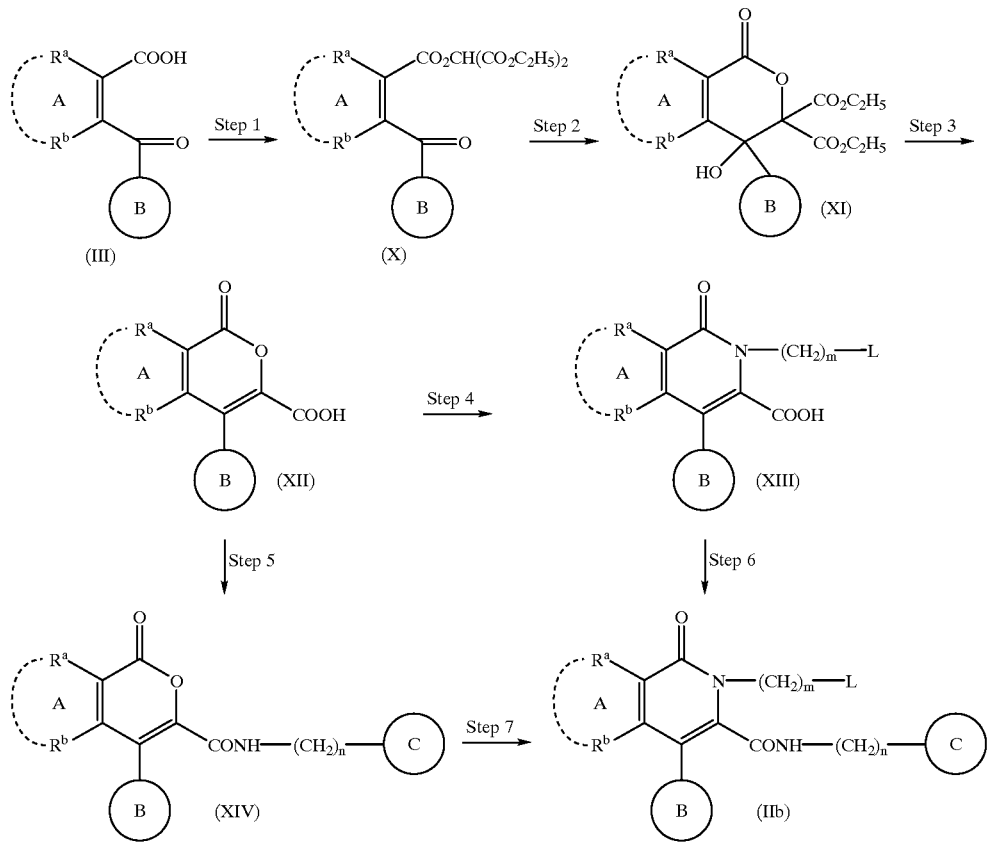

In these formulae, the symbols have the same meanings as above.

In the reaction process (2), the steps (1) through (4) can be conducted with reference to known methods for producing the corresponding compounds where Ring A and Ring B are both optionally substituted benzene rings (for example, a method described in EP-481383A1, etc.). The steps (5) and (6) are to amidate the carboxyl group in a compound (XII) and a compound (XIII)., which can be conducted in the same manner as in the step (1) in the above-mentioned reaction process (1). The step (7) is to convert the pyran ring in the compound (XIV) as formed in the step (5) into a pyridine ring, which can be conducted in the same manner as in the step (4) (see N. A. Santagati, E. Bousquet, G. Romeo, A. Garuso and A. Prato; Bolletino Chimica Farmaceutico, Vol. 125, p. 437, 1986).

Of the starting compounds (II), those of the following formula (IIc):

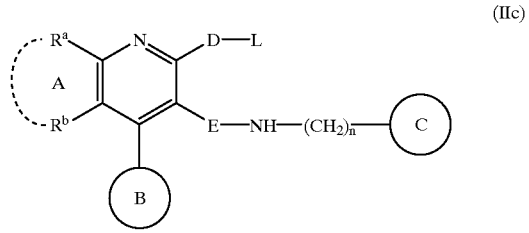

wherein —N=CC< corresponds to —X ..... Y<, and the other symbols have the same meanings as above, can be produced by the combination of known methods for producing the corresponding quinoline-skeleton compounds where Ring A and Ring B are both benzene rings (for example, methods described in EP-354994A2, EP-304063A2, etc.) and the methods for producing the above-mentioned compounds (IIa) and (IIb), etc.

Of the compounds (II), those where Ring A and/or Ring B is/are non-aromatic, nitrogen-containing heterocyclic ring (s) can be produced by reducing the corresponding aromatic rings according to the above-mentioned reduction.

The compounds (II) may form salts, which include, for example, salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, toluenesulfonic acid, etc.), etc. Where the compounds (II) have acidic group(s) such as carboxyl group(s), etc., they may also form salts with inorganic bases (e.g., alkali metals such as sodium, potassium, etc., alkaline earth metals such as calcium, magnesium, etc., ammonia, etc.) or with organic bases (e.g., tri-$C_{1-3}$ alkylamines such as trimethylamine, triethylamine, etc.).

The compounds represented by the above-mentioned general formula (I), (Ia) also can be produced by, for example, the following reaction process (3).

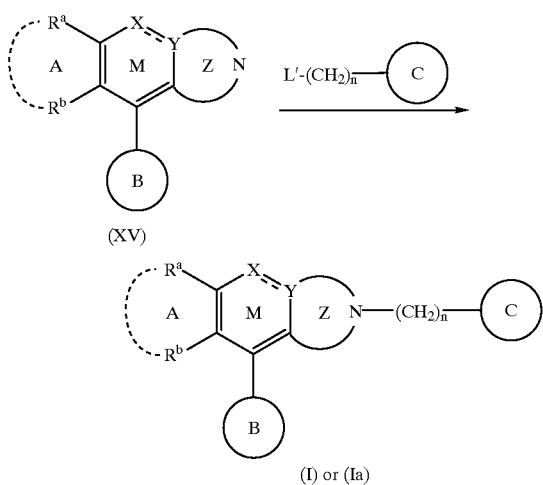

[wherein all symbols are of the same meaning as defined above, and L' stands for a halogen atom (e.g., chlorine, bromine and iodine atoms, etc.), a substituted sulfonyloxy group (e.g., methanesulfonyloxy, ethanesulfonyloxy, benzenesulfonyloxy and p-toluenesulfonyloxy groups, etc.), etc.].

The above-illustrated reaction process (3) is alkylation using an alkylating agent in the presence of a base.

The alkylation is conducted, employing approximately 1 to 3 moles each of the base and the alkylating agent relative to one mole of the compound (XV), usually in a solvent for example halogenated hydrocarbons such as dichloromethane, chloroform, etc., nitriles such as acetonitrile, etc., ethers such as dimethoxyethane, tetrahydrofuran, etc., aprotic polar solvents such as dimethylformamide, dimethylsulfoxide, hexamethylphosphoramide, etc.

Addition of a base to the reaction system advantageously promotes the reaction. As the base, for example, advantageously employed is any of inorganic bases (alkali metal hydroxides such as sodium hydroxide, potassium hydroxide, etc.; alkali metal hydrogencarbonates such as sodium hydrogencarbonate, potassium hydrogencarbonate, etc.; alkali metal carbonates such as sodium carbonate, potassium carbonate, etc.; alkali metal hydrides such as sodium hydride, potassium hydride, etc.; sodium amide; alkoxides such as sodium methoxide, sodium ethoxide, etc.), and organic bases (amines such as trimethylamine, triethylamine, diisopropylethylamine, etc.; cyclic amines such as pyridine, etc.).

As the alkylating agent, use is made of, for example, substituted halides (e.g. chloride, bromide and iodide) and a substituted sulfonyloxy group (e.g., methanesulfonyloxy, ethanesulfonyloxy, benzensulfonyloxy and p-toluenesulfonyloxy groups, etc.), etc.

While the reaction conditions vary with the combination of the base and the alkylating agent then employed, it is preferable to conduct the reaction usually at 0° C. to room temperature for about 1–10 hours.

In the reactions of producing the final compounds and the starting compounds, if the raw materials used have, as substituent(s), amino group(s), carboxyl group(s) and/or hydroxyl group(s), such groups may optionally be protected by ordinary protecting groups such as those generally employed in peptide chemistry, etc. In such cases, if desired, the protecting groups are optionally removed after the reactions to obtain the intended compounds.

The protecting group for amino groups includes, for example, a $C_{1-6}$ alkylcarbonyl group (e.g., formyl, methyl-carbonyl and ethylcarbonyl groups, etc.), a phenylcarbonyl group, a $C_{1-6}$ alkyl-oxycarbonyl group (e.g., methoxycarbonyl and ethoxycarbonyl groups, etc.), an aryloxycarbonyl group (e.g., phenyloxycarbonyl group, etc.), a $C_{7-10}$ aralkyl-carbonyl group (e.g., phenyl-$C_{1-4}$ alkyl-carbonyl such as benzylcarbonyl group, etc.), a trityl group, a phthaloyl group, etc. These protecting groups may optionally be substituted. As substituents for these protecting groups, for example, mentioned are a halogen atom (e.g., fluorine, chlorine, bromine and iodine atoms), a $C_{1-6}$ alkyl-carbonyl group (e.g., methylcarbonyl, ethylcarbonyl and butylcarbonyl groups, etc.), a nitro group, etc. The number of the substituents is from 1 to 3 or so.

The protecting group for carboxyl groups includes, for example, $C_{1-6}$ alkyl group (e.g., methyl, ethyl, n-propyl, i-propyl, n-butyl and tert-butyl groups, etc.), a phenyl group, a trityl group, a silyl group, etc. These protecting groups may optionally be substituted. As substituents for these protecting groups, for example, mentioned are a halogen atom (e.g., fluorine, chlorine, bromine and iodine atoms), a $C_{1-6}$ alkylcarbonyl group (e.g., formyl, methylcarbonyl, ethylcarbonyl and butylcarbonyl groups, etc.), a nitro group, etc. The number of the substituents is from 1 to 3 or so.

The protecting group for hydroxyl groups includes, for example, $C_{1-6}$ alkyl group (e.g., methyl, ethyl, n-propyl, i-propyl, n-butyl and tert-butyl groups, etc.), a phenyl group, a $C_{7-10}$ aralkyl group (e.g., benzyl group, etc.), a $C_{1-6}$ alkylcarbonyl group (e.g., formyl, methylcarbonyl and ethylcarbonyl groups, etc.), an aryloxycarbonyl group (e.g., phenyloxycarbonyl group, etc.), a $C_{7-10}$ aralkyl-carbonyl group (e.g., benzyloxycarbonyl group, etc.), a pyranyl group, a furanyl group, a silyl group, etc. These protecting groups may optionally be substituted. As substituents for these protecting groups, for example, mentioned are a halogen atom (e.g., fluorine, chlorine, bromine and iodine atoms), a $C_{1-6}$ alkylcarbonyl group, a phenyl group, a $C_{7-10}$ aralkyl group, a nitro group, etc. The number of the substituents is from 1 to 4 or so.

To remove the protecting groups, known methods are employable or are referred to. For example, employable are methods of treating the protected compounds with acids, bases, reducing agents, ultraviolet rays, hydrazine, phenylhydrazine, sodium N-methyldithiocarbamate, tetrabutylammonium fluoride, palladium acetate or the like.

The compounds (I) and (Ia) thus produced according to the methods mentioned hereinabove can be isolated and purified by ordinary separation means, for example, by recrystallization, distillation, chromatography, etc. Where the compounds (I) thus produced are of free forms, they can be converted into their salts in accordance with or with reference to known methods (for example, neutralization, etc.). On the contrary, if the compounds (I) are obtained as their salts, they can be converted into the corresponding free forms in accordance with or with reference to known methods.

The compounds (I) and (Ia) or salts thereof of the present invention have tachykinin receptor (especially SP and/or NKA receptor(s)) antagonistic activity in vitro, and have the function of inhibiting the tracheal plasma extravasation induced by capsaicin (in vivo). Capsaicin (a main ingredient of the burning taste of red pepper) is known as a substance that liberates endogenous neuropeptides, such as SP, NKA and calcitonin gene-related peptide(CGRP) by stimulating C-fiber primary sensory nerve that contains such neuropeptides. Thus, the inhibitory action of the plasma extravasation of the compounds (I) and (Ia) or salt thereof of the present invention is considered to be based on the antagonistic activity toward tachykinin receptor.

In addition, the compounds (I) and (Ia) or salts thereof of the present invention are safe as having low toxicity.

Therefore, the compounds (I) and (Ia) or salts thereof of the present invention, thus having such an excellent tachykinin receptor antagonistic effect, are usable as safe medicines for preventing and treating various disorders in mammals (e.g., mice, rats, hamsters, rabbits, cats, dogs, bovines, sheep, monkeys, man, etc.), such as inflammations or allergic disorders (e.g., atopy, dermatitis, herpes, proriasis, asthma, bronchitis, expectoration, rhinitis, rheumatoid arthritis, osteoarthritis, osteoporosis, multiple sclerosis, conjunctivitis, cystitis, etc.), pain, migraine, neuralgia, pruritus, cough, and additionally disorders of central nervous systems [e.g., schizophrenia, Parkinson's disease, psychosomatic disorders, dementia (e.g., Alzheimer's disease, etc.), etc.], digestive diseases (for example, irritable bowel syndrome, ulcerative colitis, Crohn's disease, diseases caused by a spiral urease-positive gram-negative bacterium such as *Helicobacter pylori*, etc.), emesis, disorders of micturition (for example, pollakisuria, urinary incontinence etc.), disturbances of circulation (for example, angina pectories, hypertension, cardiac insufficiency, thrombosis, etc.) and immunopathy, etc. More particularly, the compounds (I) and (Ia) or salts thereof of the present invention are usable as a tachykinin receptor antagonist and as an ameliorative preparation for disorders of micturition such as pollakisuria urimary incontinence, etc., and even as medicines for treating such disorders of micturition.

Pharmaceutical preparations comprising compounds (I) and (Ia) or salts thereof of the present invention may be in any solid forms of powders, granules, tablets, capsules, etc., and in any liquid forms of syrups, emulsions, injections, etc.

The preventive and remedial preparations of the present invention can be produced by any conventional methods of, for example, blending, kneading, granulation, tabletting, coating, sterilization, emulsification, etc., in accordance with the forms of the preparations to be produced. For the production of such pharmaceutical preparations, for example, referred to are the particular items in the general remarks for pharmaceutical preparations in the Japanese Pharmacopeia.

In the pharmaceutical preparations of the present invention, the content of the compounds (I) and (Ia) or salts thereof is, though varying depending on the forms of the preparations, generally from 0.01 to 100% by weight or so, preferably from 0.1 to 50% by weight or so, more preferably from 0.5 to 20% by weight or so, relative to the total weight of each preparation.

Where the compounds (I) and (Ia) or salts thereof of the present invention are used in medicines such as those mentioned above, they are, either directly or after having been mixed with suitable, pharmaceutically-acceptable carriers, for example, vehicles (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinyl pyrrolidone, etc.), lubricants (e.g., stearic acid, magnesium stearate, calcium stearate, talc, etc.), disintegrators (e.g., calcium carboxymethyl cellulose, talc, etc.), diluents (e.g., water for injection, physiological saline, etc.) and optionally with additives (e.g., stabilizer, preservative, colorant, fragrance, dissolution aid, emulsifier, buffer, isotonic agent, etc.), etc., by ordinary methods, formulated into solid preparations such as powders, fine granules, granules, tablets, capsules, etc., or into liquid preparations such as injections, etc., for peroral or parenteral administration. The dose of the pharmaceutical preparation of the present invention varies, depending on the kind of the compounds (I) and (Ia) or pharmaceutically-acceptable salts thereof, the administration route, the condition and the age of patients, etc. For example, the dose for oral administration of the pharmaceutical preparation to an adult patient suffering from disorders of micturition is, in general, from about 0.005 to 50 mg/kg/day, preferably from about 0.05 to 10 mg/kg/day, more preferably from about 0.2 to 4 mg/kg/day, in terms of the compound (I) or (Ia) or its salt, which may be administered once a day or in two or three portions a day.

The compounds (I) and (Ia) or salts thereof of the present invention may be optionally blended with any desired amounts of any other pharmaceutically-active ingredients to formulate pharmaceutical preparations. Such active ingredients include, for example, drugs for central nervous systems (e.g., imipramine, etc.), anti-cholinergic drugs (e.g., oxybutynin, etc.), $\alpha_1$-receptor-blocking drugs (e.g., tamsulosin, etc.), muscle relaxants (e.g., baclofen, etc.), potassium channel-opening drugs (e.g., nicorandil, etc.), potassium channel-blocking drugs (e.g., nifedipine, etc.), etc.

The compounds (I) and (Ia) or salts thereof of the present invention have a high tachykinin receptor antagonistic effect, especially a high substance P receptor antagonistic effect, while having low toxicity, and are safe as medicines. Therefore, the above-mentioned compounds (I) and (Ia) or salts thereof are usable in pharmaceutical compositions, tachykinin receptor antagonists and ameliorative preparations for dysuria.

The present invention will be described in more detail hereinunder, with reference to Examples and Referentce Examples. However, the present invention is not restricted by these examples, and changes and modifications can be made within the range which does not deviate the scope of the present invention.

Elution in the column chromatography in the following Reference Examples and Examples was conducted under observation by TLC (thin layer chromatography), unless otherwise specifically indicated. In the TLC observation, 60F$_{254}$ produced by Merck Co. was used as the TLC plate, and the solvent employed in the column chromatography was used as the developing eluent. For the detection, a UV detector was used. As silica gel for the column chromatography, Silica Gel 60 (70–230 mesh) produced by Merck Co. was used. Room temperature as referred to hereinunder generally means temperatures falling between about 10° C. and about 35° C. For dring the extract solutions, sodium sulfate or magnesium sulfate was used.

The meanings of the abbreviations as used in the following Examples and Referential Examples are as follows:

NMR: Nuclear magnetic resonance spectrum
EI-MS: Electron impact mass spectrum
SI-MS: Secondary ionization mass spectrum
DMF: Dimethylformamide
THF: Tetrahydrofuran
DMSO: Dimethylsulfoxide
Hz: Herz
J: coupling constant
m: multiplet
q: quartet
t: triplet
d: doublet
s: singlet
b: broad
like: approximate

Example 1
7-[3,5-Bis(trifluoromethyl)benzyl]-6,7,8,9-tetrahydro-5-(4-methylphenyl)-6,11-dioxo-11H-pyrazino[2,1-g][1,7]naphthyridine A mixture of the compound (200 mg) as obtained in Reference Example 1, triethylamine (0.20 ml), methanesulfonyl chloride (0.10 ml) and dichloromethane (10 ml) was stirred at 0° C. for 2 hours. Ethyl acetate was added to the reaction mixture, which was then washed with water and dried. The solvent was evaporated to give N-[3,5-bis(trifluoromethyl)benzyl]-7,8-dihydro-7-(2-methanesulfonyloxyethyl)-5-(4-methylphenyl)-8-oxo-6-pyrido[3,4-b]pyridinecarboxamide. This compound was dissolved in DMF (5 ml), and sodium hydride (60% oily) (30 mg) was added thereto and stirred for 1.5 hours at room temperature. The reaction mixture was diluted with ethyl acetate, washed successively with water, diluted hydrochloric acid and water, and dried. After the solvent was removed by distillation, the entitled compound was obtained as colorless crystals (109 mg).

m.p. 270–271° C. (recrystallized from ethyl acetate-ethyl ether)

NMR (200 MHz, $CDCl_3$) ppm: 2.46 (3H, s), 3.67 (2H, t like, J=5.4 Hz), 4.51 (2H, t like, J=5.4 Hz), 4.81 (2H, s), 7.13 (2H, d, J=8.1 Hz), 7.33 (2H, d, J=8.1 Hz), 7.52 (1H, dd, J=8.4, 4.4 Hz), 7.64 (1H, dd, J=8.4, 1.6 Hz), 7.70 (2H, s), 7.84 (1H, s), 8.97 (1H, dd, J=4.4, 1.6 Hz)

Elemental Analysis for $C_{27}H_{19}N_3O_2F_6$: Calcd.(%): C, 61.02; H, 3.60;.N, 7.91 Found (%): C, 61.07; H, 3.50; N, 7.85

Example 2
7-[3,5-Bis(trifluoromethyl)benzyl]-6,7,8,9,10,12-hexahydro-5-(4-methylphenyl)-6,12-dioxo[1,4]diazepino[2,1-g][1,7]naphthyridine A mixture of N-[3,5-bis(trifluoromethyl)benzyl]-7-(3-chloropropyl)-7,8-dihydro-5-(4-methylphenyl)-8-oxo-6-pyrido[3,4-b]pyridinecarboxamide (66 mg), sodium hydride (60% oily) (84 mg) and THF (3 ml) was stirred at room temperature for 14 hours. 2N-HCl was added to the reaction mixture, which was then made basic with aqueous potassium carbonate and thereafter extracted with ethyl acetate. The extract was washed with water and dried, and the solvent was removed by distillation. Thus, the entitled compound was obtained as colorless crystals (35 mg).

m.p. 194–195° C. (recrystallized from ethyl acetate-isopropyl ether)

NMR (200 MHz, $CDCl_3$) ppm: 2.16 (2H, m), 2.42 (3H, s), 3.25–3.70 (3H, m), 4.12 (1H, d, J=15 Hz), 5.34 (1H, d, J=15 Hz), 5.52 (1H, m), 6.93 (1H, d, J=8.2 Hz), 7.20 (1H, d, J=8.2 Hz), 7.30–7.45 (2H, m), 7.51 (1H, dd, J=8.4,4.4 Hz), 7.62 (2H, s), 7.70 (1H, dd, J=8.4, 1.6 Hz), 7.84 (1H, s), 8.93 (1H, dd, J=4.4, 1.6 Hz)

Elemental Analysis for $C_{28}H_{21}N_3O_2F_6$: Calcd.(%): C, 61.65; H, 3.88; N, 7.70 Found (%): C, 61.29; H, 4.06; N, 7.61

Example 3
7-[3,5-Bis(trifluoromethyl)benzyl]-6,7,8,9,10,11-hexahydro-5-(4-methylphenyl)-6,13-dioxo-13H-[1,4]diazocino[2,1-g][1,7]naphthyridine The compound as obtained in Reference Example 5 was reacted and treated in the same manner as in Example 1 to obtain the entitled compound as colorless crystals.

m.p. 192–193° C. (recrystallized from ethyl acetate-isopropyl ether)

NMR (200 MHz, $CDCl_3$) ppm: 1.7–2.5 (4H, m), 2.37 (3H, s), 3.25 (1H, m), 3.40–3.72 (2H, m), 4.01 (1H, d, J=15 Hz), 5.13 (1H, dd, J=14, 5.4 Hz), 5.46 (1H, d, J=15 Hz), 6.85 (1H, d, J=7.9 Hz), 7.05 (1H, d, J=7.9 Hz), 7.26 (1H, d, J=7.8 Hz), 7.34 (1H, d, J=7.8 Hz), 7.42– 7.60 (2H, m), 7.47 (2H, s), 7.81 (1H, s), 8.92 (1H, m)

Example 4
6,7,8,9,10,12-Hexahydro-7-(2-methoxybenzyl)-5-(4-methylphenyl)-6,12-dioxo[1,4]diazepino[2,1-g)[1,7]naphthyridine The compound as obtained in Reference Example 6 was reacted and treated in the same manner as in Example 1 to obtain the entitled compound as colorless crystals.

m.p. 264–266° C. (recrystallized from ethyl acetate-ethyl ether)

NMR (200 MHz, $CDCl_3$) ppm: 1.7–2.1 (2H, m), 2.43 (3H, s), 3.25–3.52 (3H, m), 3.84 (3H, s), 4.67 (2H, s), 5.39 (1H, dd, J=14, 5.8 Hz), 6.85–7.00 (3H, m), 7.10–7.22 (2H, m), 7.22–7.44 (3H, m), 7.48 (1H, dd, J=8.4, 4.4 Hz), 7.72 (1H, dd, J=8.4, 1.4 Hz), 8.90 (1H, dd, J=4.4, 1.4 Hz)

Example 5
6,7,8,9,10,11-Hexahydro-7-(2-methoxybenzyl)-5-(4-methylphenyl)-6,13-dioxo-13H-(1,4]diazocino[2,1-g][1,7]naphthyridine The compound as obtained in Reference Example 7 was reacted and treated in the same manner as in Example 1 to obtain the entitled compound as colorless crystals.

m.p. 235–235° C. (recrystallized from ethyl acetate)

NMR (200 MHz, $CDCl_3$) ppm: 1.6–2.3 (4H, m), 2.46 (3H, s), 3.15–3.30 (1H, m), 3.38–3.65 (2H, m), 3.80 (3H, s), 4.24 (1H, d, J=15 Hz), 5.04 (1H, d, J=15 Hz), 5.13 (1H, dd, J=15, 6.4 Hz), 6.25 (1H, dd, J=7.6, 1.4 Hz), 6.63 (1H, dt, $J_d$=0.5 Hz, $J_t$=7.6 Hz), 6.82 (1H, d, J=7.4 Hz), 6.96 (1H, dd, J=7.6, 2.0 Hz), 7.11–7.34 (3H, m), 7.38–7.47 (1H, m), 7.47 (1H, dd, J=8.3, 4.3 Hz), 7.62 (1H, dd, J=8.3, 1.7 Hz), 8.90 (1H, dd, J=4.3, 1.7 Hz)

Example 6
7-[3,5-Bis(trifluoromethyl)benzyl]-6,7,8,9,10,11,12,14-octahydro-5-(4-methylphenyl)-6,14-dioxo[1,4]diazonino[2,1-g][1,7]naphthyridine The compound as obtained in Reference Example 8 was reacted and treated in the same manner as in Example 1 to obtain the entitled compound as colorless crystals.

m.p. 177–179° C. (recrystallized from ethyl acetate-isopropyl ether)

NMR (200 MHz, $CDCl_3$) ppm: 1.45–1.95 (4H, m), 2.10 (2H, m), 2.33 (3H, s), 3.06–3.24 (1H, m), 3.32–3.56 (2H, m), 3.86 (1H, d, J=15 Hz), 4.95 (1H, dt, $J_d$=15 Hz, $J_t$=4.8 Hz), 5.38 (1H, d, J=15 Hz), 6.86 (1H, dd, J=8.0, 1.5 Hz), 7.00 (1H, d, J=8.0 Hz), 7.17 (1H, d, J=8.2 Hz), 7.29 (1H, dd, J=8.2, 1.5 Hz), 7.40–7.54 (2H, m), 7.44 (2H, s), 7.79 (1H, s), 8.89 (1H, dd, J=3.8, 2.0 Hz)

Example 7
7-[3,5-Bis(trifluoromethyl)benzyl]-6,7,8,9,10,12-hexahydro-6,12-dioxo-5-phenyl[1,4)diazepino[2,1-g][1,7]naphthyridine The compound as obtained in Reference Example 9 was reacted and treated in the same manner as in Example 1 to obtain the entitled compound as colorless crystals.

m.p. 244–245° C. (recrystallized from ethyl acetate-THF-ethyl)

NMR (200 MHz, $CDCl_3$) ppm: 2.00–2.25 (2H, m), 3.25–3.70 (3H, m), 4.15 (1H, d, J=15 Hz), 5.30 (1H, d, J=15 Hz), 5.52 (1H, m), 7.05 (1H, d, J=7.4 Hz), 7.3–7.7 (6H, m), 7.62 (2H, s), 7.84 (1H, s), 8.93 (1H, dd, J=4.2, 1.6 Hz)

Example 8
7-[3,5-Bis(trifluoromethyl)benzyl]-6,7,8,9,10,11-hexahydro-6,13-dioxo-5-phenyl-13H-[1,4]diazocino(2,1-g][1,7]naphthyridine The compound as obtained in Reference Example 10 was reacted and treated in the same manner as in Example 1 to obtain the entitled compound as colorless crystals.

m.p. 205–206° C. (recrystallized from ethyl acetate-ethyl ether)

NMR (200 MHz, CDCl$_3$) ppm: 1.70–2.35 (4H, m), 3.18–3.36 (1H, m), 3.4–3.7 (2H, m), 3.98 (1H, d, J=15 Hz), 5.14 (1H, dd, J=14, 5.8 Hz), 5.43 (1H, d, J=15 Hz), 6.94 (1H, d, J=7.3 Hz), 7.19 (1H, t, J=7.3 Hz), 7.3–7.6 (5H, m), 7.44 (2H, s), 7.79 (1H, s), 8.91 (1H, dd, J=4.0, 1.8 Hz)

Example 9

7-[3,5-Bis(trifluoromethyl)benzyl]-6,7,8,9,10,11-hexahydro-5-(4-methylphenyl)-6,13-dioxo-13H-[1,4]diazocino[1,2-b][2,7]naphthyridine The compound as obtained in Reference Example 11 was reacted and treated in the same manner as in Example 1 to obtain the entitled compound as colorless crystals.

m.p. 231–233° C. (recrystallized from THF-isopropyl ether)

NMR (200 MHz, CDCl$_3$) ppm: 1.7–2.3 (4H, m), 2.37 (3H, s), 3.2–3.7 (3H, m), 4.00 (1H, d, J=15 Hz), 5.05 (1H, dd, J=15, 6.2 Hz), 5.44 (1H, d, J=15 Hz), 6.83 (1H, dd, J=7.8, 1.6 Hz), 6.98 (1H, d, J=5.4 Hz), 7.04 (1H, d, J=7.8 Hz), 7.25 (1H, d, J=7.8 Hz), 7.33 (1H, dd, J=7.8, 1.6 Hz), 7.46 (2H, s), 7.81 (1H, s), 8.64 (1H, d, J=5.4 Hz), 9.68 (1H, s)

Example 10

7-[3,5-Bis(trifluoromethyl)benzyl]-1,2,3,4,6,7,8,9,10,11-decahydro-2-methyl-5-(4-methylphenyl)-6,13-dioxo-13H-[1,4]diazocino[1,2-b][2,7]naphthyridine A mixture of the compound (250 mg) as obtained in Example 9, iodomethane (3 ml) and ethyl acetate (6 ml) was heated under reflux for 1.5 hours. After the solvent was removed by distillation, the residue was dissolved in methanol (15 ml). Sodium borohydride (50 mg) was added to the resulting solution at 0° C. with stirring, and the mixture was then further stirred at 0° C. for one hour and thereafter concentrated. Ethyl acetate was added to the resulting concentrate, which was then washed with water and dried. Then, the solvent was removed by distillation. The residue was dissolved in methanol (15 ml), and 10% palladium-carbon (50% hydrous) (100 mg) was added thereto and stirred in a hydrogen atmosphere at room temperature for 3 hours. The catalyst was removed by filtration, and the solvent was removed from the filtrate by distillation. The residue was subjected to column chromatography (ethyl acetate—ethyl acetate:methanol=4:1) using silica gel, and the entitled compound was obtained as pale yellow crystals (150 mg).

m.p. 233–235° C. (recrystallized from THF-ethyl acetate-isopropyl ether)

NMR (200 MHz, CDCl$_3$) ppm: 1.7–2.6 (8H, m), 2.31 (3H, s), 2.47 (3H, s), 3.1–3.8 (5H, m), 3.95 (1H, d, J=15 Hz), 4.93 (1H, dd, J=14, 6.2 Hz), 5.41 (1H, d, J=15 Hz), 6.72 (1H, d, J=7.8 Hz), 6.98 (1H, d, J=7.8 Hz), 7.19 (2H, s), 7.42 (2H, s), 7.78 (1H, s)

Example 11

4-[3,5-Bis(trifluoromethyl)benzyl]-2,3,4,5-tetrahydro-5-oxo-6-phenylpyrido[3,2-f][1,4]oxazepine Sodium hydride (60% oily) (60 mg) was added to a THF (15 ml) solution of N-[3,5-bis(trifluoromethyl)benzyl]-2-chloro-N-(2-hydroxyethyl)-4-phenyl-3-pyridinecarboxamide (Reference Example 12) (348 mg) and the mixture was stirred for 2 hours while heating under reflux. Ethyl acetate was added to the reaction mixture, which was then washed with water and dried. After the solvent was removed by distillation, the entitled compound was obtained as colorless crystals (278 mg).

m.p. 200–201° C. (recrystallized from ethanol-hexane)

NMR (200 MHz, CDCl$_3$) ppm: 3.70 (2H, t, J=5.8 Hz), 4.47 (2H, t, J=5.8 Hz), 4.88 (2H, s), 7.24 (1H, d, J=5.2 Hz), 7.25–7.55 (5H, m), 7.80 (2H, s), 7.86 (1H, s), 8.44 (1H, d, J=5.2 Hz)

EI-MS m/z: 466 (M$^+$) [(C$_{23}$H$_{16}$N$_2$O$_2$F$_6$)$^+$]

Example 12

(9R)-7-[3,5-Bis(trifluoromethyl)benzyl]-6,7,8,9,10,12-hexahydro-9-methyl-5-(4-methylphenyl)-6,12-dioxo[1,4]diazepino[2,1-g][1,7]naphthyridine A mixture of the compound (700 mg) as obtained in Reference Example 13, triethylamine (0.41 ml), methanesulfonyl chloride (0.224 ml) and THF (15 ml) was stirred at room temperature for 30 minutes, and a saturated aqueous sodium hydrogencarbonate solution (15 ml) was added thereto and again stirred for 30 minutes at room temperature. The reaction mixture was extracted with ethyl acetate, the extract was washed with diluted hydrochloric acid and a saturated aqueous sodium chloride solution and dried, and the solvent was removed by distillation. The residue was dissolved in THF (15 ml), and then sodium hydride (60% oily) (76 mg) was added thereto and stirred at room temperature for 1.5 hours. The reaction mixture was diluted with ethyl acetate, washed with diluted hydrochloric acid, aqueous sodium carbonate and a saturated aqueous sodium chloride solution and then dried, and the solvent was removed by distillation. The residue was subjected to column chromatography (ethyl acetate:methanol=9:1) using silica gel, and the entitled compound was obtained as colorless crystals (408 mg).

m.p. 179–180° C. (recrystallized from ethyl acetate-isopropyl ether)

NMR (200 MHz, CDCl$_3$) ppm: 1.05 (2H×2/3, d, J=7.0 Hz), 1.22 (3H×1/3, d, J=7.0 Hz), 2.39 (3H×1/3, s), 2.42 (3H×2/3, s), 2.52 (1H, m), 3.0–3.3 (2H, m), 3.48 (1H×2/3, dd, J=14, 4.6 Hz), 3.71 (1H×1/3, dd, J=16, 5.2 Hz), 4.06 (1H×1/3, d, J=15 Hz), 4.12 (1H×2/3, d, J=15 Hz), 5.28–5.65 (2H, m), 6.83 (1H×1/3, d, J=7.4 Hz), 6.96 (1H×2/3, d, J=7.6 Hz), 7.09 (1H×1/3, d, J=7.4 Hz), 7.20 (1H×2/3,d, J=7.6 Hz), 7.35(2H,m), 7.42–7.75(4H,m), 7.83(1H,s), 8.92(1H,d,J=3.6Hz) Elemental Analysis for C$_{29}$H$_{23}$N$_3$O$_2$F$_6$: Calcd.(%): C, 62.25; H, 4.14; N, 7.51. Found (%): C, 62.00; H, 4.08; N, 7.24. [α]$_D$: −60.2° (c=0.348, MeOH)

Example 13

(9S)-7-[3,5-Bis(trifluoromethyl)benzyl]-6,7,8,9,10,12-hexahydro-9-methyl-6,12-dioxo-5-phenyl[1,4]diazepino[2,1-g][1,7]naphthyridine The compound as obtained in Reference Example 14 was reacted and treated in the same manner as in Example 12 to obtain the entitled compound as colorless crystals. m.p. 150–152° C. (recrystallized from ethyl acetate-isopropyl ether) NMR(200 MHz, CDCl$_3$) ppm: 1.06(3H×2/3,d,J=7.0 Hz), 1.21(3H×1/3,d,J=7.0 Hz), 2.50(1H,m), 3.05–3.30(2H, m), 3.49(1H×2/3,dd,J=14,4.6 Hz), 3.72(1H×1/3,dd,J=16,5.4 Hz), 4.07(1H×1/3,d,J=15 Hz), 4.14(1H×2/3,d,J=15 Hz), 5.25–5.62(2H,m), 6.94(1H×1/3,d,J=7.6 Hz), 7.08(1H×2/3,d,J=7.4 Hz), 7.2–7.7(8H,m), 7.83(1H,s), 8.93(1H,dd,J=4.3,1.7 Hz) Elemental Analysis for C$_{28}$H$_{21}$N$_3$O$_2$F$_6$: Calcd.(%): C, 61.65; H, 3.88; N, 7.70. Found (%): C, 61.33; H, 3.89; N, 7.51. [α]$_D$: +69.80 (c=0.353, MeOH)

Example 14

(9S)-7-[3,5-Bis(trifluoromethyl)benzyl]-6,7,8,9,10,12-hexahydro-9-methyl-5-(4-methylphenyl)-6,12-dioxo[1,4]diazepino[2,1-g][1,7]naphthyridine The compound as obtained in Reference Example 15 was reacted and treated in the same manner as in Example 12 to obtain the entitled compound as colorless crystals. m.p. 179–180° C. (recrystallized from ethyl acetate-isopropyl ether) NMR (200 MHz, CDCl$_3$) ppm: Same as the spectrum of the compound of Example 12 Elemental Analysis for C$_{29}$H$_{23}$N$_3$O$_2$F$_6$: Calcd.(%): C, 62.25; H, 4.14; N, 7.51. Found (%): C, 61.94; H, 4.16; N, 7.24. [α]$_D$: +58.2° (c=0.353, MeOH)

Example 15

(+/−)-7-[3,5-Bis(trifluoromethyl)benzyl]-6,7,8,9,10,11-hexahydro-9-methyl-6,13-dioxo-5-phenyl-13H-[1,4]diazocino[2,1-g][1,7]naphthyridine Methanesulfonyl chloride (0.29 ml) was added to a THF (15 ml) solution of the compound (830 mg) as obtained in Reference Example 16 and triethylamine (0.56 ml) with stirring and cooling with ice. The resulting mixture was stirred for 50 minutes, while still cooling with ice, and then a saturated aqueous sodium hydrogencarbonate solution (15 ml) was added thereto and again stirred for 40 minutes at room temperature. The reaction mixture was extracted with ethyl acetate. The extract was washed with diluted hydrochloric acid and a saturated aqueous sodium chloride solution and dried, and then the solvent was removed by distillation. The residue was dissolved in THF (25 ml), and sodium hydride (60% oily) (90 mg) was added thereto and stirred for one hour with heating under reflux. The reaction mixture was diluted with ethyl acetate, washed with diluted hydrochloric acid, aqueous sodium carbonate and a saturated sodium chloride solution, and then dried. After the solvent was removed by distillation, the entitled compound was obtained as colorless crystals (460 mg). m.p. 257–258° C. (recrystallized from ethyl acetate-ethyl ether) NMR(200 MHz, CDCl$_3$) ppm: 0.92(3H,d,J=6.6 Hz), 1.73(1H,m), 1.95–2.40(2H,m), 2.98(1H,d,J=15 Hz), 3.30–3.65(2H,m), 3.97(1H,d,J=15 Hz), 5.11(1H,dd,J=14,5.9 Hz), 5.43(1H,d, J=15 Hz), 6.93(1H,d,J=7.6 Hz), 7.19(1H,dd,J=7.6,7.0 Hz), 7.3–7.6(7H,m), 7.81(1H,s), 8.91(1H,dd,J=4.0,2.0 Hz) Elemental Analysis for C$_{29}$H$_{23}$N$_3$O$_2$F$_6$: Calcd.(%): C, 62.25; H, 4.14; N, 7.51. Found (%): C, 61.93; H, 4.05; N, 7.57.

Example 16

(+/−)-7-[3,5-Bis(trifluoromethyl)benzyl]-6,7,8,9,10,11-hexahydro-9-methyl-5-(4-methylphenyl)-6,13-dioxo-13H-[1,4]diazocino[2,1-g][1,7]naphthyridine The compound as obtained in Reference Example 17 was reacted and treated in the same manner as in Example 15 to obtain the entitled compound as colorless crystals. m.p. 280–281° C. (recrystallized from ethyl acetate-THF-isopropyl ether) NMR(200 MHz, CDCl$_3$) ppm: 0.91(3H,d, J=6.8 Hz), 1.73(1H,m), 1.95–2.40(2H,m), 2.37(3H,s), 2.97 (1H,d,J=15 Hz), 3.35–3.62(2H,m), 3.99(1H,d,J=15 Hz), 5.10(1H,dd,J=14,5.3 Hz), 5.46(1H,d,J=15 Hz), 6.83(1H,dd, J=7.8,1.6 Hz), 7.05(1H,d,J=7.8 Hz), 7.25(1H,d,J=7.8 Hz), 7.34(1H,dd,J=7.8,1.6 Hz), 7.46(1H,dd,J=8.4,4.2 Hz), 7.47 (2H,s), 7.55(1H,dd,J=8.4,1.8 Hz), 7.81(1H,s), 8.91(1H,dd, J=4.2,1.8 Hz) Elemental Analysis for C$_{30}$H$_{25}$N$_3$O$_2$F$_6$: Calcd.(%): C, 62.83; H, 4.39; N, 7.33. Found (%): C, 62.61; H, 4.21; N, 7.12.

Example 17

(9R)-7-[3,5-Bis(trifluoromethyl)benzyl]-6,7,8,9,10,11-hexahydro-9-methyl-6,13-dioxo-5-phenyl-13H-[1,4]diazocino[2,1-g][1,7]naphthyridine The compound as obtained in Reference Example 18 was reacted and treated in the same manner as in Example 15 to obtain the entitled compound as colorless crystals. m.p. 245–247° C. (recrystallized from ethyl acetate-isopropyl ether) NMR (200 MHz, CDCl$_3$) ppm: Same as the spectrum of the compound of Example 15 [α]$_D$: +133.8° (c=0.51, MeOH) Elemental Analysis for C$_{29}$H$_{23}$N$_3$O$_2$F$_6$: Calcd.(%): C, 62.25; H, 4.14; N, 7.51. Found (%): C, 62.13; H, 4.13; N, 7.40.

Example 18

(9R)-7-[3,5-Bis(trifluoromethyl)benzyl]-6,7,8,9,10,11-hexahydro-9-methyl-5-(4-methylphenyl)-6,13-dioxo-13H-[1,4]diazocino[2,1-g][1,7]naphthyridine The compound as obtained in Reference Example 19 was reacted and treated in the same manner as in Example 15 to obtain the entitled compound as colorless crystals. m.p. 226–228° C. (recrystallized from ethyl acetate-isopropyl ether) NMR (200 MHz, CDCl$_3$) ppm: Same as the spectrum of the compound of Example 16 [α]$_D$: +109.4° (c=0.541, MeOH). Elemental Analysis for C$_{30}$H$_{25}$N$_3$O$_2$F$_6$: Calcd.(%): C, 62.83; H, 4.39; N, 7.33. Found (%): C, 62.55; H, 4.56; N, 7.10.

Example 19

(9S)-7-[3,5-Bis(trifluoromethyl)benzyl]-6,7,8,9,10,11-hexahydro-9-methyl-6,13-dioxo-5-phenyl-13H-[1,4]diazocino[2,1-g][1,7]naphthyridine The compound as obtained in Reference Example 20 was reacted and treated in the same manner as in Example 15 to obtain the entitled compound as colorless crystals. m.p. 242–244° C. (recrystallized from ethyl acetate-isopropyl ether) NMR (200 MHz, CDCl$_3$) ppm: Same as the spectrum of the compound of Example 15 [α]$_D$: −130.4° (c=0.496, MeOH). Elemental Analysis for C$_{29}$H$_{23}$N$_3$O$_2$F$_6$: Calcd.(%): C, 62.25; H, 4.14; N, 7.51. Found (%): C, 62.07; H, 4.15; N, 7.36.

Example 20

(9S)-7-[3,5-Bis(trifluoromethyl)benzyl]-6,7,8,9,10,11-hexahydro-9-methyl-5-(4-methylphenyl)-6,13-dioxo-13H-[1,4]diazocino[2,1-g][1,7]naphthyridine The compound as obtained in Reference Example 21 was reacted and treated in the same manner as in Example 15 to obtain the entitled compound as colorless crystals. m.p. 227–228° C. (recrystallized from ethyl acetate-isopropyl ether) NMR (200 MHz, CDCl$_3$) ppm: Same as the spectrum of the compound of Example 16 [α]$_D$: −107.1° (c=0.521, MeOH). Elemental Analysis for C$_{30}$H$_{25}$N$_3$O$_2$F$_6$: Calcd.(%): C, 62.83; H, 4.39; N, 7.33. Found (%): C, 62.55; H, 4.40; N, 7.13.

Example 21

4-[3,5-Bis(trifluoromethyl)benzyl]-2,3,4,5-tetrahydro-5-oxo-6-phenyl-1H-pyrido[2,3-e][1,4]diazepine A mixture of the compound (370 mg) as obtained in Reference Example 22, anhydrous potassium carbonate (200 mg) and xylene (10 ml) was stirred for 9 hours with heating under reflux. After the reaction mixture was cooled, water was added thereto. Then, the mixture was extracted with ethyl acetate. The extract was washed with water and dried, and the solvent was removed by distillation. Thus, the entitled compound was obtained as colorless crystals. m.p. 242–243° C. (recrystallized from ethyl acetate-isopropyl ether) NMR(200 MHz, CDCl$_3$) ppm: 3.60–3.80(4H,m), 4.81(2H,s), 4.86(1H,s), 6.87(1H,d,J=5.2 Hz), 7.30–7.50(6H, m), 7.79(2H,s), 7.85(1H,s), 8.21(1H,d,J=5.2 Hz) Elemental Analysis for C$_{23}$H$_{17}$N$_3$OF$_6$: Calcd.(%): C, 59.36; H, 3.68; N, 9.03. Found (%): C, 59.24; H, 3.66; N, 9.06. EI-MS m/z: 465 (M$^+$) [(C$_{23}$H$_{17}$N$_3$OF$_6$)$^+$]

Example 22
5-[3,5-Bis(trifluoromethyl)benzyl]-2,3,4,5-tetrahydro-6-oxo-7-phenyl-6H-pyrido[2,3-b][1,5]oxazocine The compound as obtained in Reference Example 23 was reacted and treated in the same manner as in Example 11 to obtain the entitled compound as colorless crystals. m.p. 188–189° C. (recrystallized from ethyl acetate-isopropyl ether) NMR(200 MHz, CDCl$_3$) ppm: 1.65–1.88(1H,m), 2.18–2.45(1H,m), 3.36(1H,dd,J=15.2 Hz), 3.73(1H,m), 4.17 (1H,d,J=15.2 Hz), 4.32(1H,dt,J=12.6,3.6 Hz), 4.67(1H,ddd, J=12.6,5.6,2.4 Hz), 5.50(1H,d,J=15.2 Hz), 7.16(1H,d,J=5.2 Hz), 7.20–7.45(5H,m), 7.71(2H,s), 7.83(1H,s), 8.41(1H,d, J=5.2 Hz) Elemental Analysis for $C_{24}H_{18}N_2O_2F_6$: Calcd. (%): C, 60.00; H, 3.78; N, 5.83. Found (%): C, 59.92; H, 3.76; N, 5.89.

Example 23
4-[3,5-Bis(trifluoromethyl)benzyl]-2,3,4,5-tetrahydro-7-methyl-5-oxo-6-phenylpyrido[3,2-f][1,4]oxazepine The compound as obtained in Reference Example 24 was reacted and treated in the same manner as in Example 11 to obtain the entitled compound as colorless crystals. m.p. 179–181° C. (recrystallized from ethyl acetate-isopropyl ether) NMR(200 MHz, CDCl$_3$) ppm: 2.13(3H,s), 3.57(2H, t,J=5.8 Hz), 4.42(2H,t,J=5.8 Hz), 4.80(2H,s), 7.16(2H,m), 7.47(3H,m), 7.65(2H,s), 7.81(1H,s), 8.32(1H,s)

Example 24
5-[3,5-Bis(trifluoromethyl)benzyl]-2,3,4,5-tetrahydro-8-methyl-6-oxo-7-phenyl-6H-pyrido[2,3-b][1,5]oxazocine The compound as obtained in Reference Example 25 was reacted and treated in the same manner as in Example 11 to obtain the entitled compound as colorless crystals. m.p. 180–182° C. (recrystallized from ethyl acetate-isopropyl ether) NMR(200 MHz, CDCl$_3$) ppm: 1.71(1H,m), 2.07(3H, m), 2.28(1H,m), 3.24(1H,dd,J=15.2,3.8 Hz), 3.64(1H,dd,J= 15.2,12.0 Hz), 4.05(1H,d,J=15.6 Hz), 4.27(1H,dt,J=12.6,3.8 Hz), 4.63(1H,ddd,J=12.6,5.4,2.0 Hz), 5.45(1H,d,J=15.6 Hz), 7.38(5H,m), 7.54(2H,s), 7.78(1H,s), 8.29(1H,s)

Example 25
(+/−)-7-[3,5-Bis(trifluoromethyl)benzyl]-6,7,8,9,10,12-hexahydro-9-hydroxy-5-(4-methylphenyl)-6,12-dioxo[1,4]diazepino [2,1-g][1,7]naphthyridine The compound as obtained in Reference Example 26 was reacted and treated in the same manner as in Example 2 to obtain the entitled compound as colorless crystals. m.p. 282–283° C. (recrystallized from acetone-ethyl ether) NMR (200 MHz, CDCl$_3$) ppm: 2.43(3H,s), 3.35–3.63(3H,m), 4.02 (1H×⅜,d,J=3.5 Hz,—OH), 4.21(1H×⅜,d,J=15 Hz), 4.30 (1H×⅝,d,J=3.5 Hz,—OH), 4.38(1H×⅝,d,J=15 Hz), 4.60 (1H,m), 5.24(1H×⅜,d,J=15 Hz), 5.61(1H×⅝,d,J=15 Hz), 5.68(1H,m), 6.92(1H,t-like,J=3.8 Hz), 7.19–7.86(8H,m), 8.95(1H,d,J=4 Hz) Elemental Analysis for $C_{28}H_{21}N_3O_3F_6\cdot¼H_2O$: Calcd.(%): C, 59.42; H, 3.83; N, 7.42. Found (%): C, 59.45; H, 3.74; N, 7.39. EI-MS m/z: 561 (M$^+$) (($C_{28}H_{21}N_3O_3F_6$)$^+$]

Example 26
7-Benzyl-6,7,8,9,10,12-hexahydro-6,12-dioxo-5-phenyl[1,4]diazepino[2,1-g][1,7]naphthyridine N-Benzyl-7,8-dihydro-7-(3-hydroxypropyl)-8-oxo-5-phenyl-6-pyrido[3,4-b]pyridinecarboxamide (this was obtained by reacting the compound as obtained in Reference Example 27 with 3-amino-1-propanol and treated in the same manner as in Reference Example 13) was reacted and treated in the same manner as in Example 12 to obtain the entitled compound as colorless crystals. m.p. 210–212° C. (recrystallized from ethyl acetate-ethyl ether) NMR(200 MHz, CDCl$_3$) ppm: 1.7–2.2(2H,m), 3.2–3.6(3H,m), 4.30 (1H,d,J=14 Hz), 4.89(1H,d,J=14 Hz), 5.43(1H,dd,J=14,5.7 Hz), 7.0–7.7(11H,m), 7.70(1H,dd,J=8,4,1.6 Hz), 8.92(1H, dd,J=4.4,1.6 Hz)

Example 27
7-Benzyl-6,7,8,9,10,11-hexahydro-6,13-dioxo-5-phenyl-13H-[1,4]diazocino[2,1-g][1,7]naphthyridine N-Benzyl-7,8-dihydro-7-(5-hydroxybutyl)-8-oxo-5-phenyl-6-pyrido[3,4-b]pyridinecarboxamide (this was obtained by reacting the compound as obtained in Reference Example 27 with 4-amino-1-butanol and treated in the same manner as in Reference Example 16) was reacted and treated in the same manner as in Example 15 to obtain the entitled compound as colorless crystals. m.p. 243–244° C. (recrystallized from acetone-ethyl ether) NMR(200 MHz, CDCl$_3$) ppm: 1.6–2.3(4H,m), 3.15(1H,m), 3.35–3.65(2H, m), 3.76(1H,d,J=15 Hz), 5.15(1H,dd,J=14,5,7 Hz), 5.42(1H, d,J=15 Hz), 6.64(2H,d,J=6.2 Hz), 7.0–7.3(4H,m), 7.3–7.7 (6H,m), 8.91(1H,dd,J=4.2,1.8 Hz)

Example 28
7-Benzyl-6,7,8,9,10,11,12,14-octahydro-6,14-dioxo-5-phenyl-[1,4]diazonino[2,1-g][1,7]naphthyridine N-Benzyl-7,8-dihydro-7-(5-hydroxypentyl)-8-oxo-5-phenyl-6-pyrido[3,4-b]pyridinecarboxamide (this was obtained by reacting the compound as obtained in Reference Example 27 with 5-amino-1-pentanol and treated in the same manner as in Reference Example 16) was reacted and treated in the same manner as in Example 15 to obtain the entitled compound as colorless crystals. m.p. 224–226° C. (recrystallized from ethyl acetate-ethyl ether) NMR(200 MHz, CDCl$_3$) ppm: 1.3–1.9(4H,m), 2.09(2H,m), 2.85–3.05 (1H,m), 3.15–3.40(1H,m), 3.50(1H,dt,J$_d$=15 Hz,J$_t$=6.4 Hz), 3.64(1H,d,J=15 Hz), 4.97(1H,dt,J$_d$=15 Hz,J$_t$=4.8 Hz), 5.48 (1H,d,J=15 Hz), 6.43(2H,d,J=7.2 Hz), 7.05–7.25(4H,m), 7.3–7.7(6H,m), 8.91(1H,dd,J=4.2,1.8 Hz)

Example 29
7-(3,4-Dichlorbenzyl)-6,7,8,9,10,12-hexahydro-6,12-dioxo-5-phenyl[1,4]diazepino[2,1-g][1,7]naphthyridine N-(3,4-Dichlorobenzyl)-7,8-dihydro-7-(3-hydroxypropyl)-8-oxo-5-phenyl-6-pyrido[3,4-b]pyridinecarboxamide (this was obtained by reacting the compound as obtained in Reference Example 28 with 3-amino-1-propanol and treated in the same manner as in Reference Example 13) was reacted and treated in the same manner as in Example 12 to obtain the entitled compound as colorless crystals. m.p. 224–226° C. (recrystallized from ethyl acetate-ethyl ether) NMR(200 MHz, CDCl$_3$) ppm: 1.9–2.–3(2H,m), 3.2–3.6(3H,m), 4.01(1H,d,J=15 Hz), 5.05 (1H,d,J=15 Hz), 5.49(1H,dd,J=13,5.0 Hz), 6.9–7.1(2H,m), 7.25(1H,m), 7.38(1H,d,J=8.6 Hz), 7.3–7.8(6H,m), 8.93(1H, d,J=4.0 Hz)

Example 30
7-(3,4-Dichlorbenzyl)-6,7,8,9,10,11-hexahydro-6,13-dioxo-5-phenyl-13H-[1,4]diazocino[2,1-g][1,7]naphthyridine N-(3,4-Dichlorobenzyl)-7,8-dihydro-7-(5-hydroxybutyl)-8-oxo-5-phenyl-6-pyrido[3,4-b]pyridinecarboxamide (this was obtained by reacting the compound as obtained in Reference Example 28 with 4-amino-1-butanol and treated in the same manner as in Reference Example 16) was reacted and treated in the same manner as in Example 15 to obtain the entitled compound as colorless crystals. m.p. 236–238° C. (recrystallized from acetone-ethyl ether) NMR (200 MHz, CDCl$_3$) ppm: 1.7–2.3(4H,m), 3.14(1H,m), 3.39–3.60(2H,m), 3.70(1H,d,J=15 Hz), 5.14(1H,dd,J=15,5.9 Hz), 5.35(1H,d,J=15 Hz), 6.35(1H,dd,J=8.4,2.0 Hz), 7.02 (2H,m), 7.18(1H,d,J=8.4 Hz), 7.3–7.6(6H,m), 8.91(1H,dd, J=4.0,1.8 Hz)

Example 31
(S)-5-(3,5-Bis(trifluoromethyl)benzyl]-2,3,4,5-tetrahydro-3,8-dimethyl-6-oxo-7-phenyl-6H-pyrido[2,3-b][1,5]oxazocine The compound as obtained in Reference Example 29 was reacted and treated in the same manner as in Example 11 to obtain the entitled compound as colorless crystals. m.p. 147–148° C. (recrystallized from ethyl acetate-hexane) NMR(200 MHz, CDCl$_3$) ppm: 0.83(3H,d,J=7.4 Hz), 2.07 (3H,s), 2.39(1H,m), 2.97(1H,d,J=15.4 Hz), 3.48(1H,m), 3.87(1H,dd,J=10.4,12.4 Hz), 4.06(1H,d,J=15.6 Hz), 4.59 (1H,dd,J=5.2,12.4 Hz), 5.44(1H,d,J=15.4 Hz), 7.37(2H,s), 7.53(2H,s), 7.78(1H,s), 8.29(1H,s) Elemental Analysis for C$_{26}$H$_{22}$N$_2$O$_2$F$_6$: Calcd.(%): C, 61.42, H, 4.36, N, 5.51. Found (%): C, 61.30, H, 4.52, N, 5.70. $[\alpha]_D^{20}$: −106.8° (C=0.257, CHCl$_3$)

Example 32
(R)-5-[3,5-Bis(trifluoromethyl)benzyl]-2,3,4,5-tetrahydro-3,8-dimethyl-6-oxo-7-phenyl-6H-pyrido[2,3-b][1,5]oxazocine The compound as obtained in Reference Example 30 was reacted and treated in the same manner as in Example 11 to obtain the entitled compound as colorless crystals. m.p. 147–149° C. (recrystallized from ethyl acetate-hexane) NMR(200 MHz, CDCl$_3$) ppm: Same as the spectrum of the compound of Example 31 Elemental Analysis for C$_{26}$H$_{22}$N$_2$O$_2$F$_6$: Calcd.(%): C, 61.42, H, 4.36, N, 5.51. Found (%): C, 61.26, H, 4.33, N, 5.69. $[\alpha]_D^{20}$: +102.5° (C=0.573, CHCl$_3$)

Example 33
4-[3,5-Bis(trifluoromethyl)benzyl]-2,3,4,5-tetrahydro-8-methyl-5-oxo-6-phenylpyrido[3,2-f][1,4]oxazepine The compound as obtained in Reference Example 31 was reacted and treated in the same manner as in Example 11 to obtain the entitled compound as colorless crystals. m.p. 151–153° C. (recrystallized from ethyl acetate-isopropyl ether) NMR(200 MHz, CDCl$_3$) ppm: 2.58(3H,s), 3.69(2H, t,J=5.4 Hz), 4.47(2H,d,J=5.4 Hz), 4.87(2H,s), 7.11(1H,s), 7.17–7.56(5H,m), 7.80(2H,s), 7.86(1H,s) Elemental Analysis for C$_{24}$H$_{18}$N$_2$O$_2$F$_6$.¼ H$_2$O: Calcd.(%): C, 59.44, H, 3.85, N, 5.78. Found (%): C, 59.42, H, 3.82, N, 5.84.

Example 34
5-[3,5-Bis(trifluoromethyl)benzyl]-2,3,4,5-tetrahydro-9-methyl-6-oxo-7-phenyl-6H-pyrido[2,3-b][1,5]oxazocine The compound as obtained in Reference Example 32 was reacted and treated in the same manner as in Example 11 to obtain the entitled compound as colorless crystals. m.p. 164–165° C. (recrystallized from ethyl acetate-isopropyl ether) NMR(200 MHz, CDCl$_3$) ppm: 1.79(1H,m), 2.30(1H, m), 2.56(3H,s), 3.35(1H,m), 3.77(1H,m), 4.14(1H,d,J=15.2 Hz), 4.31(1H,m), 4.65(1H,m), 5.49(1H,d,J=15.2 Hz), 7.02 (1H,s), 7.20–7.50(5H,m), 7.72(2H,s), 7.83(1H,s). Elemental Analysis for C$_{25}$H$_{20}$N$_2$O$_2$F$_6$: Calcd.(%): C, 60.73, H, 4.08, N, 5.68. Found (%): C, 60.43, H, 4.04, N, 5.74.

Example 35
4-[3,5-Bis(trifluoromethyl)benzyl]-2,3,4,5-tetrahydro-8-methyl-5-oxo-6-phenylpyrido[3,2-f][1,4]oxazepine 9-oxide m-Chloroperbenzoic acid (870 mg) was added to a chloroform (30 ml) solution of the compound (1.20 g) as obtained in Example 33 and stirred for 20 hours at room temperature. The solvent was removed by distillation, and aqueous potassium carbonate solution was added to the residue, which was then extracted with ethyl acetate. The extract was washed with aqueous potassium carbonate solution and dried, and the solvent was removed by distillation. Thus, the entitled compound was obtained as colorless crystals (1.10 g). m.p. 181–183° C. (recrystallized from TFH-isopropyl ether) NMR(200 MHz, CDCl$_3$) ppm: 2.62 (3H,s), 3.72(2H,m), 4.65(2H,m), 4.89(2H,s), 7.18(1H,s), 7.20–7.50(5H,m), 7.79(2H,s), 7.87(1H,s) Elemental Analysis for C$_{24}$H$_{18}$N$_2$O$_3$F$_6$.½ H$_2$O: Calcd.(%): C, 57.03, H, 3.79, N, 5.54. Found (%): C, 57.15, H, 3.77, N, 5.16.

Example 36
5-[3,5-Bis(trifluoromethyl)benzyl]-2,3,4,5-tetrahydro-9-methyl-6-oxo-7-phenyl-6H-pyrido[2,3-b][1,5]oxazocine 10-oxide The compound as obtained in Example 34 was reacted and treated in the same manner as in Example 35 to obtain the entitled compound as colorless crystals (727 mg). m.p. 116–118° C. (recrystallized from ethanol-ethyl ether) NMR (200 MHz, CDCl$_3$) ppm: 1.60–1.82(1H,m), 2.42(1H,m), 2.61(3H,s), 3.43(1H,dd,J=6.0,17.0 Hz), 3.81(1H,m), 4.18 (1H,d,J=15.4 Hz), 4.25(1H,m), 4.78(1H,dd,J=5.2,12.6 Hz), 5.52(1H,d,J=15.4 Hz), 7.16(1H,s), 7.18–7.50(5H,m), 7.72 (2H,s), 7.84(1H,s) Elemental Analysis for C$_{25}$H$_{20}$N$_2$O$_3$.½ H$_2$O: Calcd.(%): C, 58.31, H, 4.01, N, 5.44. Found (%): C, 58.17, H, 4.38, N, 5.31.

Example 37
8-Acetoxymethyl-4-[3,5-bis(trifluoromethyl)benzyl]-2,3,4,5-tetrahydro-5-oxo-6-phenylpyrido[3,2-f][1,4]oxazepine A mixture of the compound (939 mg) as obtained in Example 35 and acetic anhydride (25 ml) was heated under reflux for 20 minutes. The solvent was removed by distillation, and aqueous potassium carbonate solution was added to the residue, which was then extracted with ethyl acetate. The extract was washed with water and dried, and the solvent was removed by distillation. Thus, the entitled compound was obtained as colorless crystals (740 mg). m.p. 122–124° C. (recrystallized from ethyl acetate-isopropyl ether) NMR(200 MHz, CDCl$_3$) ppm: 2.18(3H,s), 3.71(2H, t,J=5.6 Hz), 4.50(2H,t,J=5.6 Hz), 4.88(2H,s), 5.21(2H,s), 7.18–7.50(6H,m), 7.79(2H,s), 7.87(1H,s) Elemental Analysis for C$_{26}$H$_{20}$N$_2$O$_4$F$_6$: Calcd.(%): C, 58.00, H, 3.74, N, 5.20. Found (%): C, 57.60, H, 4.02, N, 5.09.

Example 38
9-Acetoxymethyl-5-(3,5-bis(trifluoromethyl)benzyl]-2,3,4,5-tetrahydro-6-oxo-7-phenyl-6H-pyrido[2,3-b][1,5]oxazocine The compound as obtained in Example 36 was reacted and treated in the same manner as in Example 37 to obtain the entitled compound as colorless crystals (479 mg). m.p. 156–157° C. (recrystallized from ethyl acetate-isopropyl ether) NMR(200 MHz, CDCl$_3$) ppm: 1.60–1.95(1H,m), 2.00–2.20(1H,m), 2.17(3H,s), 336(1H,m), 3.75(1H,m), 4.14 (1H,d,J=15.2 Hz), 4.31(1H,m), 4.61(1H,m), 5.20(2H,s), 5.48(1H,d,J=15.2 Hz), 7.18(1H,s), 7.20–7.50(5H,m), 7.70 (2H,s), 7.83(1H,s) Elemental Analysis for C$_{27}$H$_{22}$N$_2$O$_4$F$_6$: Calcd.(%): C, 58.70, H, 4.01, N, 5.07. Found (%): C, 58.81, H, 4.11, N, 5.17.

Example 39
4-[3,5-Bis(trifluoromethyl)benzyl]-8-chloromethyl-2,3,4,5-tetrahydro-5-oxo-6-phenylpyrido[3,2-f][1,4]oxazepine Phosphorus oxychloride (1.24 ml) and triethylamine (1.85 ml) were dropwise added at the same time to a dichloromethane (100 ml) solution of the compound (4.40 g) as obtained in Example 35, while stirring at room temperature. The resulting mixture was heated under reflux for 1 hour, and then the solvent was removed by distillation. Aqueous potassium carbonate solution was added to the residue, which was then extracted with ethyl acetate-THF. The extract was washed with water and dried, and the solvent was removed by distillation. Thus, the entitled compound was obtained as colorless crystals (1.44 g). m.p. 183–184° C. (recrystallized from ethyl acetate-isopropyl ether) NMR(200 MHz, CDCl$_3$) ppm: 3.73(2H,t,J=5.4 Hz), 4.51(2H,t,J=5.4 Hz), 4.66(2H,s), 4.89(2H,s), 7.27(1H,s), 7.30–7.55(5H,m), 7.81(2H,s), 7.88(1H,s) Elemental Analysis for C$_{24}$H$_{17}$N$_2$O$_2$F$_6$Cl: Calcd.(%): C, 55.99, H, 3.33, N, 5.44. Found (%): C, 55.75, H, 3.53, N, 5.27.

Example 40

4-[3,5-Bis(trifluoromethyl)benzyl]-2,3,4,5-tetrahydro-8-methoxymethyl-5-oxo-6-phenylpyrido[3,2-f][1,4]oxazepine A mixture of the compound (151 mg) as obtained in Example 39, THF (2 ml), methanol (1 ml) and 28% sodium methoxide-methanol solution (1 ml) was stirred for 2 hours at room temperature. The solvent was removed by distillation, and water was added to the residue, which was then extracted with ethyl acetate. The extract was washed with water and dried, and the solvent was removed by distillation. Thus, the entitled compound was obtained as colorless crystals (118 mg). m.p. 139–140° C. (recrystallized from ethyl acetate-isopropyl ether) NMR(200 MHz, CDCl$_3$) ppm: 3.51(3H,s), 3.71(2H,t,J=5.6 Hz), 4.49(2H,t,J=5.6 Hz), 4.58(2H,s), 4.89(2H,s), 7.27(1H,s), 7.30–7.52(5H,m), 7.81 (2H,s), 7.87(1H,s) Elemental Analysis for C$_{25}$H$_{20}$N$_2$O$_3$F$_6$: Calcd.(%): C, 58.83, H, 3.95, N, 5.49. Found (%): C, 58.73, H, 3.95, N, 5.57.

Example 41

4-(3,5-Bis(trifluoromethyl)benzyl]-2,3,4,5-tetrahydro-8-(1-methyletoxymethyl)-5-oxo-6-phenylpyrido[3,2-f][1,4] oxazepine A mixture of the compound (150 mg) as obtained in Example 39, THF (1 ml), isopropanol (10 ml) and sodium hydride (60% oily) (120 mg) was stirred for 3 hours at room temperature. The solvent was removed by distillation, and water was added to the residue, which was then extracted with ethyl acetate. The extract was washed with water and dried, and the solvent was removed by distillation. The residue was purified by column chromatography (hexane:ethyl acetate=1:1) using silica gel to obtain the entitled compound as colorless crystals (74 mg). m.p. 134–136° C. (recrystallized from ethyl acetate-hexane) NMR(200 MHz, CDCl$_3$) ppm: 1.26(6H,d,J=6.0 Hz), 3.60–3.90(3H,m), 4.48(2H,t,J=5.4 Hz), 4.63(2H,s), 4.89 (2H,s), 7.27(1H,s), 7.30–7.55(5H,m), 7.81(2H,s), 7.87(1H, s) Elemental Analysis for C$_{27}$H$_{24}$N$_2$O$_3$F$_6$: Calcd.(%): C, 60.22, H, 4.49, N, 5.20. Found (%): C, 60.00, H, 4.61, N, 5.07.

Example 42

4-[3,5-Bis(trifluoromethyl)benzyl]-2,3,4,5-tetrahydro-8-methylthiomethyl-5-oxo-6-phenylpyrido[3,2-f][1,4] oxazepine A mixture of the compound (125 mg) as obtained in Example 39, methanol (5 ml) and aqueous 15% sodium methylmercaptan solution (1 ml) was stirred for 10 minutes at room temperature. The solvent was removed by distillation, and water was added to the residue, which was then extracted with ethyl acetate. The extract was washed with water and dried, and the solvent was removed by distillation. Thus, the entitled compound was obtained as colorless crystals (103 mg). m.p. 165–166° C. (recrystallized from ethyl acetate-isopropyl ether) NMR(200 MHz, CDCl$_3$) ppm: 2.14(3H,s), 3.72(2H,t,J=5.4 Hz), 3.79 (2H,s), 4.49(2H,t,J=5.4 Hz), 4.89(2H,s), 7.30–7.50(5H,m), 7.34(1H,s), 7.81(2H,s), 7.87(1H,s) Elemental Analysis for C$_{25}$H$_{20}$N$_2$O$_2$SF$_6$·⅙ H$_2$O: Calcd.(%): C, 56.71, H, 3.87, N, 5.29. Found (%): C, 56.67, H, 3.87, N, 5.23.

Example 43

8-Aminomethyl-4-[3,5-bis(trifluoromethyl)benzyl]-2,3,4,5-tetrahydro-5-oxo-6-phenylpyrido[3,2-f][1,4]oxazepine A mixture of the compound (500 mg) as obtained in Example 39, THF (10 ml) and aqueous 25% ammonia (10 ml) was heated in a sealed tube at 120° C. for 1 hour. After cooled, the solvent was removed by distillation, and water was added to the residue, which was then extracted with ethyl acetate. The extract was washed with water and dried, and the solvent was removed by distillation. Thus, the entitled compound was obtained as colorless crystals (443 mg). m.p. 188–191° C. (recrystallized from THF-ethyl ether) NMR(200 MHz, CDCl$_3$) ppm: 3.71(2H,t,J=5.6 Hz), 4.00(2H,s), 4.50(2H,t,J=5.6 Hz), 4.89(2H,s), 7.20–7.60(6H, m), 7.81(2H,s), 7.87(1H,s) Elemental Analysis for C$_{24}$H$_{19}$N$_3$O$_2$F$_6$: Calcd.(%): C, 58.19, H, 3.87, N, 8.48. Found (%): C, 58.36, H, 3.81, N, 8.00.

Example 44

4-[3,5-Bis(trifluoromethyl)benzyl]-2,3,4,5-tetrahydro-8-methylaminomethyl-5-oxo-6-phenylpyrido[3,2-f][1,4] oxazepine A mixture of the compound (150 mg) as obtained in Example 39 and 40% methylamine-methanol solution was stirred for 30 minutes at room temperature. The solvent was removed by distillation, and water was added to the residue, which was then extracted with ethyl acetate. The extract was washed with water and dried, and the solvent was removed by distillation. Thus, the entitled compound was obtained as colorless crystals (115 mg). m.p. 152–154° C. (recrystallized from ethyl acetate-isopropyl ether) NMR(200 MHz, CDCl$_3$) ppm: 2.50(3H,s), 3.70(2H,t,J=5.6 Hz), 3.89(2H,s), 4.48(2H, t,J=5.6 Hz), 4.88(2H,s), 7.22–7.50(6H,m), 7.80(2H,s), 7.86 (1H,s) Elemental Analysis for C$_{25}$H$_{21}$N$_3$O$_2$F$_6$: Calcd.(%): C, 58.94, H, 4.15, N, 8.25. Found (%): C, 58.71, H, 4.25, N, 8.35.

Example 45

4-[3,5-Bis(trifluoromethyl)benzyl]-8-dimethylaminomethyl-2,3,4,5-tetrahydro-5-oxo-6-phenylpyrido[3,2-f][1,4]oxazepine Dimethylamine (1 ml) was added to a THF (3 ml) solutin of the compound (150 mg) as obtained in Example 39, and then stirred for 30 minutes at room temperature. The solvent was removed by distillation, and water was added to the residue, which was then extracted with ethyl acetate. The extract was washed with water and dried, and the solvent was removed by distillation. Thus, the entitled compound was obtained as colorless crystals (128 mg). m.p. 186–188° C. (recrystallized from ethyl acetate-isopropyl ether) NMR (200 MHz, CDCl$_3$) ppm: 2.33(6H,s), 3.60(2H,s), 3.71(2H, t,J=5.6 Hz), 4.49(2H,t,J=5.6 Hz), 4.89(2H,s), 7.26(1H,s), 7.30–7.50(5H,m), 7.81(2H,s), 7.86(1H,s) Elemental Analysis for C$_{26}$H$_{23}$N$_3$O$_2$F$_6$: Calcd.(%): C, 59.66, H, 4.43, N, 8.03. Found (%): C, 59.43, H, 4.49, N, 7.84.

Example 46
4-[3,5-Bis(trifluoromethyl)benzyl]-8-cyclopropylaminomethyl-2,3,4,5-tetrahydro-5-oxo-6-phenylpyrido[3,2-f][1,4]oxazepine Cyclopropylamine (0.5 ml) was added to a THF (10 ml) solutin of the compound (155 mg) as obtained in Example 39, and then heated under reflux for 15 hours. The solvent was removed by distillation, and water was added to the residue, which was then extracted with ethyl acetate. The extract was washed with water and dried, and the solvent was removed by distillation. The residue was subjected to column chromatography (ethyl acetate:methanol=9:1) using silica gel, to thereby separate and purify the product. Thus, the entitled compound was obtained as colorless crystals (127 mg). m.p. 129–131° C. (recrystallized from ethyl acetate-hexane) NMR(200 MHz, CDCl$_3$) ppm: 0.44(4H,m), 2.19(1H,m), 3.69(2H,t,J=5.6 Hz), 3.97(2H,s), 4.48(2H,t,J=5.6 Hz), 4.87(2H,s), 7.25(1H,s), 7.26–7.55(5H,m), 7.79(2H, s), 7.86(1H,s) Elemental Analysis for C$_{27}$H$_{23}$N$_3$O$_2$F$_6$.⅙ H$_2$O: Calcd.(%): C, 60.22, H, 4.37, N, 7.80. Found (%): C, 59.98, H, 4.40, N, 7.85.

Example 47
4-[3,5-Bis(trifluoromethyl)benzyl]-2,3,4,5-tetrahydro-8-(N-methylpiperazinomethyl)-5-oxo-6-phenylpyrido[3,2-f][1,4]oxazepine N-Methylpiperazine (1 ml) was added to a THF (1 ml) solutin of the compound (150 mg) as obtained in Example 39, and then stirred for 15 hours at room temperature. The solvent was removed by distillation, and water was added to the residue, which was then extracted with ethyl acetate. The extract was washed with water and dried, and the solvent was removed by distillation. Thus, the entitled compound was obtained as colorless crystals (105 mg). m.p. 181–182° C. (recrystallized from ethyl acetate-isopropyl ether) NMR (200 MHz, CDCl$_3$) ppm: 2.30(3H,s), 2.48(4H,br), 2.59(4H, br), 3.68(2H,s), 3.71(2H,t,J=5.6 Hz), 4.48(2H,t,J=5.6 Hz), 4.89(2H,s), 7.27(1H,s), 7.30–7.50(5H,m), 7.81(2H,m), 7.87 (1H,s) Elemental Analysis for C$_{26}$H$_{28}$N$_4$O$_2$F$_6$: Calcd.(%): C, 60.20, H, 4.88, N, 9.68. Found (%): C, 59.96, H, 5.00, N, 9.51.

Example 48
8-Acetylaminomethyl-4-[3,5-bis(trifluoromethyl)benzyl]-2,3,4,5-tetrahydro-5-oxo-6-phenylpyrido[3,2-f][1,4]oxazepine Acetic anhydride (1 ml) was added to a pyridine (3 ml) solutin of the compound (150 mg) as obtained in Reference Example 43, and then stirred for 20 minutes at room temperature. The solvent was removed by distillation, and ethyl acetate was added to the residue. The resulting mixture was washed with 1 N-hydrochloric acid and water and dried, and then the solvent was removed by distillation. Thus, the entitled compound was obtained as colorless crystals (113 mg). m.p. 223–224° C. (recrystallized from THF-ethyl ether) NMR(200 MHz, CDCl$_3$) ppm: 2.07(3H,s), 3.72(2H, t,J=5.4 Hz), 4.49(2H,t,J=5.4 Hz), 4.56(2H,d,J=5.4 Hz), 4.88 (2H,s), 6.62(1H,br), 7.21(1H,s), 7.22–7.55(5H,m), 7.80(2H, s), 7.87(1H,s) Elemental Analysis for C$_{26}$H$_{21}$N$_3$O$_3$F$_6$: Calcd.(%): C, 58.10, H, 3.94, N, 7.82. Found (%): C, 58.06, H, 3.97, N, 7.99.

Example 49
4-[3,5-Bis(trifluoromethyl)benzyl]-2,3,4,5-tetrahydro-8-methanesulfonylaminomethyl-5-oxo-6-phenylpyrido[3,2-f][1,4]oxazepine Triethylamine (0.085 ml) and methanesulfonyl chloride (0.050 ml) were added to a THF (5 ml) solutin of the compound (150 mg) as obtained in Reference Example 43, and then stirred for 1 hour at room temperature. The solvent was removed by distillation, and ethyl acetate was added to the residue. The resulting mixture was washed with aqueous potassium carbonate solution and water and dried, and then the solvent was removed by distillation. Thus, the entitled compound was obtained as colorless crystals (108 mg). m.p. 194–195° C. (recrystallized from THF-isopropyl ether) NMR(200 MHz, CDCl$_3$) ppm: 2.99(3H,s), 3.72(2H,t,J=5.4 Hz), 4.44(2H,d,J=6.0 Hz), 4.48(2H,t,J=5.4 Hz), 4.88(2H,s), 5.55(1H,t,J=6.0 Hz), 7.26(1H,s), 7.27–7.50(5H,m), 7.80 (2H,s), 7.87(1H,s) Elemental Analysis for C$_{25}$H$_{21}$N$_3$O$_4$SF$_6$.½ H$_2$O: Calcd.(%): C, 51.55, H, 3.80, N, 7.21. Found (%): C, 51.43, H, 3.78, N, 7.07.

Example 50
6-[3,5-Bis(trifluoromethyl)benzyl]-5,6,7,8,9,10-hexahydro-3,9-dimethyl-5,10-dioxo-4-phenylpyrido[2,3-f][1,4]diazocine Triethylamine (0.42 ml) and methanesulfonyl chloride (0.24 ml) were added to a THF (15 ml) solutin of the compound (370 mg) as obtained in Reference Example 33, and then stirred for 1 hour at room temperature. Aqueous saturated sodium hydrogencarbonate solution (15 ml) was added to the reaction mixture and further stirred for 40 minutes at room temperature. Then, the mixture was extracted with ethyl acetate. The extract was washed with diluted hydrochloric acid and saturated saline solution and dried, and then the solvent was removed by distillation. The residue was dissolved in THF (30 ml), and sodium hydride (60% oily) (84 mg) was added thereto and heated under reflux for 40 minutes. The resulting reaction mixture was diluted with ethyl acetate, then washed with diluted hydrochloric acid, aqueous sodium carbonate solution and saturated saline solution, and thereafter the solvent was removed by distillation. Thus, the entitled compound was obtained as colorless crystals (213 mg). m.p. 203–205° C. (recrystallized from ethyl acetate-isopropyl ether) NMR(200 MHz, CDCl$_3$) ppm: 1.72(1H,dd,J=15,7.2 Hz), 2.18(3H,s), 2.75(1H,m), 3.04(3H,s), 3.54(3H,m), 4.09(1H,dd,J=14,7.2 Hz), 7.2–7.6(5H,m), 7.48(2H,s), 7.74(1H,s), 8.69(1H,s) Elemental Analysis for C$_{26}$H$_{21}$N$_3$O$_2$F$_6$.0.2 H$_2$O: Calcd.(%): C, 59.48, H, 4.11, N, 8.00. Found (%): C, 59.39, H, 4.13, N, 7.83. EI-MS m/z: 521 (M+) [(C$_{26}$H$_{21}$N$_3$O$_2$F$_6$)$^+$]

Example 51
6-[3,5-Bis(trifluoromethyl)benzyl]-5,6,7,8,9,10-hexahydro-9-methyl-5,10-dioxo-4-phenylpyrido[2,3-f][1,4]diazocine The compound as obtained in Reference Example 34 was reacted and treated in the same manner as in Example 50 to obtain the entitled compound as colorless crystals. m.p. 167–169° C. (recrystallized from ethyl acetate-isopropyl ether) NMR(200 MHz, CDCl$_3$) ppm: 2.05(1H,m), 2.87(1H, m), 3.10(3H,s), 3.36(1H,d,J=14 Hz), 3.48(1H,d,J=14 Hz), 3.97(1H,m), 4.26(1H,dd,J=15,7.1 Hz), 7.35(3H,m), 7.53 (5H,m), 7.71(1H,s), 8.81(1H,d,J=5.0 Hz) Elemental Analysis for C$_{25}$H$_{19}$N$_3$O$_2$F$_6$: Calcd.(%): C, 59.18, H, 3.77, N, 8.28. Found (%): C, 58.90, H, 3.81, N, 8.05.

Example 52
6-Benzyl-5,6,7,8,9,10-hexahydro-3,9-dimethyl-5,10-dioxo-4-phenylpyrido[2,3-f][1,4]diazocine N-Benzyl-N-(2-hydroxyethyl)-5-methyl-2-methylaminocarbonyl-4-phenyl-3-pyridinecarboxamide (this was prepared by reacting the compound as obtained in Reference Example 35 with methylamine and treated in the same manner as in Step 4 in Reference Example 33) was reacted and treated in the same manner as in Example 50 to obtain the entitled compound as colorless crystals. m.p. 183–184° C. (recrystallized from ethyl acetate-isopropyl ether) NMR(200 MHz, CDCl₃) ppm: 1.46(1H,dd,J=15,8.1 Hz), 2.17(3H,s), 2.69(1H,m), 3.02(3H,s), 3.27(1H,d,J=13 Hz), 3.44(1H,d,J=13 Hz), 3.56(1H,m), 4.00(1H,m), 7.01 (2H,m), 7.2–7.6(8H,m), 8.68(1H,s) Elemental Analysis for $C_{24}H_{23}N_3O_2$: Calcd.(%): C, 74.78, H, 6.01, N, 10.09. Found (%): C, 74.52, H, 6.13, N, 10.82.

Example 53
6-[3,5-Bis(trifluoromethyl)benzyl]-9-ethyl-5,6,7,8,9,10-hexahydro-3-methyl-5,10-dioxo-4-phenylpyrido[2,3-f][1,4]diazocine N-[3,5-Bis(trifluoromethyl)benzyl]-2-ethylaminocarbonyl-N-(2-hydroxyethyl)-5-methyl-4-phenyl-3-pyridinecarboxamide (this was prepared by reacting the compound as obtained in Step 3 in Reference Example 33 with ethylamine and treated in the same manner as in Step 4 in Reference Example 33) was reacted and treated in the same manner as in Example 50 to obtain the entitled compound as colorless crystals. m.p. 228–229° C. (recrystallized from ethyl acetate-isopropyl ether) NMR(200 MHz, CDCl₃) ppm: 1.33(3H,t,J=7.0 Hz), 1.51(1H,dd,J=15, 7.6 Hz), 2.18(3H,s), 2.72(1H,m), 3.39(1H,m), 3.42(1H,d,J=14 Hz), 3.57(1H,d,J=14 Hz), 3.57(1H,m), 3.77(1H,m), 4.03 (1H,dd,J=15,7.6 Hz), 7.2– 7.6(5H,m), 7.48(2H,s), 7.74(1H,s), 8.69(1H,s) Elemental Analysis for $C_{27}H_{23}N_3O_2F_6$: Calcd.(%): C, 60.56, H, 4.33, N, 7.85. Found (%): C, 60.28, H, 4.51, N, 7.65.

Example 54
6-[3,5-Bis(trifluoromethyl)benzyl]-6,7,8,9,10,11-hexahydro-3,10-dimethyl-5,11-dioxo-4-phenyl-5H-pyrido[2,3-g][1,5]diazonine The compound as obtained in Reference Example 36 was reacted and treated in the same manner as in Example 50, to obtain the entitled compound as colorless crystals. m.p. 247–249° C. (recrystallized from THF-ethyl acetate-isopropyl ether) NMR(200 MHz, CDCl₃) ppm: 1.2–1.4(1H, m), 1.8–2.3(1H,m), 2.15(3H,s), 3.0–3.6(4H,m), 3.04(3H,s), 3.91(1H,d,J=15 Hz), 5.32(1H,d,J=15 Hz), 7.0–7.5(7H,m), 7.75(1H,s), 8.59(1H,s) Elemental Analysis for $C_{27}H_{23}N_3O_2F_6$: Calcd.(%): C, 60.56, H, 4.33, N, 7.85. Found (%): C, 60.41, H, 4.46, N, 7.87. EI-MS m/z: 535 (M⁺) [$(C_{27}H_{23}N_3O_2F_6)^+$]

Example 55
4-[3,5-Bis(trifluoromethyl)benzyl]-8-hydroxymethyl-2,3,4,5-tetrahydro-5-oxo-6-phenylpyrido[3,2-f][1,4]oxazepine A mixture of 8-acetoxymethyl-4-[3,5-bis(trifluoromethyl)benzyl]-2,3,4,5-tetrahydro-5-oxo-6-phenylpyrido[3,2-f][1,4]oxazepine (Example 37) (4.51 g), ethanol (50 ml), and 4N-NaOH (50 ml) was stirred for 1.5 hours at room temperature. After evaporation of the solvent, water was added to the residue. The pH of the mixture was adjusted to ca.8 using dilute hydrochloric acid, and extracted with ethyl acetate. The extract was washed with water, dried and evaporated to give the entitled compound as colorless crystals (4.10 g). m.p. 199–201° C. (recrystallized from ethyl acetate-isopropyl ether) NMR(200 MHz, CDCl₃) ppm: 3.10 (1H,b), 3.71(2H,t,J=5.6 Hz), 4.50(2H,t,J=5.6 Hz), 4.78(2H,s), 4.88(2H,s), 7.20–7.50(6H,m), 7.80(2H,m), 7.87 (1H,s).

Example 56
4-[3,5-Bis(trifluoromethyl)benzyl]-2,3,4,5-tetrahydro-5-oxo-6-phenylpyrido[3,2-f][1,4]oxazepine-8-carboxylic acid A mixture of 4-[3,5-bis(trifluoromethyl)benzyl]-8-hydroxymethyl-2,3,4,5-tetrahydro-5-oxo-6-phenylpyrido[3,2-f][1,4]oxazepine (Example 55) (3.49 g), 2N-NaOH (100 ml) and pottasium permanganate (2.22 g) was stirred for 45 hours at room temperature. To the reaction mixture was added saturated aqueous sodium thiosulfate (10 ml). After the pH of the mixture was adjusted to ca.3 using hydrochloric acid. The mixture was extracted with ethyl acetate-THF (1:2). The extract was washed with aqueous sodium chloride solution, dried and evaporated to give the entitled compound as colorless crystals (2.74 g). m.p. 119–123° C. (recrystallized from methanol-ethyl ether) NMR(200 MHz, DMSO-d₆) ppm: 3.94(2H,b), 4.46(2H,b), 4.91(2H,s), 7.25–7.55(5H,m), 7.90(1H,s), 8.06(2H,s), 8.12(1H,s).

Example 57
4-[3,5-Bis(trifluoromethyl)benzyl]-2,3,4,5-tetrahydro-5-oxo-6-phenylpyrido[3,2-f][1,4]oxazepine-8-carboxamide A mixture of 4-[3,5-bis(trifluoromethyl)benzyl]-2,3,4,5-tetrahydro-5-oxo-6-phenylpyrido[3,2-f][1,4]oxazepine-8-carboxylic acid (Example 56) (220 mg), THF (15 ml), DMF (catalytic amount) and thionyl chloride (0.087 ml) was stirred for 2.5 hours with heating under reflux. The solvent was evaporated, and the residue was dissolved in THF (10 ml). To the solution was added aqueous ammonia (2 ml). After being stirred for 1 hour at room temperature, the mixture was concentrated. To the concentrate was added water, and the mixture was extracted with ethyl acetate. The extract was washed with water, dried and evaporated to give the entitled compound as colorless crystals (163 mg). m.p. 221–222° C. (recrystallized from ethyl acetate-isopropyl ether) NMR(200 MHz, CDCl₃) ppm: 3.74(2H,t,J=5.6 Hz), 4.50(2H,t,J=5.6 Hz), 4.92(2H,s), 5.80(1H,b), 7.30–7.55(6H, m), 7.83(2H,s), 7.89(1H,s), 8.20(1H,s).

The compounds of Examples 58 to 63 were similarly prepared by reaction and work-up as described in Example 57 using 4-[3,5-bis(trifluoromethyl)benzyl]-2,3,4,5-tetrahydro-5-oxo-6-phenylpyrido[3,2-f][1,4]oxazepine-8-carboxylic acid (Example 56) (via the acid chloride) and substituted amines (methylamine, dimethylamine, n-butylamine, piperidine, morpholine, and 1-methylpiperazine). The physico-chemical data are described below.

Example 58
4-[3,5-Bis(trifluoromethyl)benzyl]-N-methyl-2,3,4,5-tetrahydro-5-oxo-6-phenylpyrido[3,2-f][1,4]oxazepine-8-carboxamide m.p. 145° C. (decomposed) (recrystallized from THF-ethyl ether) NMR(200 MHz, CDCl₃) ppm: 3.04(3H,d,J=5.2 Hz), 3.73(2H,t,J=5.4 Hz), 4.48(2H,t,J=5.4 Hz), 4.90(2H,s), 7.25–7.60(5H,m), 7.65–7.95(1H,b), 7.81(2H,s), 7.87(1H,s), 8.17(1H,s).

Example 59
4-[3,5-Bis(trifluoromethyl)benzyl]-N,N-dimethyl-2,3,4,5-tetrahydro-5-oxo-6-phenylpyrido[3,2-f][1,4]oxazepine-8-carboxamide m.p. 235–236° C. (recrystallized from ethyl acetate-isopropyl ether) NMR(200 MHz, CDCl₃) ppm: 3.11(3H,s), 3.15(3H,s), 3.72(2H,t,J=5.6 Hz), 4.47(2H,t,J=5.6 Hz), 4.90 (2H,s), 7.25–7.50(5H,m), 7.60(1H,s), 7.82(2H,s), 7.88(1H,s).

Example 60
4-[3,5-Bis(trifluoromethyl)benzyl]-N-n-butyl-2,3,4,5-tetrahydro-5-oxo-6-phenylpyrido[3,2-f)[1,4]oxazepine-8-carboxamide m.p. 194–196° C. (recrystallized from ethyl acetate-isopropyl ether) NMR(200 MHz, CDCl₃) ppm: 0.96(3H,t, J=7.2 Hz), 1.20–1.80(6H,m), 4.78(2H,m), 3.73(2H,t,J=5.6 Hz), 4.49(2H,t,J=5.6 Hz), 4.91(2H,s), 7.30–7.58(5H,m), 7.82(2H,s), 7.88(1H,s), 8.18(1H,s).

Example 61
4-[3,5-Bis(trifluoromethyl)benzyl]-2,3,4,5-tetrahydro-5-oxo-6-phenyl-8-piperidinocarbonylpyrido[3,2-f][1,4]oxazepine m.p. 218–220° C. (recrystallized from THF-isopropyl ether) NMR(200 MHz, CDCl₃) ppm: 1.60(2H,b), 1.69(4H,b), 3.44(2H,t,J=5.6 Hz), 3.72(4H,m), 4.46(2H,t,J=5.6 Hz), 4.89(2H,s), 7.20–7.60(6H,m), 7.81(2H,s), 7.87(1H,s).

Example 62
4-[3,5-Bis(trifluoromethyl)benzyl]-2,3,4,5-tetrahydro-8-morpholinocarbonyl-5-oxo-6-phenylpyrido[3,2-f][1,4]oxazepine m.p. 265–266° C. (recrystallized from ethyl acetate-isopropyl ether) NMR(200 MHz, CDCl₃) ppm: 3.55–3.90 (10H,m), 4.46(2H,t,J=5.6 Hz), 4.89(2H,s), 7.25–7.52(5H,m), 7.59(1H,s), 7.81(2H,s), 7.88(1H,s).

Example 63
4-[3,5-Bis(trifluoromethyl)benzyl]-2,3,4,5-tetrahydro-8-[1-(4-methylpiperazinyl)carbonyl]-5-oxo-6-phenyl-pyrido(3,2-f][1,4]oxazepine-8-carboxamide m.p. 196–198° C. (recrystallized from THF-isopropyl ether) NMR(200 MHz, CDCl₃) ppm: 2.35(3H,s), 2.45(2H,m), 2.54(2H,m), 3.61(2H,m), 3.72(2H,t,J=5.6 Hz), 3.84(2H,m), 4.46(2H,t,J=5.6 Hz), 4.89(2H,s), 7.25–7.50(5H,m), 7.54(1H,s), 7.81(2H,s), 7.88(1H,s).

The compounds as described in Example 64–72 were obtained as colorless crystals from the compounds of Reference Example 37–45, respectively, by substantially the same reaction and work-up as Example 11 (i.e., by cyclization in the presence of sodium hydride in THF). The physico-chemical data are described below.

Example 64
2,3,4,5-Tetrahydro-5-oxo-6-phenyl-4-(3,4,5-trimethoxybenzyl)pyrido[3,2-f][1,4]oxazepine m.p. 177–179° C. (recrystallized from acetone-ethyl ether) NMR(200 MHz, CDCl₃) ppm: 3.70(2H,t,J=5.6 Hz), 3.85(6H,s), 3.87(3H,s), 4.34(2H,t,J=5.6 Hz), 4.72(2H,s), 6.60(2H,s), 7.24(1H,d,J=5.2 Hz), 7.30–7.55(5H,m), 8.42(1H,d,J=5.2 Hz).

Example 65
4-(3,4-Dichlorobenzyl)-2,3,4,5-tetrahydro-5-oxo-6-phenylpyrido[3,2-f][1,4]oxazepine m.p. 189–192° C. (recrystallized from THF-ethyl ether) NMR(200 MHz, CDCl₃) ppm: 3.67(2H,t,J=5.4 Hz), 4.42(2H,t,J=5.4 Hz), 4.71(2H,s), 7.10–7.70(9H,m), 8.43(1H,d,J=5.2 Hz).

Example 66
4-(3,4-Dimethoxybenzyl)-2,3,4,5-tetrahydro-5-oxo-6-phenylpyrido[3,2-f][1,4]oxazepine m.p. 175–176° C. (recrystallized from THF-ethyl ether) NMR(200 MHz, CDCl₃) ppm: 3.67(2H,t,J=5.4 Hz), 3.85(3H,s), 3.91(3H,s), 4.29(2H,t,J=5.4 Hz), 4.72(2H,s), 6.80–7.00(3H,m), 7.22(1H,d,J=5.2 Hz), 7.30–7.50(5H,m), 8.40(1H,d,J=5.2 Hz).

Example 67
4-Benzyl-2,3,4,5-tetrahydro-5-oxo-6-phenylpyrido[3,2-f][1,4]oxazepine m.p. 209–211° C. (recrystallized from methanol-ethyl ether) NMR(200 MHz, CDCl₃) ppm: 3.64(2H,t,J=5.6 Hz), 4.33(2H,t,J=5.6 Hz), 4.77(2H,s), 7.22(1H,d,J=5.2 Hz), 7.30–7.55(5H,m), 8.39(1H,d,J=5.2 Hz).

Example 68
2,3,4,5-Tetrahydro-6-oxo-7-phenyl-5-(3,4,5-trimethoxybenzyl)-6H-pyrido[2,3-b][1,5]oxazocine m.p. 155–156° C. (recrystallized from ethyl acetate-ethyl ether) NMR(200 MHz, CDCl₃) ppm: 1.65–1.85(1H,m), 2.29(1H,m), 3.40–3.75(2H,m), 3.77(6H,s), 3.87(3H,s), 4.07(1H,d,J=14.2 Hz), 4.27(1H,m), 4.66(1H,m), 5.22(1H,d,J=14.2 Hz), 6.53(2H,s), 7.15(1H,d,J=5.2 Hz), 7.35(5H,m), 8.40(1H,d,J=5.2 Hz).

Example 69
(S)-5-Benzyl-2,3,4,5-tetrahydro-3-methyl-6-oxo-7-phenyl-6H-pyrido[2,3-b][1,5]oxazocine m.p. 139–141° C. (recrystallized from ethyl acetate-isopropyl ether) NMR(200 MHz, CDCl₃) ppm: 0.84(3H,d, J=7.0 Hz), 2.43(1H,m), 3.12(1H,d,J=14.8 Hz), 3.39(1H,dd, J=15.4&10.2 Hz), 3.72–4.00(2H,m), 4.60(1H,dd,J=12.4&5.2 Hz), 5.51(1H,d,J=14.8 Hz), 7.16(1H,d,J=5.0 Hz), 7.20–7.50(10H,m), 8.39(1H,d,J=5.0 Hz).

Example 70
(R)-5-Benzyl-2,3,4,5-tetrahydro-3-methyl-6-oxo-7-phenyl-6H-pyrido[2,3-b][1,5]oxazocine m.p. 139–140° C. (recrystallized from ethyl acetate-isopropyl ether) NMR(200 MHz, CDCl₃) ppm: the same as the spectrum of the compound of Example 69.

Example 71
(S)-5-[3,5-Bis(trifluoromethyl)benzyl]-2,3,4,5-tetrahydro-3-methyl-6-oxo-7-phenyl-6H-pyrido[2,3-b][1,5]oxazocine m.p. 142–143° C. (recrystallized from ethyl acetate-isopropyl ether) NMR(200 MHz, CDCl₃) ppm: 0.87(3H,d, J=7.0 Hz), 2.46(1H,m), 3.10(1H,d,J=15.4 Hz), 3.59(1H,dd, J=15.0&10.6 Hz), 3.92(1H,dd,J=12.6&10.4 Hz), 4.20(1H, d,J=15.4 Hz), 4.63(1H,dd,J=12.6&5.2 Hz), 5.50(1H,d,J=15.4 Hz), 7.18(1H,d,J=5.0 Hz), 7.20–7.50(5H,m), 7.72(2H, s), 7.84(1H,s), 8.43(1H,d,J=5.0 Hz).

Example 72
(R)-5-[3,5-Bis(trifluoromethyl)benzyl]-2,3,4,5-tetrahydro-3-methyl-6-oxo-7-phenyl-6H-pyrido[2,3-b][1,5]oxazocine m.p. 142–143° C. (recrystallized from ethyl acetate-isopropyl ether) NMR(200 MHz, CDCl₃) ppm: same as the spectrum of the compound of Example 71.

Example 73
7-Benzyl-6,7,8,9,10,11-hexahydro-5-(4-methylphenyl)-6,13-dioxo-13H-[1,4]diazocino[2,1-g][1,7]naphthyridine The compound as obtained in Reference Example 46 was reacted and treated in the same manner as Example 15. m.p. 239–241° C. (recrystallized from ethyl acetate-isopropyl ether) NMR(200 MHz, CDCl₃) ppm: 1.6–2.1(4H,m), 2.50 (3H,s), 3.14(1H,dd,J=15&3.8 Hz), 3.3–3.7(2H,m), 3.77(1H, d,J=15 Hz), 5.14(1H,dd,J=14&5.9 Hz), 5.42(1H,d,J=15 Hz), 6.67(2H,d,J=7.0 Hz), 6.92(1H,dd,J=7.6&1.8 Hz), 7.1–7.5 (6H,m), 7.46(1H,dd,J=8.4&4.4 Hz), 7.60(1H,dd,J=8.4&1.8 Hz), 8.90(1H,dd,J=4.4&1.8 Hz).

Example 74
(9R)-7-Benzyl-6,7,8,9,10,11-hexahydro-9-methyl-5-(4-methylphenyl)-6,13-dioxo-13H-[1,4]diazocino[2,1-g][1,7]naphthyridine The compound as obtained in Reference Example 47 was reacted and treated in the same manner as Example 15. m.p. 218–220° C. (recrystallized from ethyl acetate-isopropyl ether) NMR(200 MHz, CDCl₃) ppm: 0.85(3H,d,J=7.0 Hz), 1.50–1.75(1H,m), 1.90–2.35(2H,m), 2.50(3H,s), 2.89(1H,d, J=15 Hz), 3.26(1H,dd,J=14&10 Hz), 3.59(1H,dd,J=14&11 Hz), 3.75(1H,d,J=15 Hz), 5.10(1H,dd,J=14&6.1 Hz), 5.42 (1H,d,J=15 Hz), 6.69(2H,d,J=6.8 Hz), 6.91(1H,dd,J= 7.8&1.8 Hz), 7.1–7.5(6H,m), 7.46(1H,dd,J=8.4&4.2 Hz), 7.60(1H,dd,J=8.4&1.8 Hz), 8.90(1H,dd,J=4.2&1.8 Hz).

Example 75

(9S)-7-Benzyl-6,7,8,9,10,11-hexahydro-9-methyl-5-(4-methylphenyl)-6,13-dioxo-13H-[1,4]diazocino[2,1-g][1,7]naphthyridine The compound as obtained in Reference Example 48 was reacted and treated in the same manner as Example 15. m.p. 218–220° C. (recrystallized from ethyl acetate-isopropyl ether) NMR(200 MHz, CDCl₃) ppm: same as the spectrum of the compound of Example 74.

Example 76

(9R)-6,7,8,9,10,11-Hexahydro-9-methyl-5-(4-methylphenyl)-6,13-dioxo-7-(3,4,5-trimethoxybenzyl)-13H-[1,4]diazocino[2,1-g][1,7]naphthyridine The compound as obtained in Reference Example 49 was reacted and treated in the same manner as Example 15. A white powder. NMR(200 MHz, CDCl₃) ppm: 0.90(3H,d,J= 6.6 Hz), 1.5–1.8(1H,m), 1.9–2.5(2H,m), 2.41(3H,s), 3.11 (1H,d,J=15 Hz), 3.35(1H,dd,J=15&11 Hz), 3.56(1H,dd,J= 14&11 Hz), 3.7–3.9(1H,m), 3.75(6H,s), 3.87(3H,s), 5.07 (1H,dd,J=14&5.9 Hz), 5.19(1H,d,J=15 Hz), 6.30(2H,s), 6.77(1H,d,J=8.0 Hz), 6.97(1H,d,J=8.0 Hz), 7.29(1H,d,J=8.2 Hz), 7.37(1H,d,J=8.2 Hz), 7.45(1H,dd,J=8.4&4.0 Hz), 7.58 (1H,dd,J=8.4&1.4 Hz), 8.89(1H,dd,J=4.0&1.4 Hz).

Example 77

(9S)-6,7,8,9,10,11-Hexahydro-9-methyl-5-(4-methylphenyl)-6,13-dioxo-7-(3,4,5-trimethoxybenzyl)-13H-[1,4]diazocino[2,1-g][1,7]naphthyridine The compound as obtained in Reference Example 50 was reacted and treated in the same manner as Example 15. A white powder. NMR(200 MHz, CDCl₃) ppm: same as the spectrum of the compound of Example 76.

Example 78

(9R)-7-(3,5-Dimethoxybenzyl)-6,7,8,9,10,11-hexahydro-9-methyl-5-(4-methylphenyl)-6,13-dioxo-13H-[1,4]diazocino[2,1-g][1,7]naphthyridine The compound as obtained in Reference Example 51 was reacted and treated in the same manner as Example 15. m.p. 206–208° C. (recrystallized from ethanol-isopropyl ether) NMR(200 MHz, CDCl₃) ppm: 0.87(3H,d,J=7.0 Hz), 1.67 (1H,m), 1.9–2.4(2H,m), 2.42(3H,s), 3.05(1H,d,J=15 Hz), 3.24–3.40(1H,m), 3.45–3.85(2H,m), 3.74(6H,s), 5.08(1H, dd,J=14&5.8 Hz), 5.26(1H,d,J=14 Hz), 6.12(2H,d,J=2.0 Hz), 6.38(1H,t,J=2.0 Hz), 6.84(1H,d,J=7.0 Hz), 7.09(1H,d, J=7.0 Hz), 7.29(1H,d,J=9.2 Hz), 7.38(1H,d,J=9.2 Hz), 7.46 (1H,dd,J=8.2&4.2 Hz), 7.62(1H,dd,J=8.2&1.6 Hz), 8.89 (1H,dd,J=4.2&1.6 Hz).

The compounds as described in Reference Example 37–45 were obtained as pale yellow oily substances using 2-chloro-4-phenyl-3-pyridinecarboxylic acid and N-substituted-N-(substituted)benzylamines-{i.e., N-(2-hydroxyethyl)-N-(3,4,5-trimethoxybenzyl)amine, N-(3,4-dichlorobenzyl)-N-(2-hydroxyethyl)amine, N-(3,4-dimethoxybenzyl)-N-(2-hydroxyethyl)amine, N-benzyl-N-(2-hydroxyethyl)amine, N-(3-hydroxypropyl)-N-(3,4,5-trimethoxybenzyl)amine, N-benzyl-N-[(S)-3-hydroxy-2-methylpropyl)amine, N-benzyl-N-[(R)-3-hydroxy-2-methylpropyl]amine, N-[3,5-Bis(trifluoromethyl)benzyl]-N-[(S)-3-hydroxy-2-methylpropyl]amine, and N-[3,5-bis (trifluoromethyl)benzyl]-N-[(R)-3-hydroxy-2-methylpropyl]amine, respectively} by substantially the same reaction and work-up as Reference Example 12—Step 2. The physico-chemical data are described below.

The compounds as described in Example 79–82 were obtained as colorless crystals from the compounds of Reference Example 52–55, respectively, by substantially the same reaction and work-up as Example 11 (i.e., by cyclization in the presence of sodium hydride in THF). The physico-chemical data are described below.

Example 79

4-Benzyl-2,3,4,5-tetrahydro-5-oxo-6-(4-methylphenyl) pyrido[3,2-f][1,4]oxazepine m.p. 203–204° C. (recrystallized from methanol-ethyl ether) NMR(200 MHz, CDCl₃) ppm: 2.41(3H,s), 3.64(2H, t,J=5.4 Hz), 4.32(2H,t,J=5.4 Hz), 4.78(2H,s), 7.21 (1H,d,J= 5.2 Hz), 7.25(4H,s), 7.38(5H,s), 8.37(1H,d,J=5.2 Hz).

Example 80

4-[3,5-Bis(trifluoromethyl)benzyl]2,3,4,5-tetrahydro-5-oxo-6-(4-methylphenyl)pyrido[3,2-f][1,4]oxazepine m.p. 212–213° C. (recrystallized from acetone-isopropyl ether) NMR(200 MHz, CDCl₃) ppm: 2.40(3H,s), 3.70(2H, t,J=5.6 Hz), 4.47(2H,t,J=5.6 Hz), 4.89(2H,s), 7.24(total 5H,m), 7.81 (2H,s), 7.87(1H,s), 8.41(1H,d,J=5.2 Hz).

Example 81

(S)-5-Benzyl-2,3,4,5-tetrahydro-3-methyl-7-(4-methylphenyl)-6-oxo-6H-pyrido(2,3-b][1,5]oxazocine m.p. 148–149° C. (recrystallized from acetone-ethyl ether) NMR(200 MHz, CDCl₃) ppm: 0.83(3H,d,J=7.4 Hz), 2.30–2.60(1H,b), 2.42(3H,s), 3.11(1H,d,J=15.4 Hz), 3.40 (1H,dd,J=15.4,10.4 Hz), 3.75–4.00(2H,m), 4.59(1H,dd,J= 12.4,4.8 Hz), 5.50(1H,d,J=15.0 Hz), 7.15(1H,d,J=4.8 Hz), 7.20–7.40(total 9H,m), 8.37(11H,d,J=4.8 Hz).

Example 82

(S)-5-[3,5-Bis(trifluoromethyl)benzyl]2,3,4,5-tetrahydro-3-methyl-7-(4-methylphenyl)-6-oxo-6H-pyrido[2,3-b][1,5]oxazocine m.p. 159–160° C. (recrystallized from acetone-isopropyl ether) NMR(200 MHz, CDCl₃) ppm: 0.86(3H,d,J=7.0 Hz), 2.20–2.60(1H,b), 2.37(3H,s), 3.09(1H,d,J=15.4 Hz), 3.58 (1H,dd,J=15.4,10.4 Hz), 3.89(1H,t,J=11.6 Hz), 4.18(1H,d, J=15.4 Hz), 4.62(1H,dd,J=12.2,5.2 Hz), 5.53(1H,d,J=15.4 Hz), 7.17(total 5H,m), 7.72(2H,s), 7.84(1H,s), 8.40(1H,d,J= 5.2 Hz).

Reference Example 1

N-[3,5-Bis(trifluoromethyl)benzyl]-7,8-dihydro-7-(2-hydroxyethyl)-5-(4-methylphenyl)-8-oxo-6-pyrido[3,4-b] pyridinecarboxamide Step 1

Iodine (catalytic amount) was added to a THF (30 ml) suspension of magnesium (2.4 g) in a nitrogen atmosphere at room temperature with stirring, and then a THF (20 ml) solution of 4-bromotoluene (17.1 g) was dropwise added thereto and stirred for 1 hour. The resulting mixture was added to a THF (50 ml) solution of 2,3-pyridinedicarboxylic acid anhydride (12.7 g) at 0–5° C. with stirring, and this was stirred for additional 30 minutes as it was and then for 1 hour at room temperature. The solvent was removed from the reaction mixture by distillation, and water (30 ml) was added to the residue, which was then adjusted the pH to 1.0 with hydrochloric acid. The mixture was extracted with dichloromethane, washed with water and dried. Then, the solvent was removed by distillation. Dichloromethane (about 10 ml) was added to the residue, and then isopropyl ether (about 70 ml) was added thereto. This was stirred for 16 hours at room temperature, and 3-(4-methylbenzoyl)-2-pyridinecarboxylic acid was obtained as colorless crystals (5.0 g). m.p. 168–170° C. (recrystallized from dichloromethane-ethyl acetate) NMR(200 MHz, CDCl$_3$) ppm: 2.41(3H,s), 7.24(2H,d,J=8.4 Hz), 7.62(2H,d,J=8.4 Hz), 7.70(1H,dd,J=8.0,4.8 Hz), 7.85(1H,dd,J=8.0,1.5 Hz), 8.77(1H,dd,J=4.8,1.5 Hz).

Step 2

A mixture of the compound (6.0 g) as obtained in Step 1, DMF (catalytic amount), thionyl chloride (10 ml), THF (50 ml) and dichloroethane (50 ml) was refluxed for 3 hours. After the solvent was removed by distillation, the residue was dissolved in dichloromethane (100 ml). Iminodiacetonitrile (3.0 g) and triethylamine (10 ml) were added to the resulting solution and stirred for 16 hours at room temperature. Then, the reaction mixture was washed with water, diluted hydrochloric acid, aqueous sodium hydrogencarbonate and water in that order, and dried. After the solvent was removed by distillation, obtained was N,N-bis(cyanomethyl)-3-(4-methylbenzoyl)-2-pyridinecarboxamide as pale brown crystals (4.3 g). m.p. 166–168° C. (recrystallized from ethyl acetate-ethyl ether) NMR(200 MHz, CDCl$_3$) ppm: 2.44(3H,s), 4.55(2H,s), 4.69 (2H,s), 7.31(2H,d,J=8.1 Hz), 7.56(1H,dd,J=7.9,4.9 Hz), 7.69(2H,d,J=8.1 Hz), 7.94(1H,dd,J=7.9,1.6 Hz), 8.78(1H, dd,J=4.9,1.6 Hz) Elemental Analysis for C$_{18}$H$_{14}$N$_4$O$_2$: Calcd.(%): C, 67.92; H, 4.43; N, 17.60. Found (%): C, 67.76; H, 4.54; N, 17.62.

Step 3

A mixture of the compound (0.86 g) as obtained in Step 2, 1,8-diazabicyclo[5.4.0]-7-undecene (DBU) (1 ml) and toluene (40 ml) was heated under reflux for 1 hour. The reaction mixture was diluted with ethyl acetate, then washed with water, diluted hydrochloric acid, aqueous sodium hydrogencarbonate and water in that order, and dried. After the solvent was removed by distillation, obtained was 7-cyanomethyl-7,8-dihydro-5-(4-methylphenyl)-8-oxo-6-pyrido[3,4-b]pyridinecarbonitrile as pale brown crystals (765 mg). m.p. 229–231° C. (recrystallized from ethyl acetate) NMR(200 MHz, CDCl$_3$) ppm: 2.48(3H,s), 5.28(2H, s), 7.31(2H,d,J=8.2 Hz), 7.40(2H,d,J=8.2 Hz), 7.64(1H,dd, J=8.2,4.4 Hz), 7.80(1H,dd,J=8.2,1.4 Hz), 9.06(1H,dd,J=4.4, 1.4 Hz) Elemental Analysis for C$_{18}$H$_{12}$N$_4$O.0.2H$_2$O: Calcd. (%): C, 71.14; H, 4.11; N, 18.43. Found (%): C, 71.20; H, 4.26; N, 18.20.

Step 4

A mixture of the compound (2.35 g) as obtained in Step 3, hydrochloric acid (25 ml) and acetic acid (25 ml) was heated under reflux for 1.5 hours. After the solvent was removed by distillation, water was added to the residue, and the resulting mixture was extracted with ethyl acetate. The resulting extract was washed with a saturated saline solution and then dried. After solvent was removed by distillation, obtained was 7-carboxymethyl-7,8-dihydro-5-(4-methylphenyl)-8-oxo-6-pyrido[3,4-b]pyridinecarbonitrile as colorless crystals (1.62 g). m.p. 253–254° C. (recrystallized from ethyl acetate) NMR(200 MHz, CDCl$_3$) ppm: 2.46(3H, s), 5.22(2H,s), 6.64(1H,bs,—CO$_2$H), 7.32(2H,d,J=8.2 Hz), 7.37(2H,d,J=8.2 Hz), 7.62(1H,dd,J=8.4,4.4 Hz), 7.82(1H,d, J=8.4 Hz), 9.09(1H,d,J=4.4 Hz) Elemental Analysis for C$_{18}$H$_{13}$N$_3$O$_3$0.1H$_2$O: Calcd.(%): C, 67.33; H, 4.14; N, 13.09. Found (%): C, 67.28; H, 4.19; N, 13.00.

Step 5

Hydroxybenzotriazole (770 mg) and 1,3-dicyclohexylcarbodiimide (1.23 g) were added to a THF (50 ml) solution of the compound (1.54 g) as obtained in Step 4, and stirred for 3 hours at room temperature. Next, sodium borohydride (550 mg) was added to the reaction mixture and stirred for 20 minutes at room temperature. The resulting reaction mixture was diluted with ethyl acetate, then washed with water and dried, and the solvent was removed by distillation. Dichloromethane was added to the residue, the insoluble substances were removed by filtration, and the solvent was removed by distillation. Hydrochloric acid (50 ml) was added to the residue and heated under reflux for 16 hours. The solvent was removed by distillation, and water with ice was added to the residue. Then, this was made alkaline with aqueous potassium carbonate, and thereafter extracted with ethyl acetate. The extract was washed with water and dried, and the solvent was removed by distillation. Thus, obtained was 6,8,9,11-tetrahydro-5-(4-methylphenyl)-6,11-dioxo[1,4]oxazino[3,4-g][1,7]naphthyridine as colorless crystals (0.86 g). m.p. 247–249° C. (recrystallized from ethyl acetate) NMR(200 MHz, CDCl$_3$) ppm: 2.45(3H,s), 4.48–4.72(4H,m), 7.12(2H,d,J= 8.0 Hz), 7.32(2H,d,J=8.0 Hz), 7.55(1H,dd,J=8.4,4.4 Hz), 7.68(1H,dd,J=8.4,1.6 Hz), 9.01(1H,dd,J=4.4,1.6 Hz) Elemental Analysis for C$_{18}$H$_{14}$N$_2$O$_3$ 0.2H$_2$O: Calcd.(%): C, 69.76; H, 4.68; N, 9.04. Found (%): C, 69.64; H, 4.86; N, 8.95.

Step 6

A mixture of the compound (410 mg) as obtained in Step 5 and 3,5-bis(trifluoromethyl)benzylamine (1.2 g) was heated in an argon atmosphere at 150° C. for 2.5 hours. After this was cooled to room temperature, isopropyl ether was added thereto and the entitled compound was obtained as colorless crystals (441 mg). m.p. 123–125° C. (recrystallized from ethyl acetate) NMR(200 MHz, CDCl$_3$) ppm: 2.28(3H,s), 3.71(2H,m), 3.97(2H,m), 4.46(2H,d,J=5.2 Hz), 7.00–7.20(4H,m), 7.37(1H,dd,J=8.4,4.2 Hz), 7.52(1H, dd,J=8.4,1.6 Hz), 7.66(2H,s), 7.76(1H,s), 8.51(1H,bs), 8.61 (1H,dd,J=4.2,1.6 Hz) Elemental Analysis for C$_{27}$H$_{21}$N$_3$O$_3$F$_6$: Calcd.(%): C, 59.02; H, 3.85; N, 7.65. Found (%): C, 58.95; H, 3.95; N, 7.52.

Reference Example 2

N-[3,5-Bis(trifluoromethyl)benzyl]-7-(3-chloropropyl)-7,8-dihydro-5-(4-methylphenyl)-8-oxo-6-pyrido[3,4-b]pyridinecarboxamide Step 1

A mixture of 3-(4-methylbenzoyl)-2-pyridinecarboxylic acid (13.9 g), diethyl bromomalonate (15.4 g), triethylamine (9.1 ml) and THF (120 ml) was heated under reflux for 6 hours. The solvent was removed by distillation, and ethyl acetate was added to the residue, which was washed with water, diluted hydrochloric acid and a saturated saline solution in that order and then dried. After the solvent was removed by distillation, the oily residue (20.5 g) was dissolved in THF (120 ml). DBU (4.2 ml) was added to the solution at −78° C. The mixture was stirred at 0° C. for 15 minutes, and then the solvent was concentrated. The resulting concentrate was poured into 2 N-HCl and then adjusted the pH to about 10 with sodium hydrogencarbonate. Then, this was extracted with ethyl acetate. The extract was washed with water and dried, and then the solvent was removed by distillation. Thus, obtained was diethyl 5,6-dihydro-5-hydroxy-5-(4-methylphenyl)-8-oxo-8H-pyrano [3, 4-b]pyridine-6,6-dicarboxylate as colorless crystals (14.1 g). m.p. 148–149° C. (recrystallized from ethyl acetate-isopropyl ether) NMR(200 MHz, CDCl$_3$) ppm: 1.06(3H,t, J=7.1 Hz), 1.21(3H,t,J=7.1 Hz), 2.31(3H,s), 3.95–4.30(4H, m), 4.65(1H,s), 7.15(2H,d,J=8.3 Hz), 7.55(1H,dd,J=8.0,4.8 Hz), 7.65(2H,d,J=8.3 Hz), 8.47(1H,dd,J=8.0,1.4 Hz), 8.86

(1H,dd,J=4.8,1.4 Hz) Elemental Analysis for $C_{21}H_{21}NO_7$: Calcd.(%): C, 63.15; H, 5.30; N, 3.51. Found (%): C, 63.09; H, 5.16; N, 3.47.

The same compound was alternatively obtained by the method described below.

A mixture of 3-(4-methylbenzoyl)-2-pyridinecarboxylic acid (3.0 g), DMF (1 drop), thionyl chloride (4.5 ml) and THF (30 ml) was heated under reflux for 2 hours. The solvent was evaporated, and the crystalline residue was dissolved in THF (50 ml). To the solution was added diethyl hydroxymalonate (4.1 g), and then added portionwise sodium hydride (60% oily) (646 mg) with stirring and cooling at –10° C. After being stirred for 30 minutes at –10° C., the reaction mixture was added to a solution of ethyl acetate (100 ml)-water (100 ml). The organic layer was separated, and the aqueous layer was extracted with ethyl acetate. The organic layer and the extract were combined, washed with water and aqueous sodium chloride solution, dried and evaporated to give the above described compound as colorless crystals (4.0 g).

Step 2

A mixture of the compound (14.1 g) as obtained in Step 1, acetic acid (100 ml) and hydrochloric acid (100 ml) was heated under reflux for 3 hours. The solvent was removed by distillation, and water was added to the residue. Thus, obtained was 5-(4-methylphenyl)-8-oxo-8H-pyrano[3,4-b]pyridine-6-carboxylic acid as colorless crystals (8.45 g). m.p. 274–277° C. (browned at about 240° C.) (recrystallized from THF-isopropyl ether) NMR(200 MHz, $CDCl_3$-DMSO-$d_6$) ppm: 2.43(3H,s), 6.10(1H,bs,—$CO_2H$), 7.16(2H,d,J=8.0 Hz), 7.29(2H,d,J=8.0 Hz), 7.50–7.70(2H,m), 8.94(1H,m) Elemental Analysis for $C_{16}H_{11}NO_4.10.1H_2O$: Calcd.(%): C, 67.89; H, 3.99; N, 4.95. Found (%): C, 67.70; H, 4.06; N, 4.83.

Step 3

A THF (5 ml) solution of 5-(4-methylphenyl)-8-oxo-8H-pyrano[3,4-b]pyridine-6-carboxylic acid (150 mg) was dropwise added to a mixture of 3-bromopropylamine hydrobromide (1.5 g), triethylamine (2.0 ml) and methanol (5 ml), and stirred at room temperature for 2 hours. Then, the solvent was removed by distillation. Hydrochloric acid (10 ml) was added to the residue, stirred for 14 hours at room temperature and then concentrated. The resulting concentrate was adjusted the pH to 1 with 1 N-NaOH. The crystals thus precipitated were taken out by filtration and washed with water to obtain 7-(3-bromopropyl)-7,8-dihydro-5-(4-methylphenyl)-8-oxo-6-pyrido[3,4-b]pyridinecarboxylic acid as colorless crystals (131 mg). m.p. 194–196° C. (recrystallized from THF-isopropyl ether) NMR(200 MHz, $CDCl_3$-DMSO-$d_6$) ppm: 2.30–2.60(2H,m), 2.42(3H,s), 3.54 (2H,t,J=6.8 Hz), 4.29(2H,t,J=7.2 Hz), 5.42(1H,bs,—$CO_2H$), 7.20–7.40(4H,m), 7.50(1H,m), 7.64(1H,d,J=8.0 Hz), 8.88 (1H,m).

Step 4

A mixture of the compound (110 mg) as obtained in Step 3, DMF (catalytic amount), thionyl chloride (0.3 ml), 1,2-dichloroethane (3 ml) and THF (3 ml) was heated under reflux for 40 minutes, and then the solvent was removed by distillation. A mixture of THF (5 ml), 3,5-bis (trifluoromethyl)benzylamine (82 mg), triethylamine (0.12 ml) and THF (2 ml) was added to the residue and stirred for 2 hours at room temperature. Ethyl acetate was added to the reaction mixture, which was washed with water, diluted hydrochloric acid, aqueous sodium hydrogencarbonate and water in that order, and then dried. After the solvent was removed by distillation, the entitled compound was obtained as colorless crystals (79 mg). m.p. 22.7–229° C. (recrystallized from ethyl acetate-isopropyl ether) NMR(200 MHz, $CDCl_3$) ppm: 2.10–2.40(2H,m), 2.27(3H,s), 3.4–3.7 (4H,m), 4.49(2H,d,J=5.8 Hz), 7.07(2H,d,J=7.6 Hz), 7.24 (2H,d,J=7.6 Hz), 7.40(1H,dd,J=8.4,4.2 Hz), 7.54(1H,dd,J= 8.4,1.4 Hz), 7.67(2H,s), 7.78(1H,s), 8.06(1H,bt), 8.70(1H, dd,J=4.2,1.4 Hz) Elemental Analysis for $C_{28}H_{22}N_3O_2ClF_6.0.2H_2O$: Calcd.(%): C, 57.43; H, 3.86; N, 7.18. Found (%): C, 57.29; H, 3.98; N, 7.07.

Reference Example 3

N-[3,5-Bis(trifluoromethyl)benzyl]-5-(4-methylphenyl)-8-oxo-8H-pyrano(3,4-b]pyridine-6-carboxamide The compound as obtained in Step 2 in Reference Example 2 was reacted with 3,5-(bistrifluoromethyl) benzylamine and treated in the same manner as in Step 4 in Reference Example 2, to obtain the entitled compound as colorless crystals. m.p. 182–183° C. (recrystallized from ethyl acetate-ether) NMR(200 MHz, $CDCl_3$) ppm: 2.44(3H, s), 4.63(2H,d,J=6.4 Hz), 7.17(2H,d,J=8.1 Hz), 7.34(2H,d,J= 8.1 Hz), 7.50–7.65(3H,m), 7.73(2H,s), 7.80(1H,s), 8.96(1H, m) Elemental Analysis for $C_{25}H_{16}N_2O_3F_6$: Calcd.(%): C, 59.30; H, 3.18; N, 5.53. Found (%): C, 59.42; H, 3.30; N, 5.45.

Reference Example 4

N-(2-methoxybenzyl)-5-(4-methylphenyl)-8-oxo-8H-pyrano[3,4-b]pyridine-6-carboxamide The compound as obtained in Step 2 in Reference Example 2 was reacted with 2-methoxybenzylamine and treated in the same manner as in Step 4 in Reference Example 2, to obtain the entitled compound as colorless crystals. m.p. 189–190° C. (recrystallized from ethyl acetate) NMR(200 MHz, $CDCl_3$) ppm: 2.44(3H,s), 3.90(3H, s), 4.48(2H,d,J=5.8 Hz), 6.85–6.95(2H,m), 7.10–7.35(6H, m), 7.43(1H,bt), 7.50–7.63(2H,m), 8.93(1H,m).

Reference Example 5

N-[3,5-Bis(trifluoromethyl)benzyl]-7,8-dihydro-7-(4-hydroxybutyl)-5-(4-methylphenyl)-8-oxo-6-pyrido[3,4-b]pyridinecarboxamide 4-Amino-1-butanol (0.5 ml) was added to a THF (5 ml)-methanol (10 ml) solution of the compound (200 mg) as obtained in Reference Example 3, at 0° C., and stirred at room temperature for 1 hour. The solvent was removed from the reaction mixture by distillation, and hydrochloric acid (15 ml) was added to the residue and stirred for 14 hours at room temperature. The reaction mixture was poured into aqueous potassium carbonate with ice and then extracted with ethyl acetate. The extract was washed with water and dried, and the solvent was removed by distillation. Thus, the entitled compound was obtained as colorless crystals (144 mg). m.p. 187–188° C. (recrystallized from ethyl acetate-isopropyl ether) NMR(200 MHz, $CDCl_3$) ppm: 1.3–1.5(2H, m), 1.6–1.9(2H,m), 2.29(3H,s), 2.82(1H,bs), 3.55(2H,t,J= 5.7 Hz), 3.69(2H,m), 4.48(2H,d,J=5.8 Hz), 7.08(2H,d,J=8.1 Hz), 7.21(2H,d,J=8.1 Hz), 7.29(1H,dd,J=8.4,4.2 Hz), 7.52 (1H,dd,J=8.4,1.4 Hz), 7.68(2H,s), 7.78(1H,s), 8.39(1H,bt), 8.61(1H,dd,J=4.2,1.4 Hz).

Reference Example 6

7,8-Dihydro-7-(3-hydroxypropyl)-N-(2-methoxybenzyl)-5-(4-methylphenyl)-8-oxo-6-pyrido[3.4-b]pyridinecarboxamide The compound as obtained in Reference Example 4 was reacted with 3-amino-1-propanol and treated in the same manner as in Reference Example 5, to obtain the entitled compound. This compound was used in Example 4 without being purified.

Reference Example 7
7,8-Dihydro-7-(4-hydroxybutyl)-N-(2-methoxybenzyl)-5-(4-methylphenyl)-8-oxo-6-pyrido[3,4-b]pyridinecarboxamide The compound as obtained in Reference Example 4 was reacted with 3-amino-1-butanol and treated in the same manner as in Reference Example 5, to obtain the entitled compound as colorless crystals. m.p. 205–206° C. (recrystallized from methanol-ethyl ether) NMR(200 MHz, CDCl$_3$) ppm: 1.57(2H,m), 1.95(2H,m), 2.33(3H,s), 2.71 (1H,bs), 3.66(2H,t,J=6.0 Hz), 3.75(3H,s), 4.00–4.15(2H,m), 4.29(2H,d,J=6.2 Hz), 6.59(1H,bt), 6.71–6.92(3H,m), 7.04–7.30(5H,m), 7.41(1H,dd,J=8.4,4.4 Hz), 7.62(1H,dd,J=8.4,1.4 Hz), 8.82(1H,dd,J=4.4,1.4 Hz).

Reference Example 8
N-[3,5-Bis(trifluoromethyl)benzyl]-7,8-dihydro-7-(5-hydroxypentyl)-5-(4-methylphenyl)-8-oxo-6-pyrido[3,4-b]pyridinecarboxamide The compound as obtained in Reference Example 3 was reacted with 5-amino-1-pentanol and treated in the same manner as in Reference Example 5, to obtain the entitled compound as colorless crystals. m.p. 136–137° C. (recrystallized from ethyl acetate-ethyl ether) NMR(200 MHz, CDCl$_3$) ppm: 1.10–1.35(2H,m), 1.35–1.55(2H,m), 1.6–1.9(2H,m), 2.28(3H,s), 3.50–3.70(4H,m), 4.47(2H,d,J=5.8 Hz), 7.06(2H,d,J=8.0 Hz), 7.19(2H,d,J=8.0 Hz), 7.35 (1H,dd,J=8.3,4.4 Hz), 7.50(1H,d,J=8.3,1.4 Hz), 7.69(2H,s), 7.78(1H,s), 8.29(1H,bt), 8.64(1H,dd,J=4.4,1.4 Hz).

Reference Example 9
N-[3,5-Bis(trifluoromethyl)benzyl]-7,8-dihydro-7-(3-hydroxypropyl)-8-oxo-5-phenyl-6-pyrido[3,4-b]pyridinecarboxamide

Step 1
3-Benzoyl-2-pyridinecarboxylic acid was used in place of 3-(4-methylbenzoyl)-2-pyridinecarboxylic acid in Step 1 in Reference Example 2, reacted and treated in the same manner as in Step 1 in Reference Example 2, to obtain diethyl 5,6-dihydro-5-hydroxy-8-oxo-5-phenyl-8H-pyrano[3,4-b]pyridine-6,6-dicarboxylate as colorless crystals. m.p. 146–147° C. (recrystallized from ethyl acetate-isopropyl ether) NMR(200 MHz, CDCl$_3$) ppm: 1.07(3H,t,J=7.2 Hz), 1.18(3H,t,J=7.2 Hz), 4.00–4.25(4H,m), 4.70(1H,s), 7.30–7.40(3H,m), 7.56(1H,dd,J=8.0,4.8 Hz), 7.74–7.85(2H, m), 8.48(1H,dd,J=8.0,1.5 Hz), 8.87(1H,dd,J=4.8,1.5 Hz).

Step 2
The compound as obtained in Step 1 was reacted with acetic acid and hydrochloric acid and treated in the same manner as in Step 2 in Reference Example 2, to obtain 8-oxo-5-phenyl-8H-pyrano[3,4-b]pyridine-6-carboxylic acid as colorless crystals. m.p. 288–290° C. (recrystallized from THF-methanol-ether) NMR(200 MHz, DMSO-d$_6$) ppm: 7.28–7.60(6H,m), 7.81(1H,dd,J=8.2,4.4 Hz), 8.95(1H, dd,J=4.4,1.6 Hz).

Step 3
The compound as obtained in Step 2 was reacted with 3,5-bis(trifluoromethyl)benzylamine and treated in the same manner as in Reference Example 3, to obtain N-[3,5-bis(trifluoromethyl)benzyl]-8-oxo-5-phenyl-8H-pyrano [3,4-b]pyridine-6-carboxamide as colorless crystals. m.p. 182–183° C. (recrystallized from ethyl acetate-isopropyl ether) NMR(200 MHz, CDCl$_3$) ppm: 4.61(2H,t,J=6.2 Hz), 7.24–7.34(2H,m), 7.49–7.67(6H,m), 7.72(2H,s), 7.79(1H,s), 8.96(1H,dd,J=4.2,1.6 Hz).

Step 4
The compound as obtained in Step 3 was reacted with 3-amino-1-propanol and treated in the same manner as in Reference Example 5, to obtain the entitled compound as colorless crystals. m.p. 129–130° C. (recrystallized from ethyl acetate-ethyl ether) NMR(200 MHz, CDCl$_3$) ppm: 1.91(2H,m), 3.45(2H,t,J=5.4 Hz), 3.70(2H,m), 4.46(2H,d,J=6.0 Hz), 7.2–7.4(5H,m), 7.44(1H,dd,J=8.4,4.4 Hz), 7.59(1H, dd,J=8.4,1.6 Hz), 7.61(2H,s), 7.78(1H,s), 8.25(1H,bt), 8.70 (1H,dd,J=4.4,1.6 Hz).

Reference Example 10
N-[3,5-Bis(trifluoromethyl)benzyl]-7,8-dihydro-7-(4-hydroxybutyl)-8-oxo-5-phenyl-6-pyrido[3,4-b]pyridinecarboxamide The compound as obtained in Step 3 in Reference Example 9 was reacted with 4-amino-1-butanol and treated in the same manner as in Reference Example 5, to obtain the entitled compound as colorless crystals. m.p. 155–157° C. (recrystallized from ethyl acetate-isopropyl ether) NMR(200 MHz, CDCl$_3$) ppm: 1.45(2H,m), 1.83(2H,m), 3.58(2H,t,J=5.8 Hz), 3.73(2H,m), 4.44(2H,d,J=5.8 Hz), 7.2–7.4(6H,m), 7.54(1H,dd,J=8.1,1.1 Hz), 7.60(2H,s), 7.77(1H,s), 8.05(1H, bt), 8.66(1H,dd,J=4.1,1.1 Hz).

Reference Example 11
N-[3,5-Bis(trifluoromethyl)benzyl]-1,2-dihydro-2-(4-hydroxybutyl)-4-(4-methylphenyl)-1-oxo-3-pyrido[3,4-c]pyridinecarboxamide

Step 1
4-(4-Methylbenzoyl)-3-pyridinecarboxylic acid was used in place of 3-(4-methylbenzoyl)-2-pyridinecarboxylic acid in Step 1 in Reference Example 2, reacted and treated in the same manner as in Step 1 in Reference Example 2, to obtain diethyl 3,4-dihydro-4-hydroxy-4-(4-methylphenyl)-1-oxo-1H-pyrano[3,4-c]pyridine-3,3-dicarboxylate as an yellow oil. NMR(200 MHz, CDCl$_3$) ppm: 1.08(3H,t,J=7.1 Hz), 1.21(3H,t,J=7.2 Hz), 2.31(3H,s), 4.00–4.40(4H,m), 4.72 (1H,bs), 7.14(2H,d,J=8.4 Hz), 7.64(2H,d,J=8.4 Hz), 8.05 (1H,d,J=5.3 Hz), 8.85(1H,d,J=5.3 Hz), 9.12(1H,s).

Step 2
The compound as obtained in Step 1 was reacted with acetic acid and hydrochloric acid and treated in the same manner as in Step 2 in Reference Example 2, to obtain 4-(4-methylphenyl)-1-oxo-1H-pyrano[3,4-c]pyridine-3-carboxylic acid as colorless crystals. m.p. 254–256° C. (recrystallized from THF-isopropyl ether) NMR(200 MHz, CDCl$_3$+d$_6$-DMSO) ppm: 2.43(3H,s), 5.31(1H,bs,COOH), 7.04(1H,d,J=5.5 Hz), 7.16(2H,d,J=7.8 Hz),, 7.29(2H,d,J=7.8 Hz), 8.81(1H,d,J=5.5 Hz), 9.54(1H,s).

Step 3
The compound as obtained in Step 2 was reacted with 3,5-bis(trifluoromethyl)benzylamine and treated in the same manner as in Reference Example 3, to obtain N-[3,5-bis (trifluoromethyl)benzyl]-4-(4-methylphenyl)-1-oxo-1H-pyrano[3,4-c]pyridine-3-carboxamide as colorless crystals. m.p. 188–189° C. (recrystallized from ethyl acetate-isopropyl ether) NMR(200 MHz, CDCl$_3$) ppm: 2.44(3H,s), 4.61(2H,d,J=6.2 Hz), 7.05(1H,d,J=5.3 Hz), 7.15(2H,d,J=8.1 Hz), 7.32(2H,d,J=8.1 Hz), 7.43(1H,bt), 7.70(2H,s), 7.80(1H, s), 8.85(1H,d,J=5.3 Hz), 9.56(1H,s).

Step 4
The compound as obtained in Step 3 was reacted with 4-amino-1-butanol and treated in the same manner as in Reference Example 5, to obtain the entitled compound as colorless crystals. m.p. 128–131° C. (recrystallized from ethyl acetate-isopropyl ether) NMR(200 MHz, CDCl$_3$) ppm: 1.45–1.70(2H,m), 1.75–2.05(2H,m), 2.31(3H,s), 3.65(2H,t, J=5.9 Hz), 3.98(2H,m), 4.36(2H,d,J=6.0 Hz), 7.00(1H,d,J=5.7 Hz), 7.12(2H,d,J=8.1 Hz), 7.18(2H,d,J=8.1 Hz), 7.56 (2H,s), 7.80(1H,s), 8.47(1H,d,J=5.7 Hz), 9.41(1H,s).

Reference Example 12
N-[3,5-Bis(trifluoromethyl)benzyl]-2-chloro-N-(2-hydroxyethyl)-4-phenyl-3-pyridinecarboxamide Step 1

3,5-Bis(trifluoromethyl)benzyl bromide (1.1 ml) was added to a THF (30 ml) solution of 2-aminoethanol (3.6 ml) while cooling it with ice. The resulting mixture was stirred for 1 hour at room temperature, ethyl acetate (30 ml) was added thereto, and this was washed with water and a saturated, aqueous sodium chloride solution. The organic layer was dried and the solvent was removed by distillation. Thus, obtained was N-(3,5-bis(trifluoromethyl)benzyl]-N-(2-hydroxyethyl)amine as colorless crystals (1.38 g). m.p. 107–108° C. (recrystallized from ethanol-ethyl ether) NMR (200 MHz, CDCl$_3$) ppm: 2.83(2H,t,J=5.4 Hz), 3.72(2H,t,J=5.4 Hz), 3.96(2H,s), 7.78(1H,s), 7.82(2H,s).

Step 2

Thionyl chloride (0.7 ml) and DMF (catalytic amount) were added to a THF (10 ml) solution of 2-chloro-4-phenyl-3-pyridinecarboxylic acid (318 mg) and heated under reflux for 4 hours. The solvent was removed by distillation, and the residue was dissolved in THF (5 ml). The resulting solution was added to a mixture of N-[3,5-bis(trifluoromethyl)benzyl]-N-(2-hydroxyethyl)amine (391 mg) that had been obtained in Step 1, triethylamine (0.57 ml) and THF (10 ml), while cooling with ice, and then stirred for 2 hours at room temperature. The solvent was removed by distillation, and water was added to the residue, which was then extracted with ethyl acetate. The extract was washed with water and dried, and then the solvent was removed by distillation. The residue was separated and purified by column chromatography (hexane:ethyl acetate=1:1) using silica gel, and the entitled compound was obtained as an oil (551 mg) (ratio of cis-trans isomers with respect to the amide bond=about 2:1). NMR(200 MHz, CDCl$_3$) ppm: 2.82–3.92(4H,m), 4.16(1H×⅓,d,J=16.0 Hz), 4.41(1H×⅓,d,J=16.0 Hz), 4.73(1H×⅔,d,J=15.0 Hz), 4.87(1H×⅔,d,J=15.0 Hz), 7.20–8.85(9H,m), 8.43(1H,m).

Reference Example 13
(S)-N-[3,5-Bis(trifluoromethyl)benzyl]-7,8-dihydro-7-(3-hydroxy-2-methylpropyl)-5-(4-methylphenyl)-8-oxo-6-pyrido[3,4-b]pyridinecarboxamide (S)-3-Amino-2-methyl-1-propanol (307 mg) was added to a THF (10 ml)-methanol (7.5 ml) solution of the compound (1.0 g) as obtained in Reference Example 3, and stirred for 14 hours at room temperature. Diluted hydrochloric acid was added to the reaction mixture, which was then extracted with ethyl acetate. The extract was washed with a saturated saline solution and then dried, and the solvent was removed by distillation. Acetonitrile (3 ml), toluene (21 ml) and DBU (0.42 ml) were added to the residue and heated under reflux for 1 hour. After cooled, the reaction mixture was diluted with ethyl acetate and then washed with water, diluted hydrochloric acid and a saturated saline solution in that order. The organic layer was dried, and the solvent was removed by distillation. Thus, the entitled compound was obtained as colorless crystals. m.p. 123–125° C. (after once melted, this again solidified), 215–216° C. (re-melted) (recrystallized from ethyl acetate-isopropyl ether) [α]$_D$: +11.1° (C=0.350,CHCl$_3$) NMR(200 MHz, CDCl$_3$) ppm: 0.79(3H,d,J=7.0 Hz), 2.13(1H,m), 2.28(3H,s), 3.10–3.70(4H,m), 4.48(2H,d,J=6.2 Hz), 7.00–7.25(4H,m), 7.43(1H,dd,J=8.4,4.2 Hz), 7.59(1H,dd,J=8.4,1.6 Hz), 7.69(2H,s), 7.79(1H,s), 8.38(1H,bt), 8.70(1H,dd,J=4.2,1.6 Hz) Elemental Analysis for C$_{29}$H$_{25}$N$_3$O$_3$F$_6$.0.5H$_2$O: Calcd.(%): C, 59.39; H, 4.47; N, 7.16. Found (%): C, 59.64; H, 4.31; N, 7.01.

Reference Example 14
(R)-N-[3,5-Bis(trifluoromethyl)benzyl]-7,8-dihydro-7-(3-hydroxy-2-methylpropyl)-8-oxo-5-phenyl-6-pyrido[3,4-b]pyridinecarboxamide The compound as obtained in Step 3 in Reference Example 9 was reacted with (R)-3-amino-2-methyl-1-propanol and treated in the same manner as in Reference Example 13, to obtain the entitled compound as colorless crystals. m.p. 101–103° C. (recrystallized from ethyl ether-isopropyl ether) NMR(200 MHz, CDCl$_3$) ppm: 0.77(3H,d, J=6.6 Hz), 2.14(1H,m), 3.10–3.70(4H,m), 4.47(2H,d,J=5.8 Hz), 7.1–7.4(5H,m), 7.45(1H,dd,J=8.4,4.2 Hz), 7.60(1H,d, J=8.4 Hz), 7.65(2H,s), 7.78(1H,s), 8.60(1H,bt), 8.69(1H,d, J=4.2 Hz) [α]$_D$: −5.4° (C=0.512,CHCl$_3$).

Reference Example 15
(R)-N-(3,5-Bis(trifluoromethyl)benzyl]-7,8-dihydro-7-(3-hydroxy-2-methylpropyl)-5-(4-methylphenyl)-8-oxo-6-pyrido[3,4-b]pyridinecarboxamide The compound as obtained in Reference Example 3 was reacted with (R)-3-amino-2-methyl-1-propanol and treated in the same manner as in Reference Example 13, to obtain the entitled compound as colorless crystals. m.p. 123–125° C. (after once melted, this again solidified), 215–216° C. (re-melted) (recrystallized from ethyl acetate-isopropyl ether) NMR(200 MHz, CDCl$_3$) ppm: same as the spectrum of the compound of Reference Example 13. [α]$_D$: −9.0° (C=0.346,CHCl$_3$).

Reference Example 16
(+/−) -N-[3,5-Bis(trifluoromethyl)benzyl)-7,8-dihydro-7-(4-hydroxy-3-methylbutyl)-8-oxo-5-phenyl-6-pyrido[3,4-b]pyridinecarboxamide The compound as obtained in Step 3 in Reference Example 9 was reacted with 4-amino-2-methyl-1-butanol and treated in the same manner as in Reference Example 13, to obtain the entitled compound as colorless crystals. m.p. 217–219° C. (recrystallized from ethyl acetate-isopropyl ether).

Reference Example 17
(+/−)-N-[3,5-Bis(trifluoromethyl)benzyl]-7,8-dihydro-7-(4-hydroxy-3-methylbutyl)-5-(4-methylphenyl)-8-oxo-6-pyrido[3,4-b]pyridinecarboxamide The compound as obtained in Reference Example 3 was reacted with 4-amino-2-methyl-1-butanol and treated in the same manner as in Reference Example 13, to obtain the entitled compound as colorless crystals. m.p. 129–130° C. (after once melted, this again solidified), 188–190° C. (re-melted) (recrystallized from ethyl acetate-isopropyl ether) NMR(200 MHz, CDCl$_3$) ppm: 0.79(3H,d,J=6.6 Hz), 1.4–1.8 (3H,m), 2.28(3H,s), 3.03(1H,t,J=6.6 Hz,—OH), 3.2–3.7 (4H,m), 4.49(2H,d,J=5.8 Hz), 7.0–7.3(4H,m), 7.30(1H,dd, J=8.4,4.4 Hz), 7.53(1H,dd,J=8.4,1.4 Hz), 7.68(2H,s), 7.78 (1H,s), 8.48(1H,t,J=6.0 Hz), 8.61(1H,dd,J=4.4,1.4 Hz).

Reference Example 18
(R)-N-[3,5-Bis(trifluoromethyl)benzyl]-7,8-dihydro-7-(4-hydroxy-3-methylbutyl)-8-oxo-5-phenyl-6-pyrido[3,4-b]pyridinecarboxamide The compound as obtained in Step 4 in Reference Example 9 was reacted with (R)-4-amino-2-methyl-1-butanol tetrahydropyranyl (THP) ether and treated in the same manner as in Reference Example 13, to obtain THP ether of the entitled compound as a pale orange oil. This compound was reacted with p-toluenesulfonic acid in methanol at room temperature to thereby remove the THP group, and the entitled compound was obtained as colorless

Reference Example 19
(R)-N-[3,5-Bis(trifluoromethyl)benzyl]-7,8-dihydro-7-(4-hydroxy-3-methylbutyl)-5-(4-methylphenyl)-8-oxo-6-pyrido[3,4-b]pyridinecarboxamide The compound as obtained in Reference Example 3 was reacted with (R)-4-amino-2-methyl-1-butanol THP ether and treated in the same manner as in Reference Example 13, to obtain THP ether of the entitled compound as a pale orange oil. This compound was reacted with p-toluenesulfonic acid in methanol at room temperature to thereby remove the THP group, and the entitled compound was obtained as colorless crystals. m.p. 123–125° C. (after once melted, this again solidified), 205–206° C. (re-melted) (recrystallized from ethyl acetate-isopropyl ether) NMR(200 MHz, CDCl$_3$) ppm: same as the spectrum of the compound of Reference Example 17. $[\alpha]_D$: +1.2° (C=0.471,CHCl$_3$).

Reference Example 20
(S)-N-[3,5-Bis(trifluoromethyl)benzyl]-7,8-dihydro-7-(4-hydroxy-3-methylbutyl)-8-oxo-5-phenyl-6-pyrido[3,4-b]pyridinecarboxamide (S)-4-Amino-2-methyl-1-butanol THP ether was used in place of (R)-4-amino-2-methyl-1-butanol THP ether in Reference Example 18 and reacted and treated in the same manner as in Reference Example 18, to obtain the entitled compound as colorless crystals. m.p. 213–214° C. (recrystallized from ethyl acetate-ethyl ether) NMR(200 MHz, CDCl$_3$) ppm: same as the spectrum of the compound of Reference Example 16. $[\alpha]_D$: −1.5° (C=0.492,CHCl$_3$).

Reference Example 21
(S)-N-[3,5-Bis(trifluoromethyl)benzyl]-7,8-dihydro-7-(4-hydroxy-3-methylbutyl)-5-(4-methylphenyl)-8-oxo-6-pyrido[3,4-b]pyridinecarboxamide (S)-4-Amino-2-methyl-1-butanol THP ether was used in place of (R)-4-amino-2-methyl-1-butanol THP ether in Reference Example 19 and reacted and treated in the same manner as in Reference Example 19, to obtain the entitled compound as colorless crystals. m.p. 213–215° C. (after once melted, this again solidified), 207–208° C. (re-melted) (recrystallized from ethyl acetate-isopropyl ether) NMR(200 MHz, CDCl$_3$) ppm: same as the spectrum of the compound of Reference Example 17. $[\alpha]_D$: −2.7° (C=0.391,CHCl$_3$).

Reference Example 22
N-(2-Aminoethyl)-N-[3,5-bis(trifluoromethyl)benzyl]-2-chloro-4-phenyl-3-pyridinecarboxamide Step 1

Thionyl chloride (0.15 ml) and DMF (catalytic amount) were added to a THF (5 ml) solution of 2-chloro-4-phenyl-3-pyridinecarboxylic acid (145 mg) and heated under reflux for 2 hours. The solvent was removed by distillation, and the residue was dissolved in THF (5 ml). The resulting solution was added to a mixture of N-[3,5-bis(trifluoromethyl)benzyl]-N'-tert-butoxycarbonylethylenediamine (240 mg), triethylamine (0.26 ml) and THF (10 ml), while cooling with ice, and stirred for 3 hours at room temperature. The N-[3,5-bis(trifluoromethyl)benzyl]-N'-tert-butoxycarbonylethylenediamine used herein was prepared as an oily compound, by reacting ethylenediamine with 3,5-bis(trifluoromethyl)benzyl methanesulfonate in THF to give an oily compound of N-[3,5-bis(trifluoromethyl)benzyl]ethylenediamine, followed by further reacting the compound with di-tert-butyl dicarbonate in the presence of triethylamine in THF.

The solvent was removed from the reaction mixture, and water was added to the residue, which was then extracted with ethyl acetate. The extract was washed with water and dried, and the solvent was removed by distillation. Thus, obtained was N-[3,5-bis(trifluoromethyl)benzyl]-N-[2-(tert-butoxycarbonylamino)ethyl]-2-chloro-4-phenyl-3-pyridinecarboxamide as a pale yellow oil. NMR(200 MHz, CDCl$_3$) ppm: 1.20–1.60(total 9H,m), 2.70–4.90(total 7H,m), 7.20–8.00(total 9H,m), 8.46(1H,d,J=5.2 Hz).

Step 2

A 4N-HCl/ethyl acetate solution (10 ml) was added to the compound as obtained in Step 1 and stirred for 30 minutes at room temperature. The solvent was removed by distillation, and aqueous sodium hydrogencarbonate was added to the residue, which was then extracted with ethyl acetate. The extract was washed with water and then dried, and the solvent was removed by distillation. Thus, the entitled compound was obtained as a pale yellow oil (349 mg). NMR(200 MHz, CDCl$_3$) ppm: 2.30–3.70(4H,m), 4.15 (1H×²⁄₅,d,J=16.2 Hz), 4.38(1H×²⁄₅,d,J=16.2 Hz), 4.65(1H×³⁄₅,d,J=15.2 Hz), 4.84(1H×³⁄₅,d,J=15.2 Hz), 7.20–7.60(6H,m), 7.65–7.80(6H,m), 8.47(1H,m).

Reference Example 23
N-[3,5-Bis(trifluoromethyl)benzyl]-2-chloro-N-(3-hydroxypropyl)-4-phenyl-3-pyridinecarboxamide Step 1

3-Amino-1-propanol was used in place of 2-aminoethanol in Step 1 in Reference Example 12, reacted and treated in the same manner as in Step 1 in Reference Example 12, to obtain N-[3,5-bis(trifluoromethyl)benzyl]-N-(3-hydroxypropyl)amine as colorless crystals. m.p. 57–58° C. (recrystallized from ethyl ether-hexane) NMR(200 MHz, CDCl$_3$) ppm: 1.77(2H,quintet,J=5.8 Hz), 2.89(2H,t,J=5.8 Hz), 3.82(2H,t,J=5.8 Hz), 3.93(2H,s), 7.89(3H,s) Elemental Analysis for C$_{12}$H$_{13}$NOF$_6$: Calcd.(%): C, 47.85; H, 4.35; N, 4.65. Found (%): C, 47.76; H, 4.32; N, 4.65.

Step 2

The amine as obtained in Step 1 was used in place of N-[3,5-bis(trifluoromethyl)benzyl]-N-(2-hydroxyethyl)amine in Step 2 in Reference Example 12 reacted and treated in the same manner as in Step 2 in Reference Example 12, to obtain the entitled compound as colorless crystals (the ratio of cis-trans isomers with respect to the amide bond was about 3:1). m.p. 121–122° C. (recrystallized from ethyl acetate-isopropyl ether) NMR(200 MHz, CDCl$_3$) ppm: 1.00–1.70(2H,m), 2.75–3.20(2H,m), 3.35–3.55(3H,m), 4.06 (1H×¼,d,J=16.2 Hz), 4.31(1H×¼,d,J=16.2 Hz), 4.65(1H×¾,d,J=15.2 Hz), 4.76(1H×¾,d,J=15.2 Hz), 7.20–7.55(6H,m), 7.72(2H,s), 7.80(1H,s), 8.47(1H,d,J=5.2 Hz) Elemental Analysis for C$_{24}$H$_{19}$N$_2$O$_2$F$_6$Cl: Calcd.(%): C, 55.77; H, 3.71; N, 5.42. Found (%): C, 55.65; H, 3.70; N, 5.57.

Reference Example 24
N-[3,5-Bis(trifluoromethyl)benzyl]-2-chloro-N-(2-hydroxyethyl)-5-methyl-4-phenyl-3-pyridinecarboxamide 2-Chloro-5-methyl-4-phenyl-3-pyridinecarboxylic acid was used in place of 2-chloro-4-phenyl-3-pyridinecarboxylic acid in Step 2 in Reference Example 12, reacted and treated in the same manner as in Step 2 in Reference Example 12, to obtain the entitled compound as colorless crystals. m.p. 146–148° C. (recrystallized from ethyl acetate-isopropyl ether) NMR(200 MHz, CDCl$_3$) ppm: 2.09(3H,s), 3.02(1H,dt,J=15.0,5.6 Hz), 3.25(1H,dt,J=15.0, 5.6 Hz), 3.60(2H,m), 4.57(1H,d,J=15.2 Hz), 4.79(1H,d,J= 15.2 Hz), 7.05–7.50(5H,m), 7.62(2H,s), 7.76(1H,s), 8.33 (1H,s).

Reference Example 25
N-[3,5-Bis(trifluoromethyl)benzyl]-2-chloro-N-(3-hydroxypropyl)-5-methyl-4-phenyl-3-pyridinecarboxamide 2-Chloro-5-methyl-4-phenyl-3-pyridinecarboxylic acid was used in place of 2-chloro-4-phenyl-3-pyridinecarboxylic acid in Step 2 in Reference Example 12, reacted with N-[3,5-bis(trifluoromethyl)benzyl]-N-(3-hydroxypropyl)amine that had been obtained in Step 1 in Reference Example 23, in place of N-[3,5-bis(trifluoromethyl)benzyl]-N-(2-hydroxyethyl)amine, and treated in the same manner as in Step 2 in Reference Example 12, to obtain the entitled compound as a pale yellow oil. NMR(200 MHz, CDCl$_3$) ppm: 1.10–1.80(2H,m), 2.06(3H×½,s), 2.08(3H×½,s), 2.80–3.30(3H,m), 3.35–3.70 (1H,m), 4.08(1H×½,d,J=16.4 Hz), 4.39(1H×½,d,J=15.0 Hz), 4.47(1H×½,d,J=16.4 Hz), 4.70(1H×½,d,J=15.0 Hz), 6.90–7.62(7H,m), 7.72(1H×½,s), 7.77(1H×½,s), 8.28(1H×½,s), 8.31(1H×½,s).

Reference Example 26
(+/−)-N-[3,5-Bis(trifluoromethyl)benzyl]-7,8-dihydro-7-(2,3-dihydroxypropyl)-5-(4-methylphenyl)-8-oxo-6-pyrido[3,4-b]pyridinecarboxamide The compound as obtained in Reference Example 3 was reacted with (+/−)-3-amino-1,2-propanediol and treated in the same manner as in Reference Example 13, to obtain the entitled compound as a pale yellow foam. NMR(200 MHz, CDCl$_3$) ppm: 2.20(3H,s), 3.50(2H,m), 4.02–4.30(5H,m), 4.75(1H,b), 5.35(1H,b), 6.92–7.46(6H,m), 7.55(2H,s), 7.70 (1H,s), 8.63(1H,m), 8.83(1H,b).

Reference Example 27
N-Benzyl-8-oxo-5-phenyl-8H-pyrano[3,4-b]pyridine-6-carboxamide The compound as obtained in Step 2 in Reference Example 9 was reacted with benzylamine and treated in the same manner as in Reference Example 3, to obtain the entitled compound as colorless crystals. m.p. 188–189° C. (recrystallized from acetone-ethyl ether) NMR(200 MHz, CDCl$_3$) ppm: 4.48(2H,d,J=5.4 Hz), 7.2–7.4(8H,m), 7.49–7.65(5H,m), 8.95(1H,dd,J=4.4,2.0 Hz)

Reference Example 28
N-(3,4-Dichlorobenzyl)-B-oxo-5-phenyl-8H-pyrano[3,4-b]pyridine-6-carboxamide The compound as obtained in Step 2 in Reference Example 9 was reacted with 3,4-dichlorobenzylamine and treated in the same manner as in Reference Example 3, to obtain the entitled compound as colorless crystals. m.p. 198–200° C. (recrystallized from acetone-ethyl ether) NMR (200 MHz, CDCl$_3$) ppm: 4.44(2H,d,J=6.0 Hz), 7.10(1H,dd, J=8.2,2.0 Hz), 7.25–7.70(10H,m), 8.96(1H,dd,J=4.3,1.7 Hz)

Reference Example 29
N-(3,5-Bis(trifluoromethyl)benzyl]-2-chloro-N-((S)-3-hydroxy-2-methylpropyl]-5-methyl-4-phenyl-3-pyridinecarboxamide The same process as in Step 2 in Reference Example 12 was repeated, except that 2-chloro-5-methyl-4-phenyl-3-pyridinecarboxylic acid was reacted with N-[3,5-bis(trifluoromethyl)benzyl]-N-[(S)-3-hydroxy-2-methylpropyl]amine [this was prepared by reacting 3,5-bis(trifluoromethyl)benzyl methanesulfonate with (S)-3-amino-2-methylpropanol in THF, and this is a colorless oily substance and was identified by NMR(200 MHz, CDCl$_3$) ppm: 0.86(3H,d,J=6.8 Hz), 1.98(1H,m), 2.63(1H,dd,J=9.4, 11.8 Hz), 2.70–2.90(3H,m), 3.56(1H,dd,J=8.6,10.6 Hz), 3.71(1H,ddd,J=1.4,4.0,10.6 Hz), 3.87(1H,d,J=13.8 Hz), 3.98(1H,d,J=13.8 Hz), 7.79(3H,s)] in place of reacting 2-chloro-4-phenyl-3-pyridinecarboxylic acid with N-[3,5-bis(trifluoromethyl)benzyl]-N-(2-hydroxyethyl)amine, to obtain the entitled compound as a colorless oily substance. NMR(200 MHz, CDCl$_3$) ppm: 0.60–0.82(3H,m), 1.50–2.00 (1H,m), 2.00–2.15(3H,m), 2.15–3.92(4H,m), 4.05–4.92(2H, m), 7.00–7.85(8H,m), 8.34(1H,m)

Reference Example 30
N-[3,5-Bis(trifluoromethyl)benzyl]-2-chloro-N-[(R)-3-hydroxy-2-methylpropyl]-5-methyl-4-phenyl-3-pyridinecarboxamide N-[3,5-Bis(trifluoromethyl)benzyl]-N-[(R)-3-hydroxy-2-methylpropyl]amine was reacted and treated in the same manner as in Reference Example 29, in place of N-[3,5-bis(trifluoromethyl)benzyl]-N-[(S)-3-hydroxy-2-methylpropyl]amine in Reference Example 29, to obtain the entitled compound as a colorless oily substance. The NMR spectrum (200 MHz, CDCl$_3$) of the compound obtained herein was the same as that of the compound obtained in Reference Example 29.

Reference Example 31
N-[3,5-Bis(trifluoromethyl)benzyl]-2-chloro-N-(2-hydroxyethyl)-6-methyl-4-phenyl-3-pyridinecarboxamide Step 1

A mixture of ethyl 2-chloro-6-methyl-4-phenyl-3-pyridinecarboxylate (15.43 g), ethanol (70 ml) and aqueous 4N-sodium hydroxide solution (70 ml) was heated under reflux for 2.5 hours. The reaction mixture was concentrated, and the resulting concentrate was made acidic (pH 3) by adding hydrochloric acid thereto and then extracted with ethyl acetate. The extract was washed with saturated aqueous sodium chloride solution and dried, and the solvent was removed by distillation. Thus, obtained was 2-chloro-6-methyl-4-phenyl-3-pyridinecarboxylic acid as colorless crystals (11.2 g). m.p. 191–194° C. (recrystallized from ethyl acetate-isopropyl ether) NMR(200 MHz, CDCl$_3$) ppm: 2.59(3H,s), 7.16(1H,s), 7.45(5H,s), 9.53(1H,b)

Step 2

In place of 2-chloro-4-phenyl-3-pyridinecarboxylic acid in Step 2 in Reference Example 12, 2-chloro-6-methyl-4-phenyl-3-pyridinecarboxylic acid (as obtained in the previous Step 1) was reacted and treated in the same manner as in Step 2 in Reference Example 12, to obtain the entitled compound as a pale-yellow, oily substance. NMR(200 MHz, CDCl$_3$) ppm: 1.95–3.80(4H,m), 2.58(3H,s), 4.15(1H×⅖,d, J=16.2 Hz), 4.41(1H×⅖,d,J=16.2 Hz), 4.75(1H×⅗,d,J=15.0 Hz), 4.85(1H×⅗,d,J=15.0 Hz), 7.15(1H×⅗,s), 7.17(1H×⅖, d,J=15.0 Hz), 7.23–7.58(5H,m), 7.74(2H,s), 7.78(1H,s)

Reference Example 32
N-[3,5-Bis(trifluoromethyl)benzyl]-2-chloro-N-(3-hydroxypropyl)-6-methyl-4-phenyl-3-pyridinecarboxamide The same process as in Step 2 in Reference Example 12 was repeated, except that 2-chloro-6-methyl-4-phenyl-3-pyridinecarboxylic acid was reacted with N-[3,5-bis(trifluoromethyl)benzyl]-N-(3-hydroxypropyl)amine in place of reacting 2-chloro-4-phenyl-3-pyridinecarboxylic acid with N-[3,5-bis(trifluoromethyl)benzyl]-N-(2-hydroxyethyl)amine, to obtain the entitled compound as a pale-yellow, oily substance. NMR(200 MHz, CDCl$_3$) ppm: 1.15–1.65(2H,m), 2.59(3H,s), 2.75–3.20(2H,m), 4.06(1H×⅖,d,J=15.4 Hz), 4.31(1H×⅖,d,J=15.4 Hz), 4.65 (1H×⅗,d,J=15.2 Hz), 4.74(1H×⅗,d,J=15.2 Hz), 7.16(1H,s), 7.20–7.60(5H,m), 7.72(2H,s), 7.78(1H,s)

Reference Example 33
N-[3,5-Bis(trifluoromethyl)benzyl]-N-(2-hydroxyethyl)-5-methyl-2-methylaminocarbonyl-4-phenyl-3-pyridinecarboxamide Step 1

A mixture of diethyl 5-methyl-4-phenyl-2,3-pyridinedicarboxylate (13.0 g) [this was prepared in accordance with the method described in Japanese Patent Laid-Open No. 62-106081, and this has a melting point of 73–74° C. (after recrystallized from ethyl ether-isopropyl ether)], potassium hydroxide (20 g) and 70%-ethanol (200 ml) was heated under reflux for 3 hours. The solvent was removed by distillation, and the residue was diluted with water and then washed with ethyl ether. The PH of the aqueous layer was adjusted to 2–3 by adding 2 N-hydrochloric acid, and then extracted with ethyl acetate. The extract was washed with saturated saline solution and dried, and the solvent was removed by distillation. Thus, obtained was 5-methyl-4-phenyl-2,3-pyridinedicarboxylic acid as pale yellow crystals (3.06 g). m.p. 187–188° C. (recrystallized from THF-ethyl ether) NMR(200 MHz, DMSO-$d_6$) ppm: 2.10(3H,s), 7.20–7.30(2H,m), 7.40–7.55(3H,m), 8.65(1H,s)

Step 2

The compound (2.9 g) as obtained in the previous Step 1 was heated in acetic anhydride (50 ml) under reflux for 2 hours. The solvent was removed by distillation, and ethanol (50 ml) was added to the residue and stirred for 4 hours at room temperature. Then, the solvent was removed by distillation, and the residue was dissolved in ethyl acetate. The resulting solution was washed with saturated saline solution and dried, and the solvent was removed by distillation. Thus, obtained was a mixture of 2-ethyl ester and 3-ethyl ester (about 3:2) of 5-methyl-4-phenyl-2,3-pyridinedicarboxylic acid as a pale-brown, oily substance (3.39 g).

Step 3

DMF (3 drops) and oxalyl chloride (2.0 ml) were added to a THF (30 ml) solution of the oily substance (1.94 g) as obtained in Step 2, and stirred for 30 minutes at room temperature. The solvent was removed by distillation, and the residue was dissolved in THF (40 ml). N-[3,5-Bis(trifluoromethyl)benzyl]-N-(2-hydroxyethyl)amine (2.2 g) and triethylamine (2.0 ml) were added to the resulting solution and stirred for 16 hours at room temperature. The reaction mixture was diluted with ethyl acetate, then washed with water, diluted hydrochloric acid, aqueous potassium carbonate solution and saturated saline solution, and dried. The solvent was removed by distillation, and the residue was purified by column chromatography (hexane:ethyl acetate= 1:2) using silica gel to obtain N-[3,5-bis(trifluoromethyl)benzyl]-2-ethoxycarbonyl-N-(2-hydroxyethyl)-5-methyl-4-phenyl-3-pyridinecarboxamide as colorless crystals (1.31 g). m.p. 138–139° C. (recrystallized from ethyl acetate-isopropyl ether) NMR(200 MHz, CDCl$_3$) ppm: 1.45(3H×¼, t,J=7.1 Hz), 1.46(3H×¾,t,J=7.1 Hz), 2.18(3H×¾,s), 2.19 (3H×¼,s), 2.82(1H,m), 3.2–3.7(3H,m). 4.15–4.62(4H,m), 7.05–7.80(8H,m), 8.65(1H×¾,s), 8.68(1H×¼,s)

Step 4

40% Methylamine-methanol solution (15 ml) was added to a THF (5 ml) solution of the compound (377 mg) as obtained in Step 3 and stirred for 16 hours at room temperature. The solvent was removed by distillation, and the entitled compound was obtained as a pale-yellow, oily substance (370 mg). NMR(200 MHz, CDCl$_3$) ppm: 2.12 (3H×⅔,s), 2.14(3H×⅓,s), 2.83(1H,m), 3.03(3H×⅓,d,J=5.2 Hz), 3.04(3H×⅔,d,J=4.8 Hz), 3.25–3.80(3H,m), 4.30(1H×⅔,d,J=15 Hz), 4.36(1H×⅓,d,J=15 Hz), 4.59(1H× ⅓,d,J=15 Hz), 4.86(1H×⅔,d,J=15Hz), 7.0–7.9(8H,m), 8.02 (1H,⅔,bd), 8.17(1H×⅓,bd), 8.46(1H,s)

Reference Example 34
N-[3,5-Bis(trifluoromethyl)benzyl]-N-(2-hydroxyethyl)-2-methylaminocarbnyl-4-phenyl-3-pyridinecarboxamide Step 1

In place of diethyl 5-methyl-4-phenyl-2,3-pyridinedicarboxylate in Step 1 in Reference Example 33, diethyl 4-phenyl-2,3-pyridinedicarboxylate (see Japanese Patent Laid-Open No. 62-106081) was reacted and treated in the same manner as in Step 1 in Reference Exaple 33, to obtain 4-phenyl-2,3-pyridinedicarboxylic acid as pale yellow crystals. m.p. 146–148° C. (recrystallized from THF-isopropyl ether) NMR(200 MHz, CDCl$_3$+DMSO-$d_6$) ppm: 7.3–7.6(6H,m), 8.69(1H,d,J=5.0 Hz)

Step 2

The compound as obtained in Step 1 was reacted and treated in the same manner as in Step 2 in Reference Example 33, to obtain a mixture of 2-ethyl ester and 3-ethyl ester (about 3:2) of 4-phenyl-2,3-pyridinedicarboxylic acid as a pale-brown, oily substance.

Step 3

The oily substance as obtained in Step 2 was reacted and treated in the same manner as in Step 3 in Reference Example 33, to obtain N-[3,5-bis(trifluoromethyl)benzyl]-2-ethoxycarbonyl-N-(2-hydroxyethyl)-4-phenyl-3-pyridinecarboxamide as a pale-yellow, oily substance. NMR (200 MHz, CDCl$_3$) ppm: 1.48(3H,t,J=7.1 Hz.), 2.71(1H,m), 3.1–3.7(3H,m), 4.1–4.9(4H,m), 7.18–7.52(6H,m), 7.65–7.82(3H,m), 8.78(1H×3.4,d,J=4.8 Hz), 8.80(1H×¼,d,J=4.8 Hz)

Step 4

The compound as obtained in Step 3 was reacted and treated in the same manner as in Step 4 in Reference Example 33, to obtain the entitled compound as a pale-yellow, oily substance. NMR(200 MHz, CDCl$_3$) ppm: 2.73 (1H,m), 3.05(3H×⅓,d,J=5.0 Hz), 3.06(3H×⅔,d,J=5.0 Hz), 3.1–3.9(3H,m), 4.29(1H×⅓,d,J=16 Hz), 4.52(1H×⅔,d,J=15 Hz), 4.54(1H×⅓,d,J=16 Hz), 4.93(1H×⅔,d,J=15 Hz), 7.0–7.9(9H,m), 7.95(1H×⅔,bd), 8.19(1H×⅓,bd), 8.59(1H, d,J=5.2 Hz)

Reference Example 35
N-Benzyl-2-ethoxycarbonyl-N-(2-hydroxyethyl)-5-methyl-4-phenyl-3-pyridinecarboxamide The oily substance as obtained in Step 2 in Reference Example 33 was reacted with N-benzyl-N-(2-hydroxyethyl) amine and treated in the same manner as in Step 3 in Reference Example 33, to obtain the entitled compound as a pale-yellow, oily substance. NMR(200 MHz, CDCl$_3$) ppm: 1.44(3H×¼,t,J=7.2 Hz), 1.46(3H×¾,t,J=7.1 Hz), 2.15(3H×¾,s), 2.19(3H×¼,s), 2.6–3.7(4H,m), 3.96(1H×¾, d,J=15 Hz), 4.00(1H×¼,d,J=15 Hz), 4.4–4.6(2H+1H×¼,m), 5.37(1H×¾,d,J=15 Hz), 6.48(2H×¾,m), 6.82(2H×¼,m), 7.0–7.6(8H,m), 8.65(1H×3.4,s), 8.66(1H×¼,s)

Reference Example 36
N-[3,5-Bis(trifluoromethyl)benzyl]-N-(3-hydroxypropyl)-5-methyl-2-methylaminocarbonyl-4-phenyl-3-pyridinecarboxamide Step 1

The oily substance as obtained in Step 2 in Reference Example 33 was reacted with N-[3,5-bis(trifluoromethyl) benzyl]-N-(3-hydroxypropyl)amine and treated in the same manner as in Step 3 in Reference Example 33 to obtain N-[3,5-bis(trifluoromethyl)benzyl]-2-ethoxycarbonyl-N-(3-hydroxypropyl)-5-methyl-4-phenyl-3-pyridinecarboxamide as a pale-yellow, oily substance. NMR(200 MHz, CDCl₃) ppm: 1.44(3H×¼,t,J=7.1 Hz), 1.45(3H×¾,t,J=7.1 Hz), 1.60 (2H,m), 2.17(3H×¾,s), 2.18(3H×¼,s), 2.7–3.7(4H,m), 3.96 (1H×¼,d,J=16 Hz), 4.35–4.60(3H+1H×¾,m), 7.10–7.80 (8H,m), 8.64(1H×¾,s), 8.68(1H×¼,s)

Step 2

The compound as obtained in Step 1 was reacted and treated in the same manner as in Step 4 in Reference Example 33 to obtain the entitled compound as a pale-yellow, oily substance. NMR(200 MHz, CDCl₃) ppm: 1.3–1.9(2H,m), 2.11(3H×⅗,s), 2.14(3H×⅖,s), 2.7–3.8(4H, m), 3.02(3H×⅗,d,J=5.2 Hz), 3.03(3H×⅖,d,J=5.2 Hz), 4.04 (1H×⅖,d,J=16 Hz), 4.28(1H×⅗,d,J=15 Hz), 4.46(1H×⅖,d, J=16 Hz), 4.82(1H×⅗,d,J=15 Hz), 7.0–7.6(5H,m), 7.63 (2H⅗,s), 7.67(2H×⅖,s), 7.73(1H,s), 7.96(1H×⅗,bd), 8.06 (1H×⅖,bd), 8.45(1H×⅗,s), 8.48(1H×⅖,s)

Reference Example 37

2-Chloro-N-(2-hydroxyethyl)-4-phenyl-N-(3,4,5-trimethoxybenzyl)-3-pyridinecarboxamide NMR(200 MHz, CDCl₃) ppm: 2.05–2.50(2H,m), 2.80–4.00(12H,m), 4.00–4.40(1H×½,m), 4.93(1H×½,d,J= 14.2 Hz), 6.22(2H×½,s), 6.55(2H×½,s), 7.25–7.70(6H,m), 8.42(1H×½,d,J=6.2 Hz), 8.48(1H×½,d,J=5.8 Hz) (a 1:1 mixture of the amide rotamers).

Reference Example 38

2-Chloro-N-(3,4-dichlorobenzyl)-N-(2-hydroxyethyl)-4-phenyl-3-pyridinecarboxamide NMR(200 MHz, CDCl₃) ppm: 1.80–3.85(5H,m), 3.96 (1H×⅘,d,J=16.0 Hz), 4.24(1H×⅘,d,J=16.0 Hz), 4.44(1H× ⅝,d,J=15.2 Hz), 4.92(1H×⅝,d,J=15.2 Hz), 6.50–6.85(2H, m), 7.10–7.70(7H,m), 8.46(1H,m) (a 5:4 mixture of the amide rotamers).

Reference Example 39

2-Chloro-N-(3,4-dimethoxybenzyl)-N-(2-hydroxyethyl)-4-phenyl-3-pyridinecarboxamide NMR(200 MHz, CDCl₃) ppm: 2.70–4.30(12H,m), 4.53 (1H×½,d,J=14.8 Hz), 4.74(1H×½,d,J=14.8 Hz), 6.30–7.00 (3H,m), 7.20–7.65(6H,m), 8.39(1H×½,d,J=5.0 Hz), 8.46 (1H×½,d,J=5.2 Hz) (a 1:1 mixture of the amide rotamers).

Reference Example 40

N-Benzyl-2-chloro-N-(2-hydroxyethyl)-4-phenyl-3-pyridinecarboxamide

NMR(200 MHz, CDCl₃) ppm: 2.27(1H×½,b), 2.60(1H× ½,b), 2.75–3.15(1H,m), 3.25–3.65(3H,m), 3.90(1H×½,d,J= 15.4 Hz), 4.26(1H×½,d,J=15.4 Hz), 4.49(1H×½,d,J=15.0 Hz), 4.95(1H×½,d,J=15.0 Hz), 6.74(2H×½,m), 6.92(2H×½, m), 7.10–7.65(9H,m), 8.42(1H,m) (a 1:1 mixture of the amide rotamers).

Reference Example 41

2-Chloro-N-(3-hydroxypropyl)-4-phenyl-N-(3,4,5-trimethoxybenzyl)-3-pyridinecarboxamide NMR(200 MHz, CDCl₃) ppm: 1.10–2.30(3H,m), 2.70–4.30(14H+1H×3/7,m), 4.88(1H×4/7,d,J=14.8 Hz), 6.18 (2H×4/7,s), 6.52(2H×3/7,s), 7.20–7.60(6H,m), 8.47(1H,m) (a 4:3 mixture of the amide rotamers).

Reference Example 42

N-Benzyl-2-chloro-N-[(S)-3-hydroxy-2-methylpropyl]-4-phenyl-3-pyridinecarboxamide NMR(200 MHz, CDCl₃) ppm: 0.50–0.85(3H,m), 1.40–1.85(1H,m), 2.20–3.75(5H,m), 3.80–5.15(2H,m), 6.60–7.65(11H,m), 8.42(1H,m) (a 2:1 mixture of the amide rotamers).

Reference Example 43

N-Benzyl-2-chloro-N-[(R)-3-hydroxy-2-methylpropyl]-4-phenyl-3-pyridinecarboxamide MR(200 MHz, CDCl₃) ppm: same as the spectrum of the compound of Reference Example 42.

Reference Example 44

N-[3,5-Bis(trifluoromethyl)benzyl]-2-chloro-N-[(S)-3-hydroxy-2-methylpropyl]-4-phenyl-3-pyridinecarboxamide NMR(200 MHz, CDCl₃) ppm: 0.53(3H×¼,d,J=7.0 Hz), 0.63(3H×¼,d,J=7.0 Hz), 0.75(3H×¼,d,J=6.8 Hz), 0.81(3H× ¼,d,J=6.8 Hz), 1.50–1.90(1H,m), 2.42–3.80(5H,m), 4.00–4.95(2H,m), 7.10–7.90(9H,m), 8.42(1H,m) (a 1:1 mixture of the amide rotamers).

Reference Example 45

N-[3,5-Bis(trifluoromethyl)benzyl]-2-chloro-N-[(R)-3-hydroxy-2-methylpropyl]-4-phenyl-3-pyridinecarboxamide NMR(200 MHz, CDCl₃) ppm: same as the spectrum of the compound of Reference Example 44.

Reference Example 46

N-Benzyl-7,8-dihydro-7-(4-hydroxybutyl)-5-(4-methylphenyl)-8-oxo-6-pyrido[3,4-b]pyridinecarboxamide Step 1

Using the compound as obtained in Reference Example 2-Step 2 and benzylamine, substantially the same reaction and work-up as Reference Example 2-Step 4 was conducted to give N-benzyl-5-(4-methylphenyl)-8-oxo-8H-pyrano[3, 4-b]pyridine-6-carboxamide as colorless crystals. m.p. 208–209° C. (recrystallized from acetone-isopropyl ether) NMR(200 MHz, CDCl₃) ppm: 2.45(3H,s), 4.48(2H,d,J=5.6 Hz), 7.10–7.40(10H,m), 7.58(2H,m), 8.94(1H,dd,J=3.6&2.2 Hz).

Step 2

Using the compound as obtained in Step 1 and 4-amino-1-butanol, substantially the same reaction and work-up as Reference Example 13 was conducted to give the entitled compound as colorless crystals. m.p. 205–207° C. (recrystallized from acetone-isopropyl ether) NMR(200 MHz, CDCl₃) ppm: 1.48(2H,m), 1.83(2H,m), 2.45(3H,s), 2.86(1H,b), 3.57(2H,t,J=5.9 Hz), 3.85(2H,m), 4.34(2H,d,J= 6.0 Hz), 6.8–7.1(2H,m), 7.10–7.35(8H,m), 7.50(1H,m), 7.55 (1H,dd,J=8.4&1.4 Hz), 8.60(1H,dd,J=4.0&1.4 Hz).

Reference Example 47

(R)-N-Benzyl-7,8-dihydro-7-(4-hydroxy-3-methylbutyl)-5-(4-methylphenyl)-8-oxo-6-pyrido[3,4-b]pyridinecarboxamide Starting from the compound as obtained in Reference Example 46-Step 1 and THP-ether of (R)-4-amino-2-methyl-1-butanol, substantially the same reaction and work-up as Reference Example 19 was conducted to give the entitled compound as colorless crystals. m.p. 226–227° C. (recrystallized from acetone-ethyl ether) NMR(200 MHz, CDCl₃) ppm: 0.81(3H,d,J=6.6 Hz), 1.5–2.0(3H,m), 2.44 (3H,s), 3.20–3.55(3H,m), 3.93(2H,m), 4.31(2H,d,J=5.4 Hz), 6.75–6.90(2H,m), 7.1–7.3(8H,m), 7.39(1H,dd,J=8.2&4.2 Hz), 7.61(1H,d,J=8.2 Hz), 8.68(1H,d,J=4.2 Hz).

Reference Example 48

(S)-N-Benzyl-7,8-dihydro-7-(4-hydroxy-3-methylbutyl)-5-(4-methylphenyl)-8-oxo-6-pyrido[3,4-b]pyridinecarboxamide Starting from the compound as obtained in Reference Example 46-Step 1 and THP-ether of (S)-4-amino-2-methyl-1-butanol, substantially the same reaction and work-up as Reference Example 19 was conducted to give the entitled compound as colorless crystals. m.p. 226–227° C. (recrystallized from acetone-ethyl ether) NMR(200 MHz, CDCl₃) ppm: same as the spectrum of the compound of Reference Example 47.

Reference Example 49

(R)-7,8-Dihydro-7-(4-hydroxy-3-methylbutyl)-5-(4-methylphenyl)-8-oxo-N-(3,4,5-trimethoxybenzyl)-6-pyrido[3,4-b]pyridinecarboxamide Step 1

Using the compound as obtained in Reference Example 2-Step 2 and 3,4,5-trimethoxybenzylamine, substantially the same reaction and work-up as Reference Example 2-Step 4 was conducted to give 5-(4-methylphenyl)-8-oxo-N-(3,4,5-trimethoxybenzyl)-8H-pyrano[3,4-b]pyridine-6-carboxamide as colorless crystals. m.p. 195–196° C. (recrystallized from acetone-isopropyl ether) NMR(200 MHz, CDCl₃) ppm: 2.45(3H,s), 3.84(3H,s), 3.85(6H,s), 4.40 (2H,d,J=5.8 Hz), 6.50(2H,s), 7.17(2H,d,J=8.0 Hz), 7.27(1H, b), 7.32(2H,d,J=8.0 Hz), 7.58(2H,m), 8.94(1H,dd,J=4.0&2.2 Hz).

Step 2

Starting from the compound as obtained in Step 1 and THP-ether of (R)-4-amino-2-methyl-1-butanol, substantially the same reaction and work-up as Reference Example 19 was conducted to give the entitled compound as colorless crystals. m.p. 194–195° C. (recrystallized from acetone-ethyl ether) NMR(200 MHz, CDCl₃) ppm: 0.84(3H,d,J=6.8Hz), 1.5–2.0(3H,m), 2.38(3H,s), 3.2–3.6(3H,m), 3.65–3.95(2H,m), 3.80(6H,s), 3.82(3H,s), 4.23(2H,d,J=6.0 Hz), 6.40(2H,s), 7.05–7.40(4H,m), 7.32(1H,dd,J=8.2&4.2 Hz), 7.56(1H,dd,J=8.2&1.6 Hz), 7.80(1H,m), 8.63(1H,dd, J=4.2&1.6 Hz).

Reference Example 50

(S)-7,8-Dihydro-7-(4-hydroxy-3-methylbutyl)-5-(4-methylphenyl)-8-oxo-N-(3,4,5-trimethoxybenzyl)-6-pyrido[3,4-b]pyridinecarboxamide Starting from the compound as obtained in Reference Example 49-Step 1 and THP-ether of (S)-4-amino-2-methyl-1-butanol, substantially the same reaction and work-up as Reference Example 19 was conducted to give the entitled compound as colorless crystals. m.p. 194–195° C. (recrystallized from acetone-ethyl ether) NMR(200 MHz, CDCl₃) ppm: same as the spectrum of the compound of Reference Example 49.

Reference Example 51

(R)-N-(3,5-Dimethoxybenzyl)-7,8-Dihydro-7-(4-hydroxy-3-methylbutyl)-5-(4-methylphenyl)-8-oxo-6-pyrido[3,4-b]pyridinecarboxamide Step 1

Using the compound as obtained in Reference Example 2-Step 2 and 3,5-dimethoxybenzylamine, substantially the same reaction and work-up as Reference Example 2-Step 4 was conducted to give N-(3,5-dimethoxybenzyl)-5-(4-methylphenyl)-8-oxo-8H-pyrano[3,4-b]pyridine-6-carboxamide as colorless crystals. m.p. 154–155° C. (recrystallized from ethyl acetate-isopropyl ether) NMR(200 MHz, CDCl₃) ppm: 2.45(3H,s), 3.78(6H,s), 4.41(2H,d,J=5.4 Hz), 6.41(3H,m), 7.17(2H,d,J=8.0 Hz), 7.23(1H,b), 7.33 (2H,d,J=8.0 Hz), 7.58(2H,m), 8.94(1H,dd,J=4.0&2.2 Hz).

Step 2

Starting from the compound as obtained in Step 1 and THP-ether of (R)-4-amino-2-methyl-1-butanol, substantially the same reaction and work-up as Reference Example 19 was conducted to give the entitled compound as colorless crystals. m.p. 169–172° C. (recrystallized from acetone-isopropyl ether) NMR(200 MHz, CDCl₃) ppm: 0.85(3H,d, J=6.8 Hz), 1.62(1H,m), 1.79(2H,m), 2.40(3H,s), 3.11(1H,b), 3.25–3.60(2H,m), 3.76(6H,s), 3.86(2H,m), 4.23(2H,d,J=5.6 Hz), 6.25(2H,d,J=2.2 Hz), 6.35(1H,t,J=2.2 Hz), 7.15–7.35 (4H,m), 7.30(1H,dd,J=8.4&4.2 Hz), 7.44(1H,m), 7.56(1H, dd,J=8.4&1.6 Hz), 8.65(1H,dd,J=4.2&1.6 Hz).

The compounds as described in Reference Example 52–55 were obtained as pale yellow oily substances using 2-chloro-4-(4-methylphenyl)-3-pyridinecarboxylic acid [prepared from 2-cyano-3-methyl-3-(4-methylphenyl) propenoic acid ethyl ester by condensation with N,N-dimethylacetamide dimethyl acetal, followed by cyclization using hydrogen chloride and alkaline hydrolysis of the ester group: m.p. 205–208° C. (decomposed)] and N-substituted-N-(substituted)benzylamines {i.e.,N-benzyl-N-(2-hydroxyethyl)amine, N-[3,5-bis(trifluoromethyl)benzyl]-N-(2-hydroxyethyl)amine, N-benzyl-N-[(S)-3-hydroxy-2-methylpropyl]amine, and N-[3,5-bis(trifluoromethyl)benzyl]3-N-[(S)-3-hydroxy-2-methylpropyl]amine, respectively} by substantially the same reaction and work-up as Reference Example 12-Step 2. The physico-chemical data are described below.

Reference Example 52

N-Benzyl-2-chloro-N-(2-hydroxyethyl)-4-(4-methylphenyl)-3-pyridinecarboxamide

NMR(200 MHz, CDCl₃) ppm: 2.43(3H×½,s), 2.46(3H× ½,s), 2.70–3.80(total 4H,m), 3.90(1H×½,d,J=15.4 Hz), 4.24 (1H×½,d,J=15.4 Hz), 4.51(1H×½,d,J=15.2 Hz), 4.94(1H× ½,d,J=15.2 Hz), 6.74(1H,m), 6.97(1H,m), 7.10–7.55(8H,m), 8.40(1H,m) (a 1:1 mixture of the amide rotamers).

Reference Example 53

N-[3,5-Bis(trifluoromethyl)benzyl]-2-chloro-N-(2-hydroxyethyl)-4-(4-methylphenyl)-3-pyridinecarboxamide
NMR(200 MHz, CDCl₃) ppm: 2.36(3H×7/11,s), 2.44(3H× 4/11,s), 2.80–3.80(total 4H,m), 4.16(1H×4/11,d,J=16.2 Hz), 4.41(1H×4/11,d,J=16.2Hz), 4.77(1H×7/11,d,J=15.0 Hz), 4.90 (1H×7/11,d,J=15.0 Hz), 7.10–7.50(6H,m), 7.76(2H,m), 8.42 (1H,m) (a 7:4 mixture of the amide rotamers).

Reference Example 54

N-Benzyl-2-chloro-N-[(S)-3-hydroxy-2-methylpropyl]4-(4-methylphenyl)3-pyridinecarboxamide NMR(200 MHz, CDCl₃) ppm: 0.59(3H×¼,d,J=7.0 Hz), 0.66(3H×¼,d,J=7.0 Hz), 0.77(3H×¼,d,J=3.8 Hz), 0.80(3H× ¼,d,J=3.8 Hz), 1.40–1.90(1H,m), 2.30–2.50(3H,m), 2.50–3.80(total 5H,m), 3.80–4.42(2H×¾,m), 5.05(2H×¼, m), 6.60–7.50(total 10H,m), 8.40(1H,m) (a 1:1 mixture of the amide rotamers).

Reference Example 55

N-[3,5-Bis(trifluoromethyl)benzyl]2-chloro-N-[(S)-3-hydroxy-2-methylpropyl]4-(4-methylphenyl)-3-pyridinecarboxamide NMR(200 MHz, CDCl₃) ppm: 0.54(3H×¼,d,J=7.0 Hz), 0.63(3H×¼,d,J=7.0 Hz), 0.79(3H×¼,d,J=7.0 Hz), 0.84(3H× ¼,d,J=7.0 Hz), 1.50–1.90(1H,m), 2.25–2.45(3H,m), 2.45–3.90(total 5H,m), 4.05–4.45(1H,m), 4.50–4.95(1H,m), 7.00–7.20(1H,m), 7.20–7.50(total 5H,m), 7.70–7.85(2H,m), 8.42(1H,m) (a 1:1 mixture of the amide rotasmers).

Formulation Example 1

| | |
|---|---|
| (1) Compound of Example 2 | 10.0 mg |
| (2) Lactose | 60.0 mg |
| (3) Corn starch | 35.0 mg |
| (4) Hydroxypropylmethyl cellulose | 3.0 mg |
| (5) Magnesium stearate | 2.0 mg |

A mixture of 10.0 mg of the compound as obtained in Example 2, 60.0 mg of lactose and 35.0 mg of corn starch was granulated along with 0.03 ml of an aqueous solution of 10 wt. % hydroxypropylmethyl cellulose (containing 3.0 mg of hydroxypropylmethyl cellulose), then dried at 40° C. and sieved. The granules thus obtained were mixed with 2.0 mg of magnesium stearate and tabletted. The green tablet thus obtained was sugar-coated with an aqueous suspension comprising sucrose, titanium dioxide, talc and arabic gum. The thus-coated tablet was glazed with bees wax to obtain a finally-coated tablet.

Formulation Example 2

| | |
|---|---|
| (1) Compound of Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound as obtained in Example 2 and 3.0 mg of magnesium stearate were granulated along with 0.07 ml of an aqueous solution of soluble starch (containing 7.0 mg of soluble starch), then dried and mixed with 70.0 mg of lactose and 50.0 mg of corn starch. The mixture was tabletted into a tablet.

Radioligand Receptor Binding Inhibitory Activity
Binding Inhibitory Activity Using Receptor from Human Lymphoblast Cells (IM-9)

The method of M. A. Cascieri et al. "Molecular Pharmacology 42, p.458 (1992)" was modified and used. The receptor was prepared from human lymphoblast cells (IM-9). IM-9 cells ($2 \times 10^5$ cells/ml) were inoculated and incubated for 3 days (one liter), which was then subjected to centrifuge for 5 minutes at 500×g to obtain cell pellets. The pellets were washed once with phosphate buffer (Flow Laboratories, CAT. No. 28–103-05), which were then crushed using Polytron.homogenizer "Kinematika, Germany" in 30 ml of 50 mM Tris-HCl buffer (pH 7.4) containing 120 mM sodium chloride, 5mM potassium chloride, 2 μg/ml chymostatin, 40 μg/ml bacitracin, 5 μg/ml phosphoramidon, 0.5 mM phenylmethyl sulfonyl fluoride, 1 mM ethylenediamine tetra-acetic acid, which was subjected to centrifuge at 40,000×g for 20 minutes. The residue was washed twice with 30 ml of the above-mentioned buffer, which was then preserved frozen (−80° C.) as a specimen of the receptor.

The specimen was suspended in a reaction buffer (50 mM Tri-HCl buffer (pH 7.4), 0.02% bovine serum albumin, 1 mM phenylmethylsulfonyl fluoride, 2 μg/chymostatin, 40 μg/ml bacitracin, 3 mM manganese chloride) and 100 ul portion was the suspension was used in the reaction. After addition of the sample and $^{125}$I-BHSP (0.46 KBq), the reaction was allowed to proceed in 0.2 ml of reaction buffer at 25° C. for 30 minutes. The amount of nonspecific binding was determined by adding substance P at a final concentration of $2 \times 10^{-6}$M. After the reaction, using a cell harvester (290 PHD, Cambridge Technology, Inc, U.S.A.), rapid filtration was carried out through a glass filter (GF/B, Whatman, U.S.A.) to stop the reaction. After washing three times with 250 ul of 50 mM of Tris-HCl buffer (pH 7.4) containing 0.02% bovine serum albumin, the radioactivity remaining on the filter was determined with a gamma counter. Before use, the filter was immersed in 0.1% polyethyleneimine for 24 hours and air-dried. The antagonistic activity of each test drug, in terms of the concentration necessary to cause 50% inhibition ($IC_{50}$) under the above-described conditions, was expressed in nM [Table 1]. (Radioligand means substance P labelled with $^{125}$I.) From the test results, it is understood that the compounds (I) and (Ia) or salts thereof of the present invention have an excellent substance P receptor antagonistic effect.

TABLE 1

| Test Compound (Example No.) | $IC_{50}$(nM) |
|---|---|
| 2 | 0.28 |
| 3 | 0.76 |
| 8 | 1.2 |
| 10 | 0.66 |
| 13 | 0.17 |
| 14 | 0.28 |
| 15 | 0.88 |
| 16 | 0.17 |
| 17 | 0.23 |
| 18 | 0.43 |
| 23 | 1.1 |
| 24 | 1.6 |
| 25 | 0.1 |
| 31 | 0.36 |
| 35 | 0.44 |
| 37 | 0.28 |
| 38 | 0.74 |
| 39 | 0.42 |
| 40 | 0.17 |
| 45 | 0.12 |
| 47 | 0.2 |

Binding Inhibitory Activity Toward Human $NK_2$ Receptor

First strand cDNA synthesized by reverse transcription at 48 C° for 1 h from 2 μg of human stomach poly $A^+$ RNA (Clontech Laboratories, Inc., USA) with Superscript RNase $H^-$ reverse transcriptase (GIBCO BRL Life Technologies, Inc., USA) and a gene specific 3'-primer (5'CTAACCCCTACCTCCCAACACTGCC-ACATTGGG-3') which was designed according to the published nucleotide sequence coding for human $NK_2$ receptor reported by A. Graham, B. Hopkins, S. J. Powell, P. Danks, and I. Briggs [Biochemical and Biophysical Research Communications 177, pp 8–16(1991)]. Polymerase chain reaction (PCR) was performed at 95° C. for 1 min, 55° C. for 2 min, 72° C. for 3 min for 50 cycles using tag DNA polymerase (Takara Shuzoh, Shiga, Japan), the above mentioned 3'-primer and a gene specific 5'-primer (5'-GAGCCAGGTCCTTTGTTCCAGACCCAGAAGCAG-3') which was also designed according to the published nucleotide sequence of human $NK_2$ receptor cCNA reported by A. Graham et al. described above. The resultant PCR product, 1.3 kilobase-pair DNA fragment was cloned into the Hincll site of pBluescript II SK$^+$ (Stratagene, USA).

The identity of the obtained clone was confirmed by nucleotide sequence analysis. In order to obtain an expression vector, the 1.3 kilobase-pair DNA fragment of human $NK_2$ receptor cDNA was placed downstream of the SRα promoter [Y. Takebe, M. Seiki, J. Fujisawa, P. Hoy, K. Yokota, K. Arai, M. Yoshida, and N. Arai "Molecular and Cellular Biology 8, p 466–472(1988)"].

COS-7 cells were cultured in DMEM medium (ICN Biomedicals, Inc., USA) supplemented with 10% fetal bovine serum at density of 3×10⁶ per 175-cm² flask (Nunc, Denmark) for 1 day. The cells were transfected with 30 μg of the above mentioned expression vector and 150 μg of transfectam (BioSepra, Inc., USA) at 37° C. for 5 h. After 3 days, cells were washed with phosphate buffer (ICN Biomedicals, Inc., Cat. No. 2810305, USA) containing 0.1% ethylenediamine tetra-acetic acid, detached from a flask and centrifuged at 170×g for 5 min to obtain cell pellets. The cell pellets were suspended in 50 mM Tris-HCl buffer (pH 7.4) (containing 120 mM sodium chloride, 5 mM potssium chloride, 2 μg/ml chymostatin, 40 μg/ml bacitracin, 5 μg/ml phosphoramidon, 0.5 mM phenylmethylsulfonyl fluoride and 1 mM ethylenediamine tetra-acetic acid), and were then disrupted by a Physicotron handy micro homogenizer NS-310E (Nichi-on-i Rikakiki Seisakusho, Chiba, Japan), which was subjected to centrifuge at 40,000×g for 60 min. The resulting pellet was washed twice with the above mentioned buffer, which was then preserved frozen at −80° C. as a specimen of the receptor.

The specimen was suspended in reaction buffer (50 mM Tris-HCl buffer (pH 7.4) containing 0.02% bovine serum albumin, 1 mM phenylmethylsulfonyl fluoride, 2 μg/ml chymostatin, 40 μg/ml bacitracin and 3 mM manganese chloride) to give a protein concentration of 0.6 mg/ml, and 0.1 ml of the portion of the suspension was employed in the reaction. After addition of a test compound and (2-[$^{125}$I]iodohistidyl$^1$)Neurokinin A (Amersham, UK) (74 TBq/mmol, 1.48 kBq, final concentration of 0.1 nM) to a final volume of 0.2 ml, the mixture was incubated at room temperature for 60 min in a 96-well plate. Then the mixture was filtered through a glass fiber filter (UniFilter-96, GF/B, Packard Instrument, Inc., USA) under reduced pressure on a Filter Mate Cell Harvester (Packard Instrument, Inc., USA). After washing the filter three times with 0.3 ml of the above mentioned reaction buffer, the radioactivity remaining on the filter was determined on a TopCound Micro Scintillation Counter (Packard Instrument, Inc., USA). The non-specific binding was defined as the binding activity in the presence of 10×10⁻⁶ M of neurokinin A (Peptide Instituted, Osaka, Japan). The filters were presoaked overnight in 0.5% bovine serum albumin. The antagonistic activity of each test compound was expressed in nM in terms of the concentration necessary to cause 50% inhibition (IC$_{50}$) under the above described conditions [Table 2].

TABLE 2

| Test Compound (Example No.) | IC$_{50}$(nM) |
| --- | --- |
| 22 | 7.5 |
| 27 | 6.2 |
| 33 | 9.5 |

From Table 2, it is apparent that the compound (I) or salts thereof of the present invention have excellent inhibitory activity toward human NK$_2$ receptor.

Inhibitory Effect on Plasma Extravasation Induced by Capsaicin in Trachea of Guinea Pigs Guinea pigs (Hartley type white male guinea pige), (n=6) were anesthetized with 35 mg/kg of pentobarbital injected intraperitoneally (i.p.), then test compounds were administered intravenously (i.v.). After 5 minutes, a mixed solution of capsaicin (150 μg/kg) and Evans' blue dye (20 mg/kg) was administered intravenously to cause reaction. Ten minutes later, test animals were sacrificed by cutting the aorta, then perfused through pulmonary artery with 50 ml of physiological saline. The trachea was excised, and its wet weight was measure. The trachea was incubated at room temperature in 1 ml of acetone-0.3% sodium sulfate (7:3) overnight and Evans' blue dye was extracted from the trachea. The extract solution was centrifuged at 2800 rpm for 5 minutes. The amount of Evans' blue dye in the supernatant was quantified by measuring absorbance at 620 mm.

Plasma extravasation was expressed in terms of the amount of Evans' blue dye (μg) relative to the weight of the trachea (g). The efficacy of the drug was evaluated by calculating the % inhibition in accordance with the following formula, or expressed in terms of $$\% \text{ inhibition} = \left(1 - \frac{A-B}{C-B}\right) \times 100$$

A: the amount of Evan's blue dye (μg/g) in each test animal
B: The mean amount of Evan's blue dye (μg/g) of the group untreated with capsaicin.
C: the mean amount of Evan's blue dye (μg/g) of control group
the dose (μg/kg) necessary to cause 50% inhibition (ID$_{50}$) under the above-described conditions [Table 3].

TABLE 3

| Test Compound (Example No.) | Dose (i.v) μg/kg (or ID$_{50}$; μg/kg, i.v)$^{b)}$ | Inhibition$^{a)}$ % |
| --- | --- | --- |
| 2 | (7.2) | |
| 3 | (4.2) | |
| 6 | (11) | |
| 7 | (2.6) | |
| 8 | (3.2) | |
| 12 | (41) | |
| 13 | (1.6) | |
| 14 | (3.2) | |
| 15 | 10 | 68.4*** |
| 16 | 10 | 60.5*** |
| 17 | (1.9) | |
| 18 | (2.6) | |
| 22 | 100 | 41.2* |
| 23 | 100 | 64.0* |
| 24 | 100 | 53.1* |

$^{a)}$Dunnett's test: *p < 0.05, p < 0.01, *p < 0.001
$^{b)}$ID$_{50}$ values are given in parentheses.

From Table 3, it is apparent that the compound (I) or salts thereof of the present invention have excellent inhibitory action on the plasma extravasation induced by capsaicin.

What is claimed is:

1. A compound of the formula:

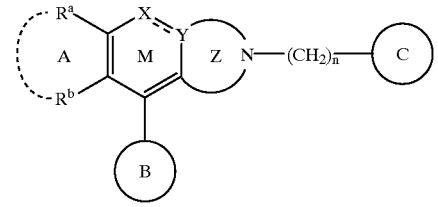

wherein ring M is a heterocyclic ring wherein —X═Y< —N═C<;
and n is an integer from 1 to 6, or a salt thereof;
R$^a$ and R$^b$ are the same or different and represent, independently, (1) a hydrogen atom,
(2) a $C_{1-6}$ alkyl group optionally having from 1 to 5 substituents selected from
 (a) a hydroxyl group,
 (b) a $C_{1-6}$ alkoxy group,
 (c) a $C_{1-6}$ alkylthio group,
 (d) an amino group,
 (e) a $C_{1-7}$ acylamino group,
 (f) a carboxyl group,
 (g) a nitro group,
 (h) a mono- or di-$C_{1-6}$ alkylamino group,
 (i) a mono- or di-$C_{1-6}$ cycloalkylamino group,
 (j) a $C_{6-10}$ arylamino group,
 (k) a 5-membered to 9-membered cyclicamino group which may have 1 to 3 hetero atoms selected from nitrogen, oxygen and sulfur atoms in addition to the nitrogen atom in the amino group,
 (l) a 5-membered to 6-membered aromatic heterocyclic group having from 1 to 3 hetero atoms selected from nitrogen, oxygen and sulfur atoms, in addition to carbon atoms,
 (m) a 5-membered to 9-membered non-aromatic heterocyclic ring having from 1 to 3 hetero atoms selected from nitrogen, oxygen and sulfur atoms, in addition to carbon atoms,
 (n) a $C_{1-4}$ alkylsulfonylamino group,
 (o) a $C_{1-6}$ alkyl-carbonyloxy group and
 (p) a halogen atom,
(3) an optionally halogenated $C_{1-6}$ alkoxy group,
(4) an optionally halogenated $C_{1-6}$ alkylthio group,
(5) a $C_{3-10}$ cycloalkyl group,
(6) a $C_{6-10}$ aryl group,
(7) a $C_{1-7}$ acylamino group,
(8) a $C_{1-3}$ acyloxy group,
(9) a hydroxy group,
(10) a nitro group,
(11) a cyano group,
(12) an amino group,
(13) a mono- or di-$C_{1-6}$ alkylamino group,
(14) a 5-membered to 9-membered cyclicamino group which may have 1 to 3 hetero atoms selected from nitrogen, oxygen and sulfur atoms, in addition to the nitrogen atom in the amino group,
(15) a $C_{1-6}$ alkylcarbonylamino group,
(16) a $C_{1-6}$ alkylsulfonylamino group,
(17) a $C_{1-6}$ alkoxycarbonyl group,
(18) a carboxyl group,
(19) a $C_{1-6}$ alkylcarbonyl group,
(20) a carbamoyl group,
(21) a mono- or di-$C_{1-6}$ alkylcarbamoyl group,
(22) $C_{1-6}$ alkylsulfonyl group;
the Ring B is a benzene ring which may have 1 to 4 substituents selected from
(1) a halogen atom,
(2) a $C_{1-6}$ alkyl group optionally having from 1 to 5 substituents selected from
 (a) a hydroxyl group,
 (b) an amino group,
 (c) a carboxyl group,
 (d) a nitro group,
 (e) a mono- or di-$C_{1-6}$ alkylamino group,
 (f) a $C_{1-6}$ alkyl-carbonyloxy group and
 (g) a halogen atom,
(3) an optionally halogenated $C_{1-6}$ alkoxy group,
(4) an optionally halogenated $C_{1-6}$ alkylthio group,
(5) a $C_{6-10}$ aryl group,
(6) a $C_{1-7}$ acylamino group,
(7) a $C_{1-3}$ acyloxy group,
(8) a hydroxy group,
(9) a nitro group,
(10) a cyano group,
(11) an amino group,
(12) a mono- or di-$C_{1-6}$ alkylamino group,
(13) a 5-membered to 9-membered cyclicamino group which may have 1 to 3 hetero atoms selected from nitrogen, oxygen and sulfur atoms, in addition to the nitrogen atom in the amino group,
(14) a $C_{1-6}$ alkylcarbonylamino group,
(15) a $C_{1-6}$ alkylsulfonylamino group,
(16) a $C_{1-6}$ alkoxycarbonyl group,
(17) a carboxyl group,
(18) a $C_{1-6}$ alkylcarbonyl group,
(19) a carbamoyl group,
(20) a mono- or di-$C_{1-6}$ alkylcarbamoyl group,
(21) a $C_{1-6}$ alkylsulfonyl group;
the Ring C is a benzene ring optionally having 1 to 5 substituents selected from
(1) a halogen atom,
(2) an optionally halogenated $C_{1-10}$ alkyl group,
(3) an amino-substituted $C_{1-4}$ alkyl group,
(4) a mono- or di-$C_{1-4}$ alkylamino-substituted $C_{1-4}$ alkyl group,
(5) a carboxyl-substituted $C_{1-4}$ alkyl group,
(6) a hydroxy-substituted $C_{1-4}$ alkyl group,
(7) a $C_{1-4}$ alkoxy-carbonyl-substituted $C_{1-4}$ alkyl group,
(8) a $C_{3-10}$ cycloalkyl group,
(9) a nitro group,
(10) a cyano group,
(11) a hydroxyl group,
(12) an optionally-halogenated $C_{1-10}$ alkoxy group,
(13) an optionally-halogenated $C_{1-4}$ alkylthio group,
(14) an amino group,
(15) a mono- or di-$C_{1-4}$ alkylamino group,
(16) a 5-membered to 9-membered cyclic amino group optionally having 1 to 3 hetero atoms selected from nitrogen, oxygen and sulfur atoms, in addition to the nitrogen atom in the amino group,
(17) a $C_{1-4}$ alkyl-carbonylamino group,
(18) an aminocarbonyloxy group,
(19) a mono- or di-$C_{1-4}$ alkylaminocarbonyloxy group,
(20) a $C_{1-4}$ alkylsulfonylamino group,
(21) a $C_{1-4}$ alkoxy-carbonyl group,
(22) an aralkyloxycarbonyl group,
(23) a carboxyl group,
(24) a $C_{1-6}$ alkyl-carbonyl group,
(25) a $C_{3-6}$ cycloalkyl-carbonyl group,
(26) a carbamoyl group,
(27) a mono- or di-$C_{1-4}$ alkylcarbamoyl group,
(28) a $C_{1-6}$ alkylsulfonyl group and
(29) a 5-membered or 6-membered aromatic monocyclic heterocyclic group having 1 to 4 hetero atoms selected from nitrogen, oxygen and sulfur atoms, which may have 1 to 3 substituents selected from an optionally halogenated $C_{1-4}$ alkyl;

the Ring Z is

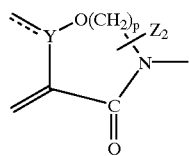

wherein p is an integer of from 2 to 5 and $Z_2$ is a hydrogen atom, an $C_{1-4}$ alkyl group or a hydroxyl group.

2. A compound as claimed in claim 1, wherein n is 1.

3. A compound as claimed in claim 1, wherein $R^a$ and $R^b$ are the same or different and represent, independently, (1) a hydrogen atom, (2) a $C_{1-6}$ alkoxy-$C_{1-6}$ alkyl group, (3) a $C_{1-6}$ alkylthio-$C_{1-6}$ alkyl group, (4) an amino-$C_{1-6}$ alkyl group, (5) a $C_{1-7}$ acylamino-$C_{1-6}$ alkyl group, (6) a mono- or di-$C_{1-6}$ alkylamino-$C_{1-4}$ alkyl group, (7) $C_{3-10}$ cycloamino-$C_{1-6}$ alkyl group, (8) a $C_{1-6}$ alkyl group having 5-membered or 6-membered cycloamino optionally substituted by $C_{1-6}$ alkyl group, (9) a $C_{1-6}$ alkylsulfonylamino-$C_{1-6}$ alkyl group, or

(10) a $C_{1-6}$ alkylcarbonyloxy-$C_{1-6}$ alkyl

Ring B is a benzene ring optionally having 1 to 3 substituents selected from a halogen atom, an optionally halogenated $C_{1-4}$ alkyl group and an optionally halogenated $C_{1-4}$ alkoxy group;

Ring C is a benzene ring opitionally having 1 to 3 substituents selected from a halogen atom, an optionally halogenated $C_{1-4}$ alkyl group, an optionally halogenated $C_{1-4}$ alkoxy group, an amino group optionally substituted by $C_{1-4}$ alkyl group, a $C_{1-3}$ acyloxy group and a hydroxyl group;

and n is an integer of 1.

4. A process for producing a compound as claimed in claim 1, characterized by cyclizing a compound of a formula:

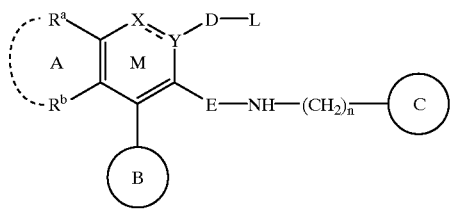

wherein D is —O(CH$_2$)$_p$— wherein p has the same meaning as that in claim 1, E is

L represents a leaving group, and the other symbols are the same meanings as those in claim 1, or a salt thereof.

5. A pharmaceutical composition comprising a compound or pharmaceutically acceptable salt thereof as claimed in claim 1.

6. A method of antagonizing Substance P receptor to a subject in need comprising the step of:

administering a composition of claim 1 to said subject in a pharmaceutically effective amount.

7. A method of antagonizing neurokinin A receptor to a subject in need comprising the step of:

administering a composition of claim 1 to said subject in a pharmaceutically effective amount.

8. A method for antagonizing tachykinin receptor in mammals which comprises administrating to a subject in need, an effective amount of a compound or pharmaceutically acceptable salt thereof as claimed in claim 1.

9. A method for treating disorders of micturition in mammals which comprises administrating-to a subject in need an effective amount of a compound or pharmaceutically acceptable salt thereof as claimed in claim 1.

10. A method for treating disorders of asthma, migraine, irritable bowel syndrome, pain, cough or emesis in mammals which comprises administrating to a subject in need an effective amount of a compound or pharmaceutically acceptable salt thereof as claimed in claim 1.

11. A compound as claimed in claim 1, which may be any one of:

4-[3,5-Bis(trifluoromethyl)benzyl]-2,3,4,5-tetrahydro-5-oxo-6-phenylpyrido[3,2-f][1,4]oxazepine;

5-[3,5-Bis(trifluoromethyl)benzyl]-2,3,4,5-tetrahydro-6-oxo-7-phenyl-6H-pyrido[2,3-b][1,5]oxazocine;

4-[3,5-Bis(trifluoromethyl)benzyl]-2,3,4,5-tetrahydro-7-methyl-5-oxo-6-phenylpyrido[3,2-f][1,5]oxazepine;

5-[3,5-Bis(trifluoromethyl)benzyl]-2,3,4,5-tetrahydro-8-methyl-6-oxo-7-phenyl-6H-pyrido[2,3-b][1,4]oxazocine;

(S)-5-[3,5-Bis(trifluoromethyl)benzyl]-2,3,4,5-tetrahydro-3,8-dimethyl-6-oxo-7-phenyl-6H-pyrido[2,3-b][1,5]oxazocine;

(R)-5-[3,5-Bis(trifluoromethyl)benzyl]-2,3,4,5-tetrahydro-3,8-dimethyl-6-oxo-7-phenyl-6H-pyrido[2,3-b][1,5]oxazocine;

4-[3,5-Bis(trifluoromethyl)benzyl]-2,3,4,5-tetrahydro-8-methyl-5-oxo-6-phenylpyrido[3,2-f][1,4]oxazepine;

5-[3,5-Bis(trifluoromethyl)benzyl]-2,3,4,5-tetrahydro-9-methyl-6-oxo-7-phenyl-6H-pyrido[2,3-b][1,5]oxazocine;

8-Acetoxymethyl-4-[3,5-bis(trifluoromethyl)benzyl]-2,3,4,5-tetrahydro-5-oxo-6-phenylpyrido[3,2-f][1,4]oxazepine;

9-Acetoxymethyl-5-[3,5-bis(trifluoromethyl)benzyl]-2,3,4,5-tetrahydro-6-oxo-7-phenyl-6H-pyrido[2,3-b][1,5]oxazocine;

4-[3,5-bis(trifluoromethyl)benzyl]-8-chloromethyl-2,3,4,5-tetrahydro-5-oxo-6-phenylpyrido[3,2-f][1,4]oxazepine;

4-[3,5-Bis(trifluoromethyl)benzyl]-2,3,4,5-tetrahydro-8-methoxymethyl-5-oxo-6-phenylpyrido[3,2-f][1,4]oxazepine;

4-[3,5-Bis(trifluoromethyl)benzyl]-2,3,4,5-tetrahydro-8-(2-methylethyl)-5-oxo-6-phenylpyrido[3,2-f][1,4]oxazepine;

4-[3,5-Bis(trifluoromethyl)benzyl]-2,3,4,5-tetrahydro-8-methylthiomethyl-5-oxo-6-phenylpyrido[3,2-f][1,4]oxazepine;

8-Aminomethyl-4-[3,5-bis(trifluoromethyl)benzyl]-2,3,4,5-tetrahydro-5-oxo-6-phenylpyrido[3,2-f][1,4]oxazepine;

4-[3,5-Bis(trifluoromethyl)benzyl]-2,3,4,5-tetrahydro-8-methylaminomethyl-5-oxo-6-phenylpyrido[3,2-f][1,4]oxazepine;

4-[3,5-Bis(trifluoromethyl)benzyl]-8-dimethylaminomethyl-2,3,4,5-tetrahydro-5-oxo-6-phenylpyrido[3,2-f][1,4]oxazepine;

4-[3,5-Bis(trifluoromethyl)benzyl]-8-cyclopropylaminomethyl-2,3,4,5-tetrahydro-5-oxo-6-phenylpyrido[3,2-f][1,4]oxazepine;

4-[3,5-Bis(trifluoromethyl)benzyl]-2,3,4,5-tetrahydro-8-(N-methylpiperazinomethyl)-5-oxo-6-phenylpyrido[3,2-f][1,4]oxazepine;

8-Acetylaminomethyl-4-[3,5-bis(trifluoromethyl)benzyl]-2,3,4,5-tetrahydro-5-oxo-6-phenylpyrido[3,2-f][1,4]oxazepine;

4-[3,5-Bis(trifluoromethyl)benzyl]-2, 3,4,5-tetrahydro-8-methanesulfonylaminomethyl-5-oxo-6-phenylpyrido[3,2-f][1,4]oxazepine;

4-[3,5-Bis(trifluoromethyl)benzyl]-8-hydroxymethyl-2,3,4,5-tetrahydro-5-oxo-6-phenylpyrido[3,2-f][1,4]oxazepine;

4-[3,5-Bis(trifluoromethyl)benzyl]-2,3,4,5-tetrahydro-5-oxo-6-phenylpyrido[3,2-f][1,4]oxazepine-8-carboxylic acid;

4-[3,5-Bis(trifluoromethyl)benzyl]-2,3,4,5-tetrahydro-5-oxo-6-phenylpyrido[3,2-f][1,4]oxazepine-8-carboxamide;

4-[3,5-Bis(trifluoromethyl)benzyl]-N-methyl-2,3,4,5-tetrahydro-5-oxo-6-phenylpyrido[3,2-f][1,4]oxazepine-8-carboxamide;

4-[3,5-Bis(trifluoromethyl)benzyl]-N,N-dimethyl-2,3,4,5-tetrahydro-5-oxo-6-phenylpyrido[3,2-f][1,4]oxazepine-8-carboxamide;

4-[3,5-Bis(trifluoromethyl)benzyl]-N-n-butyl-2,3,4,5-tetrahydro-5-oxo-6-phenylpyrido[3,2-f][1,4]oxazepine-8-carboxamide;

4-[3,5-Bis(trifluoromethyl)benzyl]-2,3,4,5-tetrahydro-5-oxo-6-phenyl-8-piperidinocarbonylpyrido[3,2-f][1,4]oxazepine;

4-[3,5-Bis(trifluoromethyl)benzyl]-2,3,4,5-tetrahydro-8-morpholinocarbonyl-5-oxo-6-phenylpyrido[3,2-f][1,4]oxazepine;

4-[3,5-Bis(trifluoromethyl)benzyl]-2,3,4,5-tetrahydro-8-[1-(4-methylpiperazinyl)carbonyl]-5-oxo-6-phenyl-pyrido[3,2-f][1,4]oxazepine-8-carboxamide;

2,3,4,5-Tetrahydro-5-oxo-6-phenyl-4-(3,4,5-trimethoxybenzyl)pyrido[3,2-f][1,4]oxazepine;

4-(3,4-Dichlorobenzyl)-2,3,4,5-tetrahydro-5-oxo-6-phenylpyrido[3,2-f][1,4]oxazepine;

4-(3,4-Dimethoxybenzyl)-2,3,4,5-tetrahydro-5-oxo-6-phenylpyrido[3,2-f][1,4]oxazepine;

4 -Benzyl-2,3,4,5-tetrahydro-5-oxo-6-phenylpyrido[3,2-f][1,4]oxazepine;

2,3,4,5-Tetrahydro-6-oxo-7-phenyl-5-(3,4,5-trimethoxybenzyl)-6H-pyrido[2,3-b][1,5]oxazocine;

(S)-5-Benzyl-2,3,4,5-tetrahydro-3-methyl-6-oxo-7-phenyl-6H-pyrido[2,3-b][1,5]oxazocine;

(R)-5-Benzyl-2,3,4,5-tetrahydro-3-methyl-6-oxo-7-phenyl-6H-pyrido[2,3-b][1,5]oxazocine;

(S)-5-[3,5-Bis(trifluoromethyl)benzyl]-2,3,4,5-tetrahydro-3-methyl-6-oxo-7-phenyl-6H-pyrido[2,3-b][1,5]oxazocine;

(R)-5-[3,5-Bis(trifluoromethyl)benzyl]-2,3,4,5-tetrahydro-3-methyl-6-oxo-7-phenyl-6H-pyrido[2,3-b][1,5]oxazocine;

4-Benzyl-2,3,4,5-tetrahydro-5-oxo-6-(4-methylphenyl)pyrido[3,2-f][1,4]oxazepine;

4-[3,5-Bis(trifluoromethyl)benzyl]2,3,4,5-tetrahydro-5-oxo-6-(4-methylphenyl)pyrido[3,2-f][1,4]oxazepine;

(S)-5-Benzyl-2,3,4,5-tetrahydro-3-methyl-7-(4-methylphenyl)-6-oxo-6H-pyrido[2,3-b][1,5]oxazocine; and (S)-5-[3,5-Bis(trifluoromethyl)benzyl]2,3,4,5-tetrahydro-3-methyl-7-(4-methylphenyl)-6-oxo-6H-pyrido[2,3-b][1,5]oxazocine.

* * * * *